United States Patent
Brookfield et al.

(10) Patent No.: US 8,268,840 B2
(45) Date of Patent: Sep. 18, 2012

(54) PYRIMIDINYL PYRIDONE INHIBITORS OF KINASES

(75) Inventors: Frederick Brookfield, Wallingford (GB); Florence Eustache, Oxfordshire (GB); Michael Patrick Dillon, San Francisco, CA (US); David Michael Goldstein, San Jose, CA (US); Leyi Gong, San Mateo, CA (US); Xiaochun Han, Sunnyvale, CA (US); Joan Heather Hogg, Sunnyvale, CA (US); Jaehyeon Park, Sunnyvale, CA (US); Deborah Carol Reuter, Los Altos, CA (US); Eric Brian Sjogren, Mountain View, CA (US)

(73) Assignee: Roche Palo Alto LLC, Roche Palo Alto, CA (US)

( * ) Notice: Subject to any disclaimer, the term of this patent is extended or adjusted under 35 U.S.C. 154(b) by 479 days.

(21) Appl. No.: 12/387,181

(22) Filed: Apr. 29, 2009

(65) Prior Publication Data
US 2009/0270389 A1  Oct. 29, 2009

Related U.S. Application Data

(60) Provisional application No. 61/048,574, filed on Apr. 29, 2008.

(51) Int. Cl.
*A01N 43/90* (2006.01)
*A61K 31/519* (2006.01)
*C07D 471/00* (2006.01)

(52) U.S. Cl. .................... 514/264.1; 544/279
(58) Field of Classification Search ............. 544/279; 514/264.1
See application file for complete search history.

(56) References Cited

U.S. PATENT DOCUMENTS

| 4,301,281 A | * | 11/1981 | Scotese et al. ............. 544/80 |
| 6,498,163 B1 | * | 12/2002 | Boschelli et al. .......... 514/264.1 |
| 2005/0187230 A1 | | 8/2005 | Ding et al. |

FOREIGN PATENT DOCUMENTS

| WO | 9501977 A1 | 1/1995 |
| WO | 9518127 A1 | 7/1995 |
| WO | 0123389 A2 | 4/2001 |
| WO | 2001-055148 | * 8/2001 |
| WO | 0155148 A1 | 8/2001 |
| WO | 0224703 A1 | 3/2002 |
| WO | 2007136465 A2 | 11/2007 |

* cited by examiner

*Primary Examiner* — Paul V. Ward
(74) *Attorney, Agent, or Firm* — George W. Johnston; Dennis P. Tramaloni; Jennifer L. Kisko

(57) ABSTRACT

This application discloses novel pyrimidinyl pyridone derivatives according to formula I, wherein A, $R^1$, $R^2$, $R^3$, and m

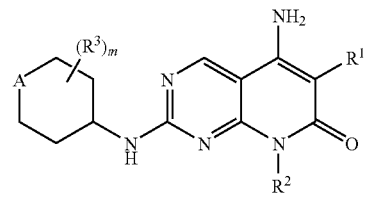

are defined as described herein, which inhibit JNK. The compounds disclosed herein are useful to modulate the activity of JNK and treat diseases associated with excessive JNK activity. The compounds are useful to treat autoimmune, inflammatory, metabolic, and neurological diseases as well as cancer. Also disclosed are compositions comprising the compound of formula I and methods of treatment comprising administering a therapeutically effective amount of the compound of formula I to a subject in need thereof.

8 Claims, No Drawings

PYRIMIDINYL PYRIDONE INHIBITORS OF KINASES

CROSS-REFERENCE TO RELATED APPLICATIONS

This application is entitled to the benefit of U.S. provisional patent application Ser. No. 61/048,574 filed on Apr. 29, 2008, the disclosure of which is incorporated herein by reference.

FIELD OF THE INVENTION

This invention relates generally to the fields of medicinal chemistry and treatment of inflammatory disorders. More particularly, the invention relates to pyrimidinyl pyridone inhibitors of JNK, methods and formulations for inhibiting JNK and treating JNK-mediated disorders, and the like.

BACKGROUND OF THE INVENTION

JNK The c-Jun N-terminal kinases (JNKs) are members of mitogen-activated protein kinase family along with p38 and extracellular signal-regulated kinases (ERKs). Three distinct genes (jnk1, jnk2 and jnk3) encoding 10 splice variants have been identified. JNK1 and JNK2 are expressed in a wide variety of tissues, whereas JNK3 is mainly expressed in neurons, and to a lesser extent in heart and testes. Members of JNK family are activated by pro-inflammatory cytokines such as tumor necrosis factor $\alpha$ (TNF-$\alpha$) and interleukin-1$\beta$ (IL-1$\beta$), as well as environmental stresses. The activation of JNKs is mediated by its upstream kinases, MKK4 and MKK7, via dual phosphorylation of Thr-183 and Tyr-185. It has been shown that MKK4 and MKK7 can be activated by the diverse upstream kinases, including MEKK1 and MEKK4, depending upon the external stimuli and cellular context. The specificity of JNK signaling is achieved by forming a JNK-specific signaling complex containing multiple components of the kinase cascade by use of scaffold proteins called JNK-interacting proteins. JNKs have been shown to play important roles in inflammation, T cell functions, apoptosis and cellular survival by phosphorylating specific substrates, including transcription factors such as c-Jun, the component of activator protein-1 (AP1) family, and ATF2, as well as non-transcription factors such as IRS-1 and Bcl-2. Over-activation of JNK is believed to be an important mechanism in autoimmune, inflammatory, metabolic, neurological diseases as well as cancer.

Rheumatoid arthritis (RA) is a systemic autoimmune disease characterized by chronic inflammation of the joints. In addition to the joint swelling and pain caused by the inflammatory process, most RA patients ultimately develop debilitating joint damage and deformation. Several lines of compelling pharmacological and genetic evidence in cellular and animal models strongly suggest the relevance and importance of the activated JNK in the pathogenesis of RA. First, abnormal activation of JNK was detected in both human arthritic joints from RA patients and rodent arthritic joints from animal models of arthritis. In addition, inhibition of JNK activation by selective JNK inhibitors blocked proinflammatory cytokines and MMP production in human synoviocytes, macrophages and lymphocytes. Importantly, administration of the selective JNK inhibitors in rats with adjuvant arthritis or in mice with collagen-induced arthritis effectively protected joints from destruction and significantly reduced paw swelling by inhibiting cytokine and collagenase expression.

Asthma is a chronic inflammatory disease of airways, characterized by the presence of a cellular inflammatory process and by bronchial hyper-responsiveness associated with structural changes of the airways. This disorder has been shown to be driven by many cell types in the airways, including T lymphocytes, eosinophils, mast cells, neutrophils and epithelial cells. JNKs have emerged as promising therapeutic targets for asthma based upon the recent proof-of-concept studies: it has been shown that JNK inhibitors significantly blocked RANTES production in activated human airway smooth cells. More importantly, the JNK inhibitors showed good efficacy in chronic rat and mouse models for their abilities to reduce cellular infiltration, inflammation, hyper-responsiveness, smooth muscle proliferation, and IgE production. These observations suggest important roles of JNKs in the allergic inflammation, airway remodeling process associated with hyper-responsiveness. Therefore, blockade of JNK activity is expected to be beneficial for the treatment of asthma.

Type 2 diabetes is the most serious and prevalent metabolic disease characterized by insulin resistance and insulin secretion impairment as a result of chronic low-level inflammation and abnormal lipid metabolism associated with oxidative stress. It has been reported that JNK activity is abnormally elevated in various diabetic target tissues under obese and diabetic conditions. Activation of the JNK pathway by pro-inflammatory cytokines and oxidative stresses negatively regulates insulin signaling via phosphorylation of insulin receptor substrate-1 (IRS-1) at $Ser^{307}$, therefore contributes to insulin resistance and glucose tolerance. Compelling genetic evidence came from elegant animal model studies using $jnk^{-/-}$ mice crossed with either genetic (ob/ob) obese mice or dietary obese mice. Loss of JNK1 ($JNK1^{-/-}$), but not JNK2 functions ($jnk2^{-/-}$), protected obese mice from body gains, increased steady-state levels of blood glucose, and decreased plasma insulin levels. These studies demonstrated the potential utility of JNK inhibitor in the treatment of obesity/type 2 diabetes.

Neurodegenerative diseases, such as Alzheimer's (AD), Parkinson's (PD) and Stroke are CNS diseases characterized by synaptic loss, neuronal atrophy and death. The JNK pathway leading to c-Jun activation has been shown to play a causal role in apoptosis of isolated primary embryonic neurons and multiple neuronal cell lines upon induction of a variety of stimuli. Over-activation of JNK was observed in human brains from AD patients or rodent brain sections derived from animal models of neurodegenerative diseases. For example, increased phospho-JNKs were detected in the post-mortem brains from the AD patients. Administration of JNK inhibitory peptide (JIP-1 peptide) in the rodent model of AD induced by $\beta$-amyloid peptide administration prevented the impairment of synaptic plasticity. In the animal models of PD (MPTP model), elevated phospho-MKK4 and phospho-JNKs were observed concomitantly with the neuronal cell death. Adenoviral gene transfer of JNK inhibitory peptide (JIP-1 peptide) into striatum of mice attenuated behavioral impairment by inhibiting MPTP-mediated JNK, c-Jun and caspase activation, therefore blocking neuronal cell death in the substantia nigra. In addition, in the animal model of ischemic stroke induced by glutamate excitotoxicity, mice deficient in JNK3, but not JNK1 or JNK2, were resistant to kainic acid (glutamate receptor agonist)-mediated seizure or neuronal death. These data suggest JNK3 was mainly responsible for glutamate excitotoxicity, an important component in ischemic conditions. Taken together, data has emerged suggesting JNKs as attractive target for multiple CNS diseases associated with neuronal cell death.

Uncontrolled cellular growth, proliferation and migration along with de-regulated angiogenesis lead to the formation of malignant tumors. The JNK signal transduction pathway may not act exclusively in apoptosis, sustained JNK activation leading to AP1 activation has recently been implicated to contribute to the cellular survival of specific cancer types such as glial tumors and BCL-ABL transformed B lymphoblasts. In the case of glial tumors, enhanced JNK/AP1 activity was seen in most of the primary brain tumor samples. For the transformed B lymphoblasts, BCL-ABL was shown to activate the JNK pathway which in turn up-regulated expression of anti-apoptotic bcl-2 gene. Interestingly, the multi-drug resistance and hyper-proliferation seen in treatment-refractory AML (acute myeloid leukemia) patients has been causally linked to the sustained JNK activity present in these AML samples. Activation of JNK in leukemic cells resulted in induced expression of efflux pumps such as mdr1 and MRP1 responsible for multidrug resistance. Also, genes with a survival benefit in response to oxidative stress including glutathione-S-transferase π and γ-glutamyl cysteine synthase were also upregulated by the activated JNK pathway.

Accordingly, JNK modulators are useful in treating a variety of diseases and/or conditions. The role of cyclin-dependent kinases ("cdks") in the regulation of cellular proliferation is well established. There is an extensive body of literature validating the use of compounds that inhibit targets in the Cdk4, Cdk2 and Cdk1 pathways as anti-proliferative therapeutic agents. See, e.g., J. Lukas et al., *Nature* (1995) 79:573-82; J. R. Nevins, *Science* (1992) 258:424-29; I. K. Lim et al., *Mol Carcinogen* (1998) 23:25-35; S. W. Tam et al., *Oncogene* (1994) 9:2663-74; B. Driscoll et al., *Am. J. Physiol.* (1997) 273 (*Lung Cell. Mol. Physiol.*) L941-L949; and J. Sang et al., *Chin. Sci. Bull.* (1999) 44:541-44. Inhibitors of cellular proliferation act as reversible cytostatic agents that are useful in the treatment of disease processes which feature abnormal cellular growth, such as cancers and other cell proliferative disorders including, for example inflammation (e.g. benign prostate hyperplasia, familial adenomauosis, polyposis, neuro-fibromatosis, atherosclerosis, pulmonary fibrosis, arthritis, psoriasis, inflammatory bowel disease, transplantation rejections infections), viral infections (including, without limitation, herpesvirus, poxvirus, Epstein-Barr virus), autoimmune disease (e.g. lupus, rheumatoid arthritis, psoriasis, inflammatory bowel disease), neurodegenerative disorders (including, without limitation, Alzheimer's disease), and neurodegenerative diseases (e.g. Parkinson's disease, amyotrophic lateral sclerosis, retinitis pigmentosa, spinal muscular atrophy, and cerebral degeneration).

SUMMARY OF THE INVENTION

In one aspect, the application provides a compound of formula I

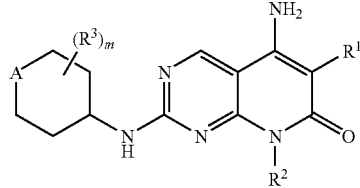

including enantiomers, diastereomers, racemic mixtures and pharmaceutically acceptable salts thereof, wherein:

$R^1$ is $R^{1a}$ or $R^{1b}$;

$R^{1a}$ is H, halo, acyl, lower alkyl, lower haloalkyl, lower alkoxy, —CN, or —OH;

$R^{1b}$ is cycloalkyl, heterocycloalkyl, or phenyl, optionally substituted with one or more $R^{1b'}$;

each $R^{1b'}$ is independently halo, —OH, lower alkoxy, amino, lower alkyl or lower haloalkyl;

$R^2$ is lower alkyl, lower heteroalkyl, lower alkoxy, cycloalkyl, phenyl, heterocycloalkyl, or heteroaryl, optionally substituted with one or more $R^{2a}$;

each $R^{2a}$ is independently —OH, halo, lower alkyl, amino, lower alkoxy, or $R^{2b}$;

$R^{2b}$ is cycloalkyl, heterocycloalkyl, or phenyl, optionally substituted with one or more $R^{2b'}$;

each $R^{2b'}$ is independently halo, —OH, lower alkoxy, amino, lower alkyl or lower haloalkyl;

$R^3$ is halo, amino, lower alkyl, lower alkoxy, or lower haloalkyl;

A is O or A';

A' is $C(R^5)(R^{5'})$ or $N(R^{5b})$;

$R^5$ and $R^{5'}$ are independently $R^{5a}$ or $R^{5b}$;

$R^{5a}$ is —H, halo, —OH, or A";

$R^{5b}$ is lower alkyl, A", or lower heteroalkyl, optionally substituted with one or more $R^{6a}$;

$R^{6a}$ is —OH, halo, lower alkyl, lower haloalkyl, lower alkoxy, or amino;

A" is —NHC(=O)$R^7$, —NHC(=O)O$R^7$, —N($R^9$)S(=O)$_2R^7$, —S(=O)$_2R^7$, —C(=O)$R^8$, or —C(=O)O$R^7$;

$R^7$ is lower alkyl or cycloalkyl;

$R^8$ is cycloalkyl, cycloalkyl lower alkyl, heterocycloalkyl, heterocycloalkyl lower alkyl, or lower alkyl, each of which may be optionally substituted with halo, —OH, lower alkoxy, amino, or lower alkyl;

$R^9$ is H or lower alkyl; and m is 0 to 4.

In certain embodiments, A is A' and A' is $C(R^5)(R^{5'})$.

In certain embodiments, $R^5$ is $R^{5a}$ and $R^{5a}$ is H.

In certain embodiments, $R^2$ is cycloalkyl, heterocycloalkyl, phenyl, phenylalkyl, cycloalkyl alkyl, lower alkyl, or lower heteroalkyl.

In certain embodiments, $R^{5'}$ is $R^{5a}$ and $R^{5a}$ is H.

In certain embodiments, the compound is selected from the group consisting of:

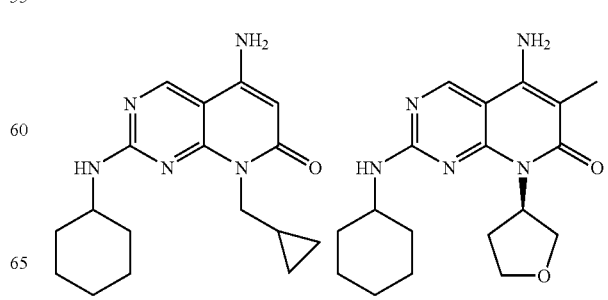

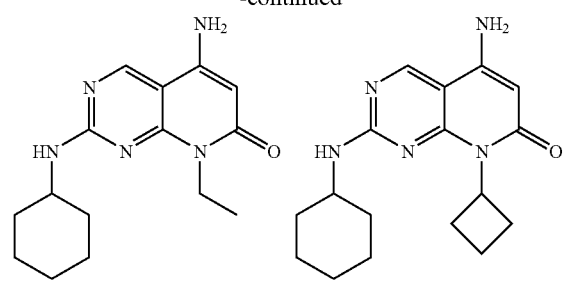
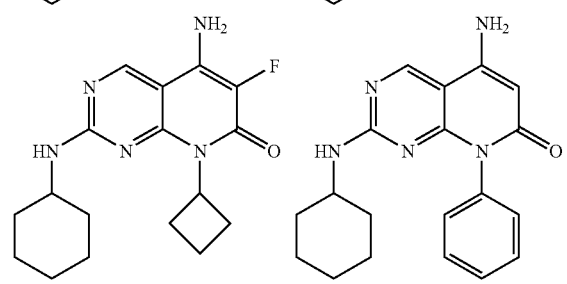
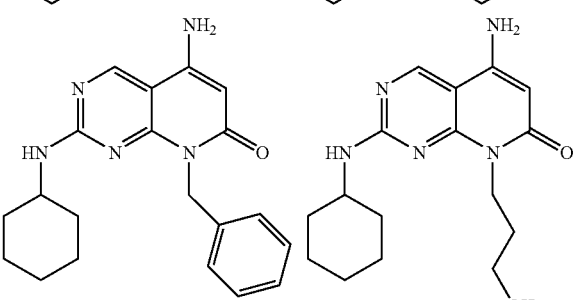
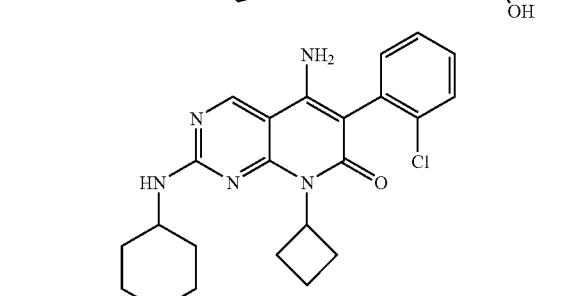
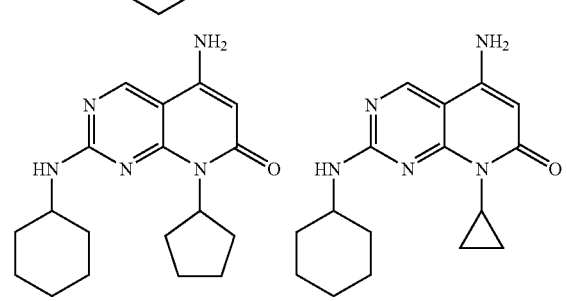
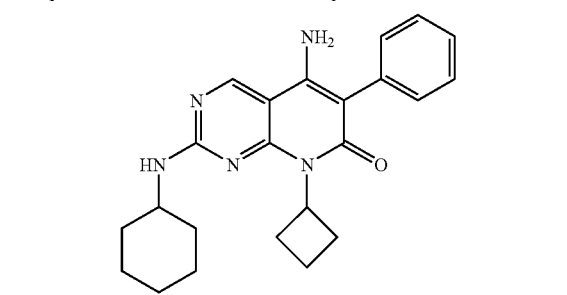
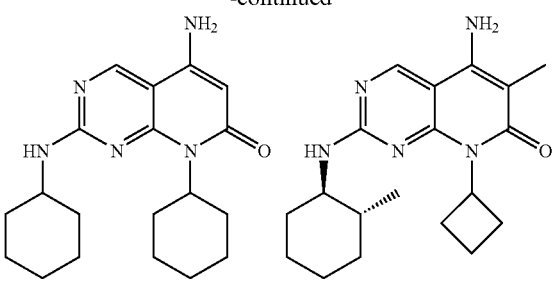
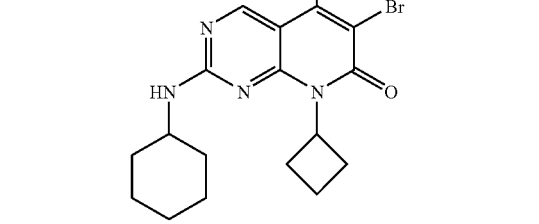
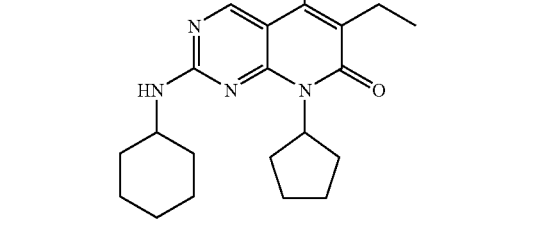
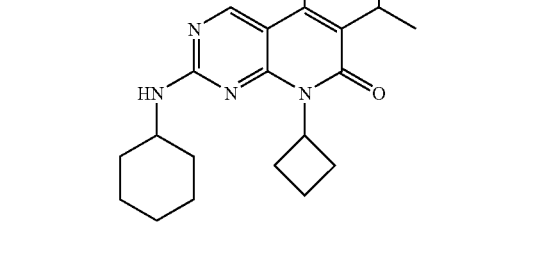
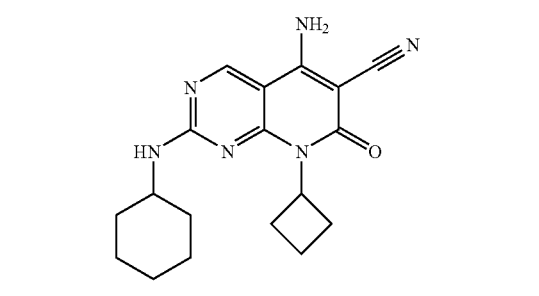
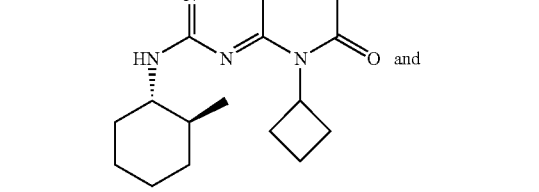

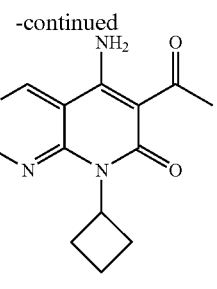

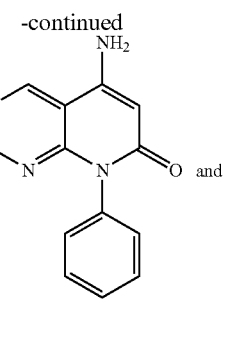

In certain embodiments, the compound is racemic 5-amino-2-cyclohexylamino-8-((1R/1S,3R/3S)-3-hydroxy-cyclopentyl)-8H-pyrido[2,3-d]pyrimidin-7-one.

In certain embodiments, $R^2$ is cycloalkyl.

In certain embodiments, the cycloalkyl is cyclobutyl.

In certain embodiments, m is 1.

In certain embodiments, $R^1$ is methyl.

In certain embodiments, $R^3$ is methyl.

In one embodiment, the compound is racemic 5-amino-8-cyclobutyl-6-methyl-2-((1R/1S,2S/2R)-(2-methyl-cyclohexylamino)-8H-pyrido[2,3-d]pyrimidin-7-one.

In one embodiment, the compound is racemic 5-amino-8-cyclobutyl-6-methyl-2-((1R/S,2R/2S)-2-methyl-cyclohexylamino)-8H-pyrido[2,3-d]pyrimidin-7-one.

In one embodiment, the compound is 5-amino-8-cyclobutyl-6-methyl-2-((1R,2R)-2-methyl-cyclohexylamino)-8H-pyrido[2,3-d]pyrimidin-7-one.

In one embodiment, the compound is 5-amino-8-cyclobutyl-6-methyl-2-((1S,2S)-2-methyl-cyclohexylamino)-8H-pyrido[2,3-d]pyrimidin-7-one In certain embodiments, $R^{5'}$ is $R^{5a}$ and $R^{5a}$ is —OH.

In certain embodiments, the compound is selected from the group consisting of:

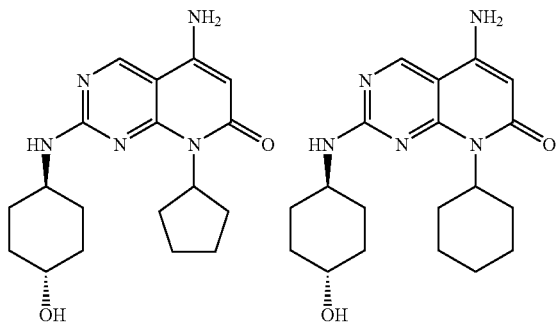

In certain embodiments, $R^{5'}$ is $R^{5a}$, $R^{5a}$ is A", A" is —NHC(=O)R$^7$ or —NHC(=O)OR$^7$, and $R^7$ is lower alkyl.

In certain embodiments, the compound is selected from the group consisting of:

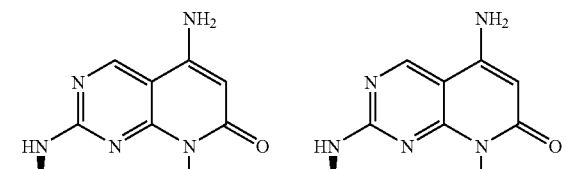

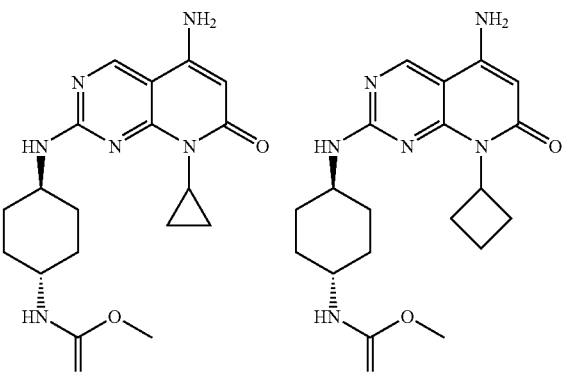

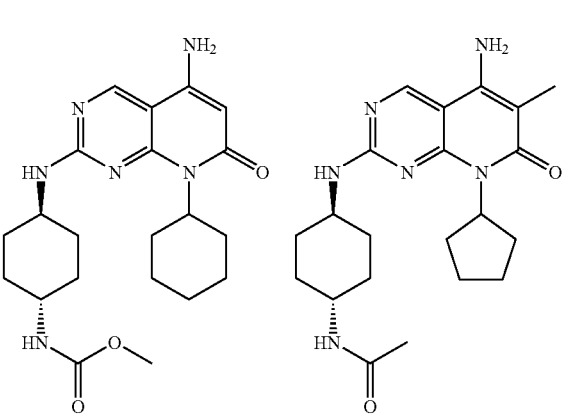

-continued
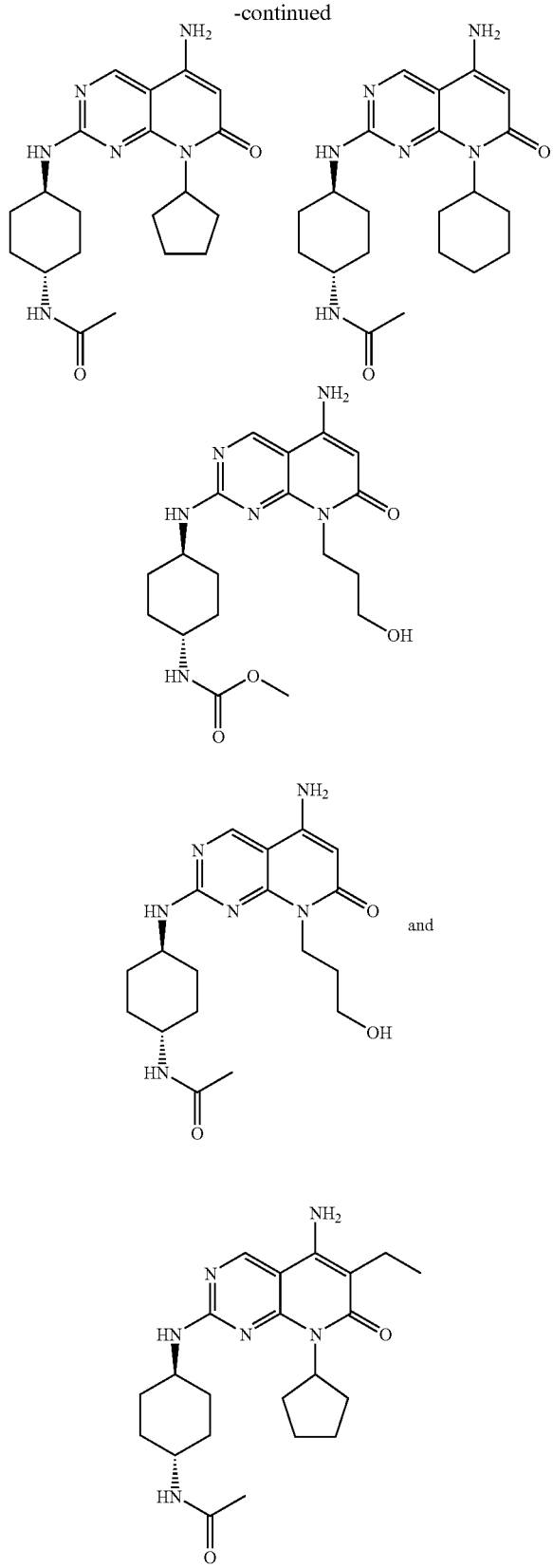
In one embodiment, the compound is racemic 2-(1-acetyl-piperidin-4-ylamino)-5-amino-8-((1R/1S,3R/3S)-3-hydroxy-cyclopentyl)-8H-pyrido[2,3-d]pyrimidin-7-one.
In certain embodiments, $R^{5'}$ is $R^{5a}$, $R^{5a}$ is A'', A'' is —C(=O)$R^8$, and $R^8$ is heterocycloalkyl.
In certain embodiments, the compound is selected from the group consisting of:
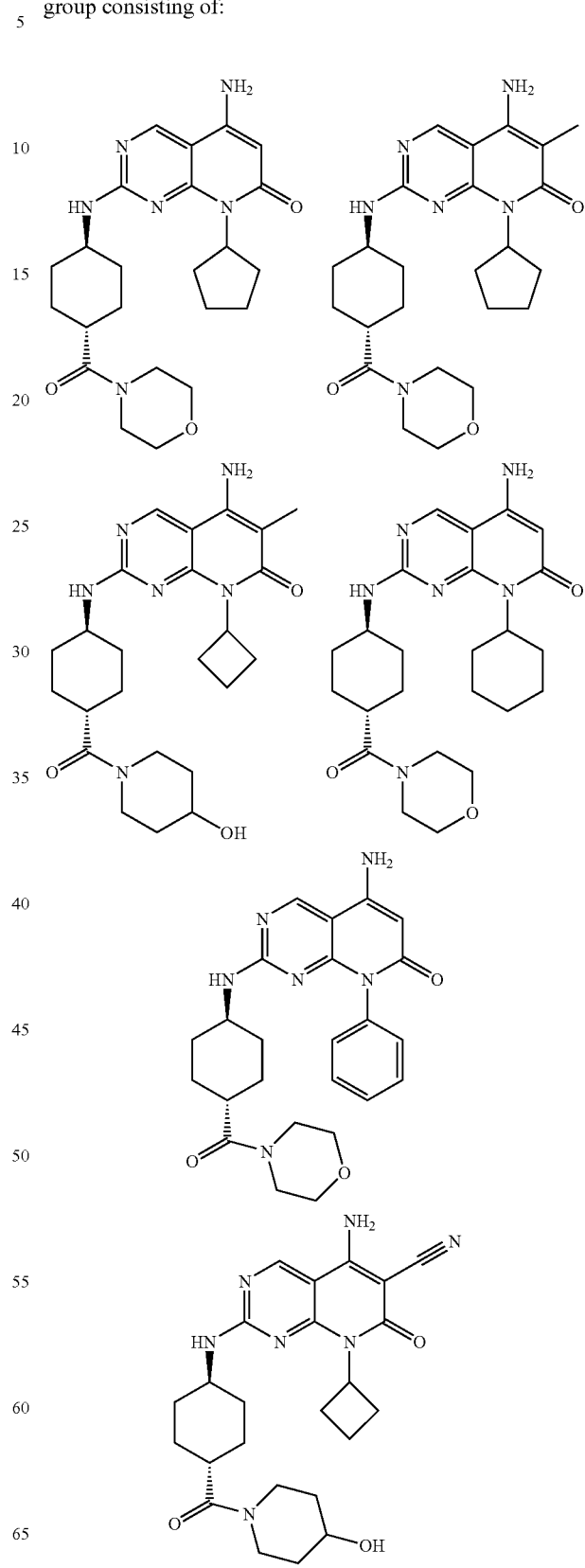

-continued
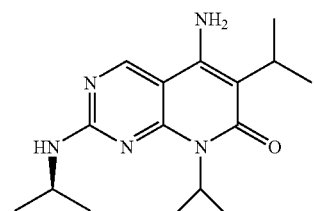
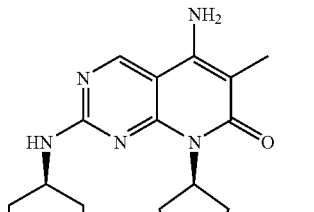
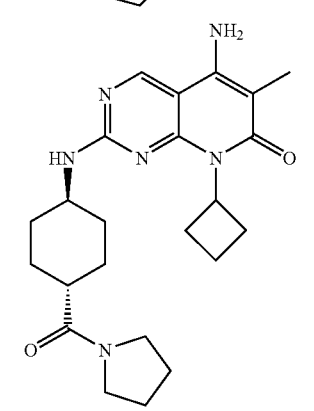
In certain embodiments, A is N(R$^{5b}$), R$^{5b}$ is A", A" is —S(=O)$_2$R$^7$, and R$^7$ is lower alkyl.
In certain embodiments, the compound is selected from the group consisting of:
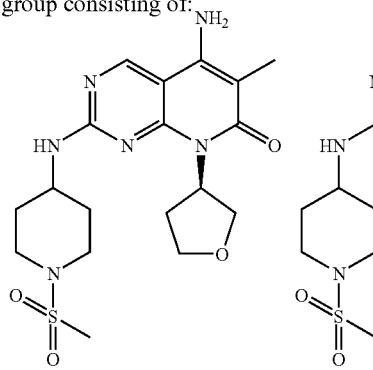 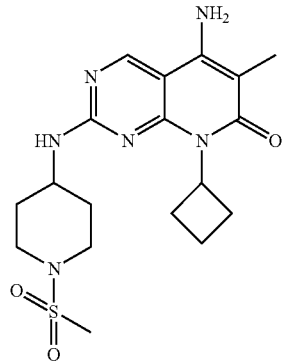
-continued
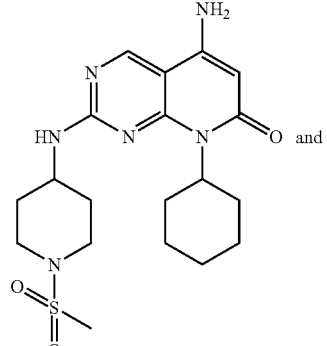 and
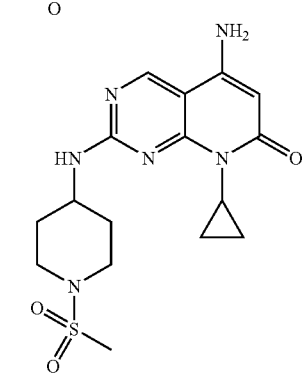
In certain embodiments, R$^{5'}$ is R$^{5a}$, R$^{5a}$ is A", A" is —NHS(=O)$_2$R$^7$, and R$^7$ is lower alkyl.
In certain embodiments, the compound is selected from the group consisting of:
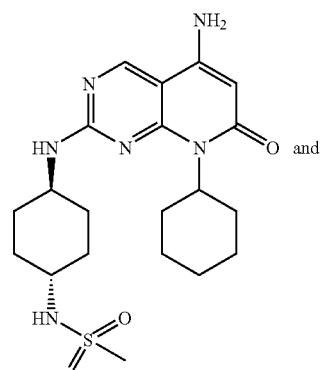 and
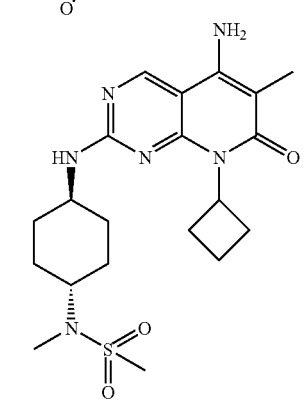

In certain embodiments, wherein A is O.

In certain embodiments, the compound is selected from the group consisting of:

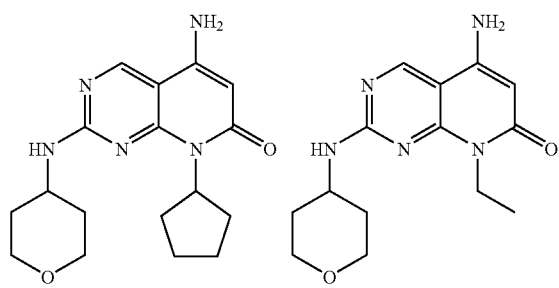

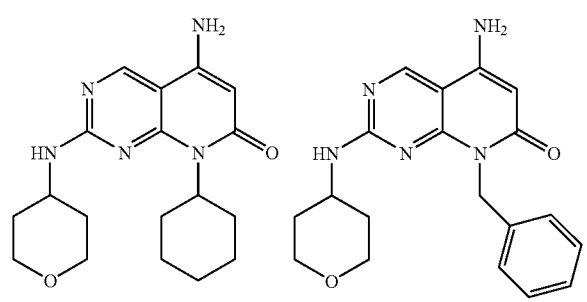

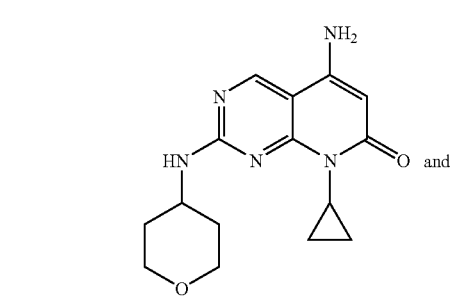

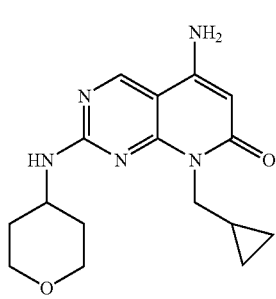

In certain embodiments, A is A', A' is N(R$^{5b}$), R$^{5b}$ is A", A" is —C(=O)R$^8$ or —C(=O)OR$^7$ and R$^7$ and R$^8$ are lower alkyl.

In certain embodiments, the compound is selected from the group consisting of:

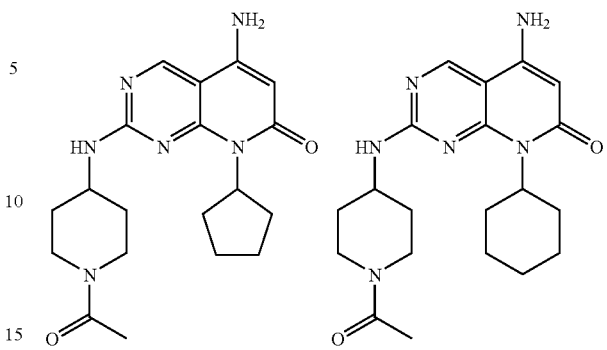

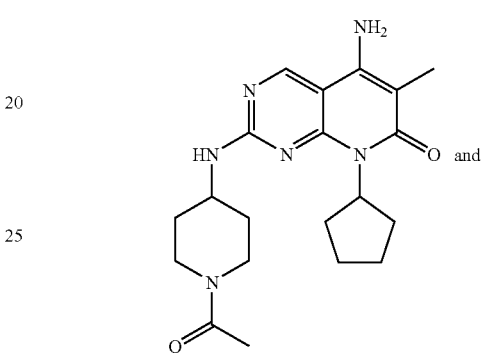

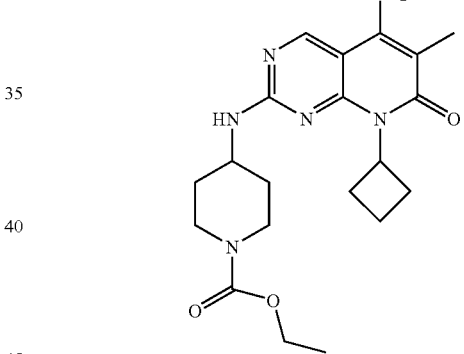

In one embodiment, the compound is racemic 2-(1-acetyl-piperidin-4-ylamino)-5-amino-8-((1R/1S,3R/3S)-3-hydroxy-cyclopentyl)-8H-pyrido[2,3-d]pyrimidin-7-one.

In certain embodiments, both R$^5$ and R$^{5'}$ are F.

In certain embodiments, the compound is selected from the group consisting of:

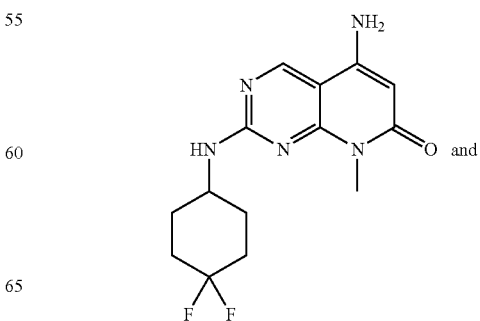

-continued

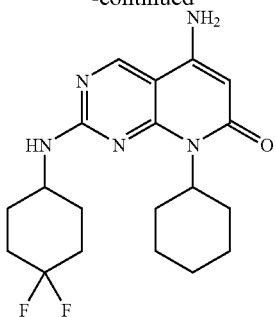

In certain embodiments, R⁵' is lower heteroalkyl.
In one embodiment, the compound is:

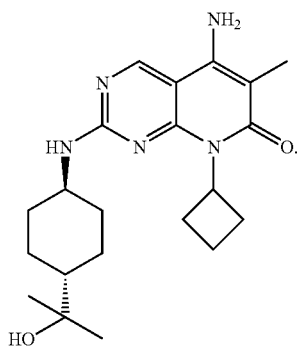

In one aspect, the application provides a compound of formula II

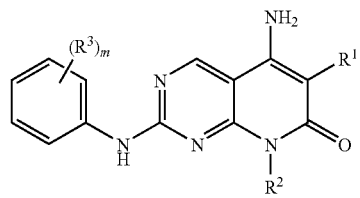
II including enantiomers, diastereomers, racemic mixtures and pharmaceutically acceptable salts thereof, wherein:
R¹ is R¹ᵃ or R¹ᵇ;
  R¹ᵃ is H, halo, lower alkyl, lower haloalkyl, lower alkoxy, —CN, or —OH;
  R¹ᵇ is cycloalkyl, heterocycloalkyl, or phenyl, optionally substituted with one or more R¹ᵇ';
    each R¹ᵇ' is independently halo, —OH, lower alkoxy, amino, lower alkyl or lower haloalkyl;
R² is lower alkyl, lower heteroalkyl, alkoxy, cycloalkyl, phenyl, heterocycloalkyl, or heteroaryl, optionally substituted with one or more R²ᵃ;
  each R²ᵃ is independently —OH, halo, lower alkyl, amino, lower alkoxy, or R²ᵇ;
    R²ᵇ is cycloalkyl, heterocycloalkyl, or phenyl, optionally substituted with one or more R²ᵇ';
      each R²ᵇ' is independently halo, —OH, lower alkoxy, amino, lower alkyl or lower haloalkyl;
R³ is H, halo, amino, lower alkyl, lower alkoxy, or lower haloalkyl; and
m is 0-5.

In certain embodiments, the compound is selected from the group consisting of:

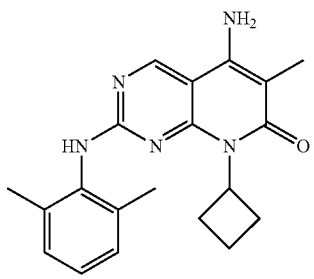

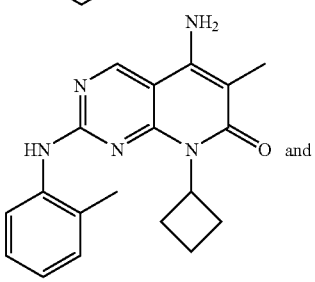
and

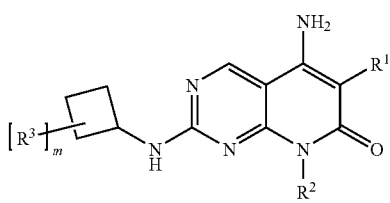

In one aspect, the application provides a compound of formula III

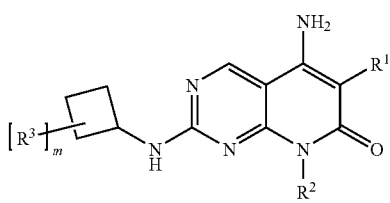
III including enantiomers, diastereomers, racemic mixtures and pharmaceutically acceptable salts thereof, wherein:
R¹ is R¹ᵃ or R¹ᵇ;
  R¹ᵃ is H, halo, lower alkyl, lower haloalkyl, lower alkoxy, —CN, or —OH;
  R¹ᵇ is cycloalkyl, heterocycloalkyl, or phenyl, optionally substituted with one or more R¹ᵇ';
    each R¹ᵇ' is independently halo, —OH, lower alkoxy, amino, lower alkyl or lower haloalkyl;
R² is lower alkyl, lower heteroalkyl, lower alkoxy, cycloalkyl, phenyl, heterocycloalkyl, or heteroaryl, optionally substituted with one or more R²ᵃ;
  each R²ᵃ is independently —OH, halo, lower alkyl, amino, lower alkoxy, or R²ᵇ;
    R²ᵇ is cycloalkyl, heterocycloalkyl, or phenyl, optionally substituted with one or more R²ᵇ';
      each R²ᵇ' is independently halo, —OH, lower alkoxy, amino, lower alkyl or lower haloalkyl;

R³ is halo, amino, lower alkyl, lower alkoxy, or lower haloalkyl; and m is 0 to 3.

In one embodiment, the compound has the structure:

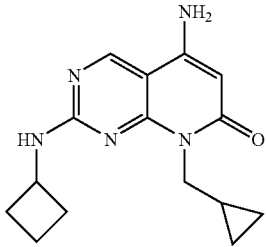

The application provides the compounds of the group consisting of:

5-Amino-2-cyclohexylamino-8-((1R,3R)-3-hydroxy-cyclopentyl)-8H-pyrido[2,3-d]pyrimidin-7-one;
[4-(5-Amino-8-cyclobutyl-7-oxo-7,8-dihydro-pyrido[2,3-d]pyrimidin-2-ylamino)-cyclohexyl]-carbamic acid methyl ester;
5-Amino-8-cyclobutyl-2-cyclohexylamino-8H-pyrido[2,3-d]pyrimidin-7-one;
5-Amino-8-cyclobutyl-2-cyclohexylamino-6-fluoro-8H-pyrido[2,3-d]pyrimidin-7-one;
5-Amino-8-cyclopentyl-2-(4-hydroxy-cyclohexylamino)-8H-pyrido[2,3-d]pyrimidin-7-one;
5-Amino-8-cyclohexyl-2-(4-hydroxy-cyclohexylamino)-8H-pyrido[2,3-d]pyrimidin-7-one;
5-Amino-8-cyclohexyl-2-[4-(morpholine-4-carbonyl)-cyclohexylamino]-8H-pyrido[2,3-d]pyrimidin-7-one;
5-Amino-2-cyclohexylamino-8-(3-hydroxy-propyl)-8H-pyrido[2,3-d]pyrimidin-7-one;
5-Amino-8-cyclobutyl-6-methyl-2-[4-(pyrrolidine-1-carbonyl)-cyclohexylamino]-8H-pyrido[2,3-d]pyrimidin-7-one;
5-Amino-8-cyclopentyl-6-methyl-2-[4-(morpholine-4-carbonyl)-cyclohexylamino]-8H-pyrido[2,3-d]pyrimidin-7-one;
N-[4-(5-Amino-8-cyclopentyl-7-oxo-7,8-dihydro-pyrido[2,3-d]pyrimidin-2-ylamino)-cyclohexyl]-acetamide;
5-Amino-2-cyclohexylamino-8-cyclopropylmethyl-8H-pyrido[2,3-d]pyrimidin-7-one;
5-Amino-8-cyclopentyl-2-[4-(morpholine-4-carbonyl)-cyclohexylamino]-8H-pyrido[2,3-d]pyrimidin-7-one;
N-[4-(5-Amino-8-cyclohexyl-7-oxo-7,8-dihydro-pyrido[2,3-d]pyrimidin-2-ylamino)-cyclohexyl]-methanesulfonamide;
5-Amino-8-cyclobutyl-2-[4-(4-hydroxy-piperidine-1-carbonyl)-cyclohexylamino]-6-methyl-8H-pyrido[2,3-d]pyrimidin-7-one;
5-Amino-6-(2-chloro-phenyl)-8-cyclobutyl-2-cyclohexylamino-8H-pyrido[2,3-d]pyrimidin-7-one;
5-Amino-2-cyclohexylamino-8-cyclopentyl-8H-pyrido[2,3-d]pyrimidin-7-one;
N-{4-[5-Amino-8-((1R,3R)-3-hydroxy-cyclopentyl)-7-oxo-7,8-dihydro-pyrido[2,3-d]pyrimidin-2-ylamino]-cyclohexyl}-acetamide;
[4-(5-Amino-8-cyclohexyl-7-oxo-7,8-dihydro-pyrido[2,3-d]pyrimidin-2-ylamino)-cyclohexyl]-carbamic acid methyl ester;
5-Amino-8-cyclobutyl-2-[4-(1-hydroxy-1-methyl-ethyl)-cyclohexylamino]-6-methyl-8H-pyrido[2,3-d]pyrimidin-7-one;
5-Amino-2-cyclohexylamino-8-ethyl-8H-pyrido[2,3-d]pyrimidin-7-one;
5-Amino-8-cyclopropyl-2-(4-hydroxy-cyclohexylamino)-8H-pyrido[2,3-d]pyrimidin-7-one;
N-[4-(5-Amino-8-cyclopentyl-6-ethyl-7-oxo-7,8-dihydro-pyrido[2,3-d]pyrimidin-2-ylamino)-cyclohexyl]-acetamide;
N-[4-(5-Amino-8-cyclobutyl-6-methyl-7-oxo-7,8-dihydro-pyrido[2,3-d]pyrimidin-2-ylamino)-cyclohexyl]-N-methyl-methanesulfonamide;
5-Amino-8-cyclobutyl-2-[4-(4-hydroxy-piperidine-1-carbonyl)-cyclohexylamino]-6-isopropyl-8H-pyrido[2,3-d]pyrimidin-7-one;
5-Amino-2-cyclohexylamino-8-cyclopropyl-8H-pyrido[2,3-d]pyrimidin-7-one;
5-Amino-8-cyclopropyl-2-(1-methanesulfonyl-piperidin-4-ylamino)-8H-pyrido[2,3-d]pyrimidin-7-one;
N-[4-(5-Amino-8-cyclohexyl-7-oxo-7,8-dihydro-pyrido[2,3-d]pyrimidin-2-ylamino)-cyclohexyl]-acetamide;
5-Amino-8-cyclohexyl-2-(1-methanesulfonyl-piperidin-4-ylamino)-8H-pyrido[2,3-d]pyrimidin-7-one;
2-(1-Acetyl-piperidin-4-ylamino)-5-amino-8-cyclopentyl-8H-pyrido[2,3-d]pyrimidin-7-one;
5-Amino-8-cyclobutyl-2-cyclohexylamino-6-phenyl-8H-pyrido[2,3-d]pyrimidin-7-one;
5-Amino-8-cyclohexyl-2-cyclohexylamino-8H-pyrido[2,3-d]pyrimidin-7-one;
5-Amino-8-cyclopentyl-2-(tetrahydro-pyran-4-ylamino)-8H-pyrido[2,3-d]pyrimidin-7-one;
5-Amino-8-cyclobutyl-6-methyl-2-((1R,2R)-2-methyl-cyclohexylamino)-8H-pyrido[2,3-d]pyrimidin-7-one;
5-Amino-6-bromo-8-cyclobutyl-2-cyclohexylamino-8H-pyrido[2,3-d]pyrimidin-7-on d]pyrimidin-7-one;
5-Amino-2-cyclohexylamino-8-cyclopentyl-6-ethyl-8H-pyrido[2,3-d]pyrimidin-7-one;
2-(1-Acetyl-piperidin-4-ylamino)-5-amino-8-((1R,3R)-3-hydroxy-cyclopentyl)-8H-pyrido[2,3-d]pyrimidin-7-one;
5-Amino-8-cyclobutyl-2-[4-(4-hydroxy-piperidine-1-carbonyl)-cyclohexylamino]-7-oxo-7,8-dihydro-pyrido[2,3-d]pyrimidine-6-carbonitrile;
[4-(5-Amino-8-cyclopropyl-7-oxo-7,8-dihydro-pyrido[2,3-d]pyrimidin-2-ylamino)-cyclohexyl]-carbamic acid methyl ester;
5-Amino-8-cyclobutyl-2-(1-methanesulfonyl-piperidin-4-ylamino)-6-methyl-8H-pyrido[2,3-d]pyrimidin-7-one;
N-[4-(5-Amino-8-cyclopentyl-6-methyl-7-oxo-7,8-dihydro-pyrido[2,3-d]pyrimidin-2-ylamino)-cyclohexyl]-acetamide;
N-{4-[5-Amino-8-(3-hydroxy-propyl)-7-oxo-7,8-dihydro-pyrido[2,3-d]pyrimidin-2-ylamino]-cyclohexyl}-acetamide;
{4-[5-Amino-8-(3-hydroxy-propyl)-7-oxo-7,8-dihydro-pyrido[2,3-d]pyrimidin-2-ylamino]-cyclohexyl}-carbamic acid methyl ester;
5-Amino-2-cyclohexylamino-6-methyl-8-(R)-tetrahydro-furan-3-yl-8H-pyrido[2,3-d]pyrimidin-7-one;
5-Amino-8-cyclopentyl-2-phenylamino-8H-pyrido[2,3-d]pyrimidin-7-one;
5-Amino-8-cyclopropylmethyl-2-(tetrahydro-pyran-4-ylamino)-8H-pyrido[2,3-d]pyrimidin-7-one;
5-Amino-2-[4-(4-hydroxy-piperidine-1-carbonyl)-cyclohexylamino]-6-methyl-8-(R)-tetrahydro-furan-3-yl-8H-pyrido[2,3-d]pyrimidin-7-one;
5-Amino-2-(4-hydroxy-cyclohexylamino)-8-methyl-8H-pyrido[2,3-d]pyrimidin-7-one;
5-Amino-8-cyclobutyl-2-cyclohexylamino-6-isopropyl-8H-pyrido[2,3-d]pyrimidin-7-one;

5-Amino-8-ethyl-2-(tetrahydro-pyran-4-ylamino)-8H-pyrido[2,3-d]pyrimidin-7-one;
5-Amino-8-cyclohexyl-2-(tetrahydro-pyran-4-ylamino)-8H-pyrido[2,3-d]pyrimidin-7-one;
5-Amino-8-cyclobutyl-2-cyclohexylamino-7-oxo-7,8-dihydro-pyrido[2,3-d]pyrimidine-6-carbonitrile;
5-Amino-2-(1-methanesulfonyl-piperidin-4-ylamino)-6-methyl-8-(R)-tetrahydro-furan-3-yl-8H-pyrido[2,3-d]pyrimidin-7-one;
5-Amino-8-cyclopropyl-2-(tetrahydro-pyran-4-ylamino)-8H-pyrido[2,3-d]pyrimidin-7-one;
5-Amino-2-cyclobutylamino-8-cyclopropylmethyl-8H-pyrido[2,3-d]pyrimidin-7-one;
4-(5-Amino-8-cyclobutyl-6-methyl-7-oxo-7,8-dihydro-pyrido[2,3-d]pyrimidin-2-ylamino)-piperidine-1-carboxylic acid ethyl ester;
5-Amino-8-cyclohexyl-2-(4,4-difluoro-cyclohexylamino)-8H-pyrido[2,3-d]pyrimidin-7-one;
5-Amino-8-cyclobutyl-6-methyl-2-((1R,2S)-2-methyl-cyclohexylamino)-8H-pyrido[2,3-d]pyrimidin-7-one;
2-(1-Acetyl-piperidin-4-ylamino)-5-amino-8-cyclopentyl-6-methyl-8H-pyrido[2,3-d]pyrimidin-7-one;
5-Amino-8-cyclobutyl-6-methyl-2-((1S,2S)-2-methyl-cyclohexylamino)-8H-pyrido[2,3-d]pyrimidin-7-one;
2-(1-Acetyl-piperidin-4-ylamino)-5-amino-8-cyclohexyl-8H-pyrido[2,3-d]pyrimidin-7-one;
5-Amino-8-cyclobutyl-6-methyl-2-o-tolylamino-8H-pyrido[2,3-d]pyrimidin-7-one;
5-Amino-2-cyclohexylamino-8-phenyl-8H-pyrido[2,3-d]pyrimidin-7-one;
5-Amino-2-[4-(morpholine-4-carbonyl)-cyclohexylamino]-8-phenyl-8H-pyrido[2,3-d]pyrimidin-7-one;
5-Amino-2-(4,4-difluoro-cyclohexylamino)-8-methyl-8H-pyrido[2,3-d]pyrimidin-7-one;
5-Amino-8-benzyl-2-cyclohexylamino-8H-pyrido[2,3-d]pyrimidin-7-one;
5-Amino-2-(4-hydroxy-cyclohexylamino)-8-phenyl-8H-pyrido[2,3-d]pyrimidin-7-one;
6-Acetyl-5-amino-8-cyclobutyl-2-cyclohexylamino-8H-pyrido[2,3-d]pyrimidin-7-one;
5-Amino-8-benzyl-2-(tetrahydro-pyran-4-ylamino)-8H-pyrido[2,3-d]pyrimidin-7-one; and
5-Amino-8-cyclobutyl-2-(2,6-dimethyl-phenylamino)-6-methyl-8H-pyrido[2,3-d]pyrimidin-7-one.

In one aspect, the application provides a method of treating a JNK-mediated disorder in a subject having a JNK-mediated disorder, said method comprising administering to a subject in need thereof a therapeutically effective amount of any of the above compounds.

In certain embodiments of the method of treating a JNK-mediated disorder, the JNK-mediated disorder is characterized by cellular proliferation.

In certain embodiments of the method of treating a JNK-mediated disorder, the JNK-mediated disorder is arthritis.

In certain embodiments of the method of treating a JNK-mediated disorder, the arthritis is rheumatoid arthritis.

In certain embodiments of the method of treating a JNK-mediated disorder, the JNK-mediated disorder is asthma.

In certain embodiments of the method of treating a JNK-mediated disorder, the JNK-mediated disorder is diabetes.

In certain embodiments of the method of treating a JNK-mediated disorder, the JNK-mediated disorder is Alzheimer's disease.

In certain embodiments of the method of treating a JNK-mediated disorder, the JNK-mediated disorder is Parkinson's disease.

In certain embodiments of the method of treating a JNK-mediated disorder, the JNK-mediated disorder is ischemic stroke.

In certain embodiments of the method of treating a JNK-mediated disorder, the JNK-mediated disorder is cancer.

In certain embodiments of the method for treating a JNK-mediated disorder, wherein the JNK-mediated disorder is cancer, the cancer is brain cancer.

In certain embodiments of the method for treating a JNK-mediated disorder, wherein the JNK-mediated disorder is cancer, the cancer is leukemia.

In one aspect, the application provides a pharmaceutical composition comprising the compound of any one of the above embodiments, admixed with at least one pharmaceutically acceptable carrier, excipient or diluent.

DETAILED DESCRIPTION OF THE INVENTION

All publications cited in this disclosure are incorporated herein by reference in their entirety.

DEFINITIONS

Unless otherwise stated, the following terms used in this application, including the specification and claims, have the definitions given below. It must be noted that, as used in the specification and the appended claims, the singular forms "a", "an," and "the" include plural referents unless the context clearly dictates otherwise. Thus, the phrase "'a' or 'an' entity' as used herein refers to one or more of that entity; for example, a compound refers to one or more compounds or at least one compound. As such, the terms "a" (or "an"), "one or more", and "at least one" can be used interchangeably herein.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., m, n, R, $R^1$, $R^2$, $R^{2a}$, $R^{2b}$, $R^3$, $R^4$, $R^5$, $R^{5a}$, $R^6$, $R^{6a}$, $R^7$, $R^8$, $R^9$, A, A' and A") occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or " ------ " drawn through a bond each refer to the point of attachment of a functional group or other chemical moiety to the rest of the molecule of which it is a part. Thus, for example:

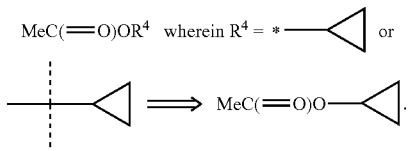

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The phrase "optional bond" means that the bond may or may not be present, and that the description includes single, double, or triple bonds. If a substituent is designated to be a "bond" or "absent", the atoms linked to the substituents are then directly connected.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Certain compounds of the invention may exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl refers to a group —C(=O)R contain 6 carbon atoms. The term "arylcarbonyl" as used herein means a group of formula C(=O)R wherein R is an aryl group; the term "benzoyl" as used herein an "arylcarbonyl" group wherein R is phenyl.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical.

The term "alkylene" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —CH$_2$CH (i-Pr)CH$_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The term "alkoxyalkyl" as used herein refers to the radical R'R"—, wherein R' is an alkoxy radical as defined herein, and R" is an alkylene radical as defined herein with the understanding that the attachment point of the alkoxyalkyl moiety will be on the alkylene radical. $C_{1-6}$ alkoxyalkyl denotes a group wherein the alkyl portion is comprised of 1-6 carbon atoms exclusive of carbon atoms in the alkoxy portion of the group. $C_{1-3}$ alkoxy-$C_{1-6}$ alkyl denotes a group wherein the alkyl portion is comprised of 1-6 carbon atoms and the alkoxy group is 1-3 carbons. Examples are methoxymethyl, methoxyethyl, methoxypropyl, ethoxymethyl, ethoxyethyl, ethoxypropyl, propyloxypropyl, methoxybutyl, ethoxybutyl, propyloxybutyl, butyloxybutyl, t-butyloxybutyl, methoxypentyl, ethoxypentyl, propyloxypentyl including their isomers.

The term "alkylthio" or "alkylsulfanyl" refers to an —S-alkyl group, wherein alkyl is as defined above such as meththio, ethylthio, n-propylthio, i-propylthio, n-butylthio, hexylthio, including their isomers. "Lower alkylthio" as used herein denotes an alkylthio group with a "lower alkyl" group as previously defined. "$C_{1-10}$ alkylthio" as used herein refers to an —S-alkyl wherein alkyl is $C_{1-10}$. "Phenylthio" is an "arylthio" moiety wherein aryl is phenyl.

The terms "alkylcarbonylamino" and "arylcarbonylamino" as used herein refers to a group of formula —NC(=O)R wherein R is alkyl or aryl respectively and alkyl and aryl are as defined herein.

The terms "alkylsulfinyl" and "arylsulfinyl" as used herein refers to a group of formula —S(=O)R wherein R is alkyl or aryl respectively and alkyl and aryl are as defined herein The terms "alkylsulfonyl" and "arylsulfonyl" as used herein refers to a group of formula —S(=O)$_2$R wherein R is alkyl or aryl respectively and alkyl and aryl are as defined herein. The term "heteroalkylsulfonyl" as used herein refers herein denotes a group of formula —S(=O)$_2$R wherein R is "heteroalkyl" as defined herein.

The terms "alkylsulfonylamino" and "arylsulfonylamino" as used herein refers to a group of formula —NR'S(=O)$_2$R wherein R is alkyl or aryl respectively, R' is hydrogen or $C_{1-3}$ alkyl, and alkyl and aryl are as defined herein.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxy-phenyl, and the like, including partially hydrogenated derivatives thereof.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkyl-amino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Cycloalkylalkyl" mean a moiety of the formula —$R^a$—$R^b$, where $R^a$ is alkylene and $R^b$ is cycloalkyl as defined herein.

The term "heteroalkoxy" as used herein means an —O-(heteroalkyl) group wherein heteroalkyl is defined herein. $C_{1-10}$ heteroalkoxy" as used herein refers to an —O-(heteroalkyl) wherein alkyl is $C_{1-10}$. Representative examples include, but are not limited to, 2-dimethylaminoethoxy and 3-sulfonamido-1-propoxy.

The term "heteroalkyl" as used herein refers to an alkyl radical as defined herein wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, or alkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

The term "heteroaryl" or "heteroaromatic" as used herein means a monocyclic or bicyclic radical of 5 to 12 ring atoms having at least one aromatic ring containing four to eight atoms per ring, incorporating one or more N, O, or S heteroatoms, the remaining ring atoms being carbon, with the understanding that the attachment point of the heteroaryl radical will be on an aromatic ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, pyrrolyl, pyrazolyl, imidazolyl, oxazol, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole and benzisothiazole. Bicyclic moieties can be optionally substituted on either ring; however the point of attachment is on a ring containing a heteroatom.

The term "heterocyclyl", "heterocycle", or "heterocycloalkyl" as used herein denotes a monovalent saturated cyclic radical, consisting of one or more rings, preferably one to two rings, of three to eight atoms per ring, incorporating one or more ring heteroatoms (chosen from N, O or $S(O)_{0-2}$), and which can optionally be independently substituted with one or more, preferably one or two substituents selected from hydroxy, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, unless otherwise indicated. Examples of heterocyclic radicals include, but are not limited to, azetidinyl, pyrrolidinyl, hexahydroazepinyl, oxetanyl, tetrahydrofuranyl, tetrahydrothiophenyl, oxazolidinyl, thiazolidinyl, isoxazolidinyl, morpholinyl, piperazinyl, piperidinyl, tetrahydropyranyl, thiomorpholinyl, quinuclidinyl and imidazolinyl.

The term "hydroxyalkyl" as used herein denotes an alkyl radical as herein defined wherein one to three hydrogen atoms on different carbon atoms is/are replaced by hydroxyl groups.

Commonly used abbreviations include: acetyl (Ac), azo-bis-isobutyrylnitrile (AIBN), atmospheres (Atm), 9-borabicyclo[3.3.1]nonane (9-BBN or BBN), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N, N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether ($Et_2O$), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), lithium hexamethyl disilazane (LiHMDS), methanol (MeOH), melting point (mp), $MeSO_2$— (mesyl or Ms), methyl (Me), acetonitrile (MeCN), m-chloroperbenzoic acid (MCPBA), mass spectrum (ms), methyl t-butyl ether (MTBE), N-bromosuccinimide (NBS), N-carboxyanhydride (NCA), N-chlorosuccinimide (NCS), N-methylmorpholine (NMM), N-methylpyrrolidone (NMP), pyridinium chlorochromate (PCC), pyridinium dichromate (PDC), phenyl (Ph), propyl (Pr), iso-propyl (i-Pr), pounds per square inch (psi), pyridine (pyr), room temperature (rt or RT), tert-butyldimethylsilyl or t-$BuMe_2Si$ (TBDMS), triethylamine (TEA or $Et_3N$), 2,2,6,6-tetramethylpiperidine 1-oxyl (TEMPO), triflate or $CF_3SO_2$— (Tf), trifluoroacetic acid (TFA), 1,1'-bis-2,2,6,6-tetramethylheptane-2,6-dione (TMHD), O-benzotriazol-1-yl-N,N,N',N'-tetramethyluronium tetrafluoroborate (TBTU), thin layer chromatography (TLC), tetrahydrofuran (THF), trimethylsilyl or $Me_3Si$ (TMS), p-toluenesulfonic acid monohydrate (TsOH or pTsOH), 4-Me-$C_6H_4SO_2$— or tosyl (Ts), N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

"Heteroalkyl" means an alkyl moiety as defined herein, including a branched $C_4$-$C_7$ alkyl, wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl; when n is 1, $R^d$ is alkyl, cycloalkyl, or cycloalkylalkyl; and when n is 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-amino-ethyl, 3-aminopropyl, 2-methylsulfonylethyl, aminosulfonylmethyl, aminosulfonylethyl, amino-sulfonylpropyl, methylaminosulfonylmethyl, methylaminosulfonylethyl, methylaminosulfonyl-propyl, and the like.

"Heteroaryl" means a monocyclic or bicyclic moiety of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, thiophenyl, furanyl, pyranyl, pyridinyl, pyrrolyl, pyrazolyl, pyrimidyl, pyridazinyl, quinolinyl, isoquinolinyl, benzofuryl, benzofuranyl, benzothiophenyl, benzothiopyranyl, benzimidazolyl, benzoxazolyl, benzooxadiazolyl, benzothiazolyl, benzothiadiazolyl, benzopyranyl, indolyl, isoindolyl, indazolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

The terms "halo," "halogen," and "halide" are used interchangeably herein and refer to fluoro, chloro, bromo, and iodo.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, —$CF_2CF_3$, —$CF_3$, and the like.

"Heterocyclyl" or "heterocycloalkyl" means a monovalent saturated moiety, consisting of one to two rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydroisoquinolinyl, tetrahydroquinolinyl, tetrahydroisoquinolinyl, and the like.

"Optionally substituted" means a substituent which is substituted independently with zero to three substituents selected from lower alkyl, halo, OH, cyano, amino, nitro, lower alkoxy, or halo-lower alkyl.

"Leaving group" means a group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzene-sulfonyloxy, tosyloxy, and thienyloxy, dihalophosphinoyloxy, optionally substituted benzyloxy, isopropyloxy, acyloxy, and the like.

"Optional" or "optionally" means that the subsequently described event or circumstance may but need not occur, and that the description includes instances where the event or circumstance occurs and instances in which it does not.

"Agonist" refers to a compound that enhances the activity of another compound or receptor site.

"Antagonist" refers to a compound that diminishes or prevents the action of another compound or receptor site.

The term "drug candidate" refers to a compound or preparation which is to be tested for possible effect in the treatment of a disease state in an animal, regardless of whether said drug candidate has any known biological activity.

The term "homologous" as used herein refers to a protein that performs substantially the same function in another subject species and shares substantial sequence identity, to the extent that they are recognized in the art as being different versions of the same protein, differing primarily in the species in which they are found. Thus, for example, human ERG, mouse ERG, and rat ERG are all considered homologous to each other.

"Modulator" means a molecule that interacts with a target. The interactions include, but are not limited to, agonist, antagonist, and the like, as defined herein.

"Disease" and "Disease state" means any disease, condition, symptom, disorder or indication.

The term "cell line" refers to a clone of immortalized mammalian cells. A "stable" cell line is a cell line that exhibits substantially consistent characteristics over time (e.g., with each doubling). A stable cell line within the scope of this invention provides a substantial proportion of cells that are capable of providing a seal resistance of greater than about 50 MOhm, a current amplitude of greater than about 200 pA, and provide a current amplitude that does not vary by more than approximately 20% over one hour under control conditions.

"Pharmaceutically acceptable salts" of a compound means salts that are pharmaceutically acceptable, as defined herein, and that possess the desired pharmacological activity of the parent compound. Such salts include:

(1) acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or (2) salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

It should be understood that all references to pharmaceutically acceptable salts include solvent addition forms (solvates) or crystal forms (polymorphs) as defined herein, of the same acid addition salt.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" includes mammals and birds. "Mammals" means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgement of the attending medical or veterinary practitioner, and other factors.

"Pharmacological effect" as used herein encompasses effects produced in the subject that achieve the intended purpose of a therapy. For example, a pharmacological effect would be one that results in the prevention, alleviation or reduction of urinary incontinence in a treated subject.

"Disease state" means any disease, condition, symptom, or indication.

"Treating" or "treatment" of a disease state includes (i) preventing the disease state, i.e. causing the clinical symptoms of the disease state not to develop in a subject that may be exposed to or predisposed to the disease state, but does not yet experience or display symptoms of the disease state; (ii) inhibiting the disease state, i.e., arresting the development of the disease state or its clinical symptoms; or (iii) relieving the disease state, i.e., causing temporary or permanent regression of the disease state or its clinical symptoms.

All patents and publications identified herein are incorporated herein by reference in their entirety.

COMPOUNDS AND PREPARATION

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

General Method

The invention provides compounds and compositions for treating inflammatory disorders, and methods of treating disorders mediated by JNK.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reaction described herein preferably are conducted under inert atmosphere, at atmospheric pressure, at a reaction temperature range of from about −78° C. to about 180° C., and most preferably and conveniently at room (or ambient) temperature, e.g., about 20° C.

In the following schemes are depicted some of the possible synthetic routes leading to the compounds object of the invention. The radicals $R^1$, $R^2$, $R^3$, $R^5$, $R^6$, and $R^7$ are as defined above unless specified otherwise.

dine-5-carbonitrile can firstly be alkylated in the same manner as described in Step B and then can be acylated by treatment with methyl magnesium bromide and acetic anhydride in a apolar aprotic solvent such as toluene (Step D and Step E). The amide of generic formula I can cyclize to form the corresponding 5-amino-8H-pyrido[2,3-d]pyrimidin-7-one in the presence of a strong base such as lithium bis(trimethylsilyl)amide in a polar solvent such as THF as shown in Step C.

SCHEME II

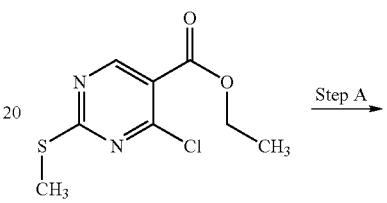

SCHEME I

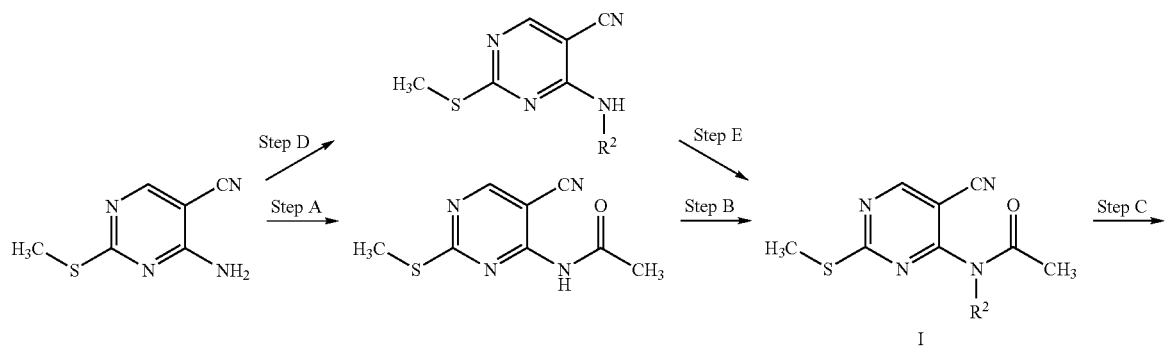

Step A: $Ac_2O$, Pyridine, 80° C.;
Step B: NaH, $R^2X$, DMSO;
Step C: LiHMDS, THF;
Step D: NaH, $R^2X$, DMSO, 50° C.;
Step E: MeMgBr, $Ac_2O$, Toluene, Reflux.

In Step A 4-amino-2-methylsulfanyl-pyrimidine-5-carbonitrile can be acetylated by heating at about 80° C. in presence of acetic anhydride and pyridine. The acetyl amide formed in this way can be alkylated in the presence of a strong inorganic base such as sodium hydride and an alkylating agent such as methyl iodide in a polar solvent such as DMSO, as described in Step B. Alternatively 4-amino-2-methylsulfanyl-pyrimi- -continued

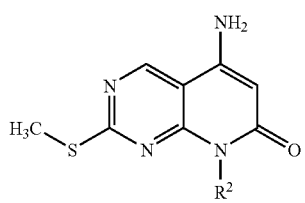

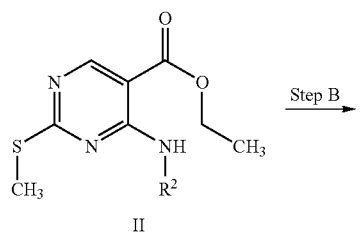

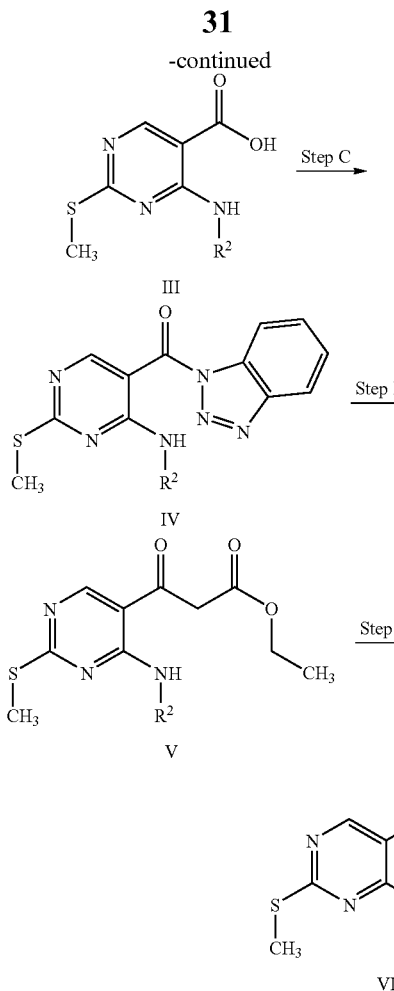

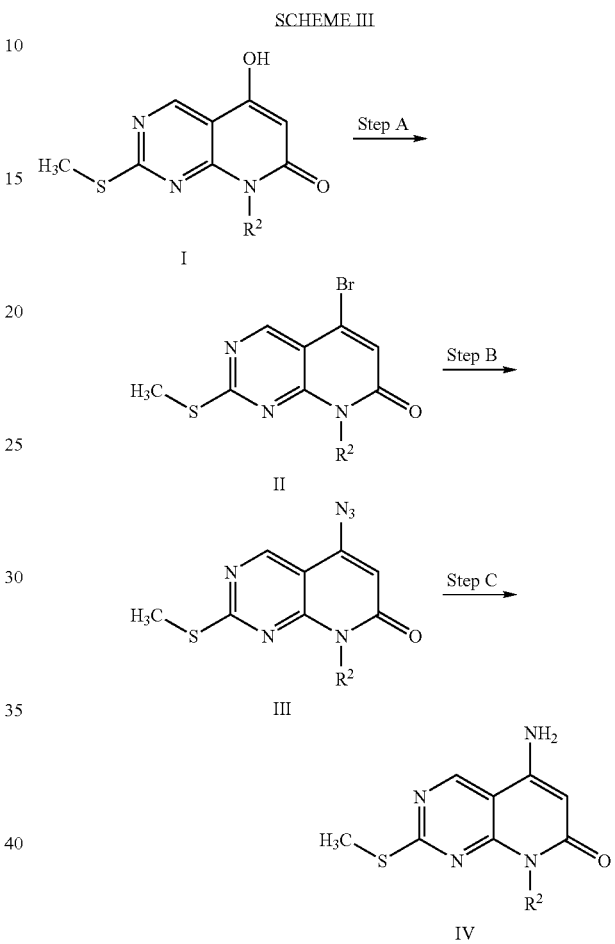

decarboxylated by heating at reflux in presence of TFA to give the malonate V. The malonate V, by heating in the presence of 2 strong organic bases such as DIEPA and DBU, can be converted in the corresponding 5-hydroxy-2-methylsulfanyl-8H-pyrido[2,3-d]pyrimidin-7-one VI as showed in Step E.

Step A: R²NH₂, DCM;
Step B: NaOH, EtOH, Reflux;
Step C: Benzotriazole, EDCI, DCM;
Step D: LDA, EtOAc, THF, −78° C.; or 1) NaH, t-BuOCOCH₂COOEt, DMF, 0° C., 2) TFA, Reflux;
Step E: DIPEA, DBU, Heat In Step A, 4-chloro-2-methylsulfanyl-pyrimidine-5-carboxylic acid ethyl ester undergoes an $S_NAr$ reaction with an appropriate primary amine R²NH₂ in an apolar solvent such as DCM, to give the corresponding aniline of general formula II. Aniline II can then be hydrolyzed to the corresponding acid III by heating in a polar protic solvent, such as EtOH at reflux, in presence of water and a strong inorganic base such as NaOH. The acid III can be converted to the corresponding activated ester IV by reacting with benzotriazole in an apolar solvent such as DCM in presence of a coupling agent such as EDCI, as described in Step C. The activated ester IV can be converted to the corresponding malonate V by reaction, at −78° C., in a polar aprotic solvent such as tetrahydrofuran, with the lithium enolate of ethyl acetate generated in situ with lithium diisopropylamide as illustrated in Step D. Alternatively IV can react with tert-butyl ethyl malonate at 0° C. in presence of a strong base such as NaH in a polar solvent such as DMF, and the coupled product can then be hydrolyzed and Step A: POBr₃, DCE, 100° C.;
Step B: NaN₃, DMF, 90° C., MW;
Step C: PPh₃, THF, 35° C. or H₂, Pd(OH)₂/C, AcOH.

In Step A, the 5-hydroxy-2-methylsulfanyl-8H-pyrido[2,3-d]pyrimidin-7-one of formula I can be brominated by heating under microwave conditions at 100° C. with phosphorus oxybromide in an apolar solvent such as dichloroethane. The bromide of formula II can undergo an $S_N$ reaction by heating under microwave conditions at 90° C. with sodium azide in a polar solvent such as DMF, as described in Step B. The azide of formula III can then be reduced to the corresponding amine IV, Step C, by reaction with a reducing agent such as triphenylphosphine at 35° C. in a polar solvent such as THF in presence of aqueous HCl. Alternatively, the azide III can be reduced by hydrogenation using a catalyst such as palladium hydroxide on carbon and a polar protic solvent such as acetic acid.

SCHEME IV

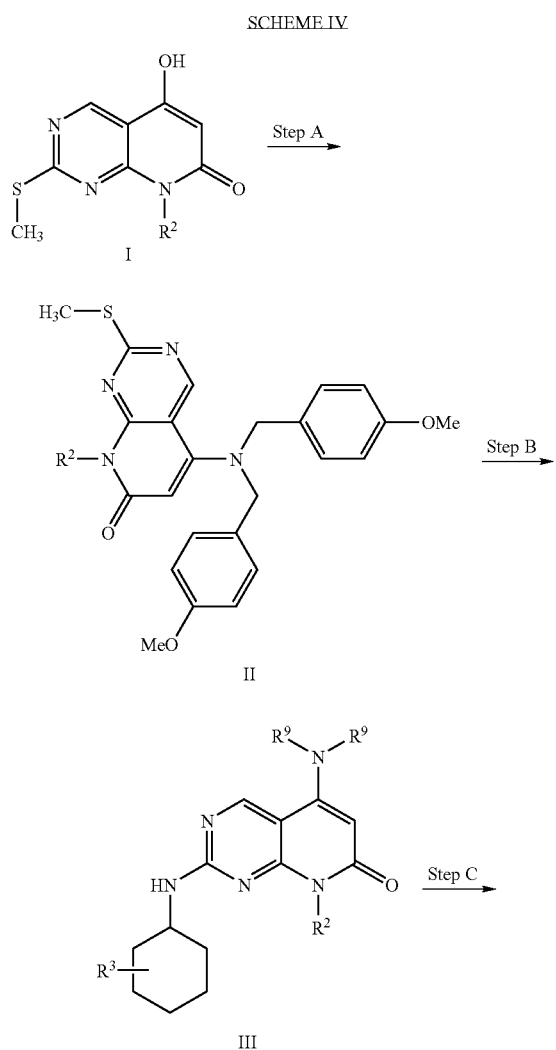

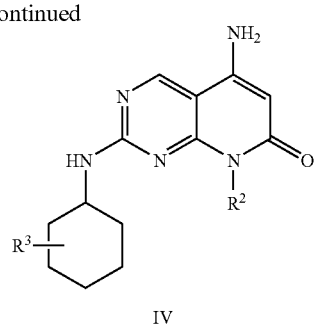

$R^9$ is PMB or H.

Step A: 1) Tf$_2$O, TEA, DCM, −78° C.; 2) NH(PMB)$_2$, 100° C., MW;

Step B: 1) OXONE™, acetone/water or m-CPBA, CH2Cl2; 2) Base, R$^1$R$^4$Cy, heating;

Step C: HClO$_4$, DCM.

In Step A, the 5-hydroxy-2-methylsulfanyl-8H-pyrido[2,3-d]pyrimidin-7-one of formula I can react with trifluoromethanesulfonic anhydride, at −78° C., in an apolar solvent such as DCM, in the presence of an organic base such as Et$_3$N, and the leaving group can then be displaced by reaction with bis-(4-methoxybenzyl)-amine by heating at 100° C. under microwave conditions to give the amine of general formula II. The thiomethyl moiety of compound of generic formula II can be oxidized by reaction with oxidizers such as OXONE™ in a mixture of acetone and water or with 3-chloroperoxybenzoic acid in DCM to give the corresponding sulfone or sulfoxide, or a mixture of the above. The leaving group created in this way can then be displaced by a substituted cyclohexylamine by heating in THF, with or without a base such as Et$_3$N or DIPEA, as described in Step B. The amine of generic formula III, when R$^9$ is PMB, can then be deprotected as shown in Step C, by reaction with perchloric acid in DCM.

TABLE X

| # | | Structure | MS | MP |
|---|---|---|---|---|
| I-1 | 5-Amino-2-cyclohexylamino-8-((1R,3R)-3-hydroxy-cyclopentyl)-8H-pyrido[2,3-d]pyrimidin-7-one (racemic) | 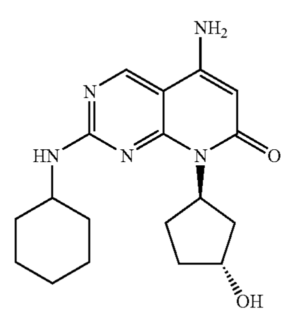 | 343.43 | 169.5-170.0 |

TABLE X-continued

| # | | Structure | MS | MP |
|---|---|---|---|---|
| I-2 | [4-(5-Amino-8-cyclobutyl-7-oxo-7,8-dihydro-pyrido[2,3-d]pyrimidin-2-ylamino)-cyclohexyl]-carbamic acid methyl ester | 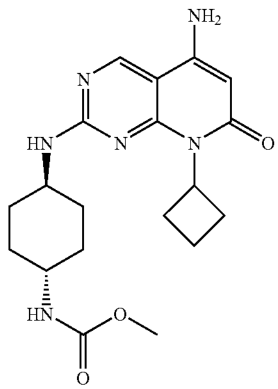 | 386.45 | 154.3-156.0 |
| I-3 | 5-Amino-8-cyclobutyl-2-cyclohexylamino-8H-pyrido[2,3-d]pyrimidin-7-one | 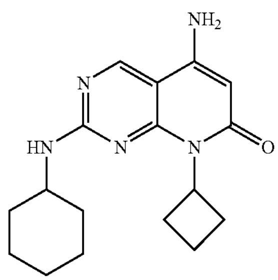 | 313.4 | 120.0-121.5 |
| I-4 | 5-Amino-8-cyclobutyl-2-cyclohexylamino-6-fluoro-8H-pyrido[2,3-d]pyrimidin-7-one | 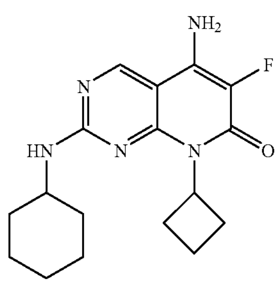 | 331.39 | 286.0-287.0 |
| I-5 | 5-Amino-8-cyclopentyl-2-(4-hydroxy-cyclohexylamino)-8H-pyrido[2,3-d]pyrimidin-7-one | 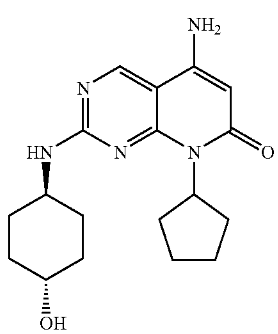 | 343.3 | 246.5-248.0 |
| I-6 | 5-Amino-8-cyclohexyl-2-(4-hydroxy-cyclohexylamino)-8H-pyrido[2,3-d]pyrimidin-7-one | 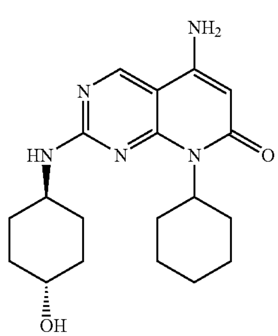 | 357.46 | 292.0-294.0 |

TABLE X-continued

| # | | Structure | MS | MP |
|---|---|---|---|---|
| I-7 | 5-Amino-8-cyclohexyl-2-[4-(morpholine-4-carbonyl)-cyclohexylamino]-8H-pyrido[2,3-d]pyrimidin-7-one | 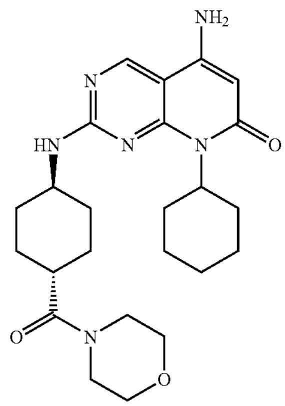 | 454.57 | 185.0-203.0 |
| I-8 | 5-Amino-2-cyclohexylamino-8-(3-hydroxy-propyl)-8H-pyrido[2,3-d]pyrimidin-7-one | 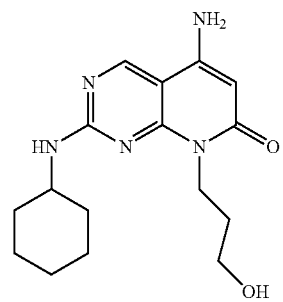 | 317.39 | 131.0-132.5 |
| I-9 | 5-Amino-8-cyclobutyl-6-methyl-2-[4-(pyrrolidine-1-carbonyl)-cyclohexylamino]-8H-pyrido[2,3-d]pyrimidin-7-one | 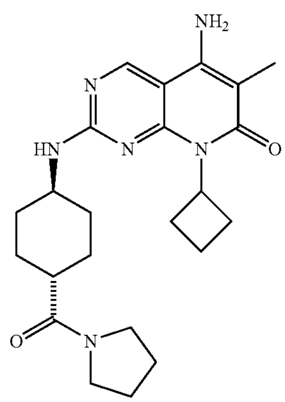 | 424.55 | 276.6-278.4 |
| I-10 | 5-Amino-8-cyclopentyl-6-methyl-2-[4-(morpholine-4-carbonyl)-cyclohexylamino]-8H-pyrido[2,3-d]pyrimidin-7-one | 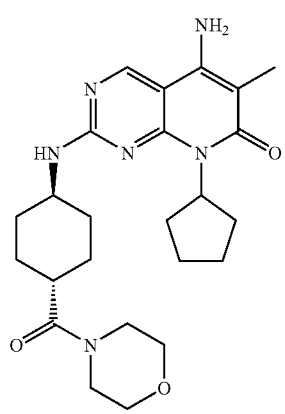 | 454.57 | 186.8-188.0 |

TABLE X-continued

| # | | Structure | MS | MP |
|---|---|---|---|---|
| I-11 | N-[4-(5-Amino-8-cyclopentyl-7-oxo-7,8-dihydro-pyrido[2,3-d]pyrimidin-2-ylamino)-cyclohexyl]-acetamide | 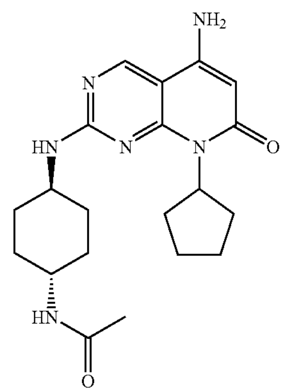 | 384.48 | 172.6-176.6 |
| I-12 | 5-Amino-2-cyclohexylamino-8-cyclopropylmethyl-8H-pyrido[2,3-d]pyrimidin-7-one | 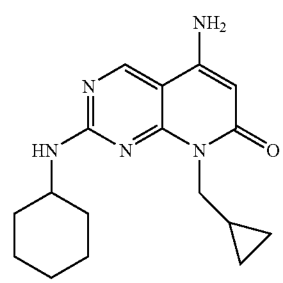 | 313.4 | 133.0-135.0 |
| I-13 | 5-Amino-8-cyclopentyl-2-[4-(morpholine-4-carbonyl)-cyclohexylamino]-8H-pyrido[2,3-d]pyrimidin-7-one | 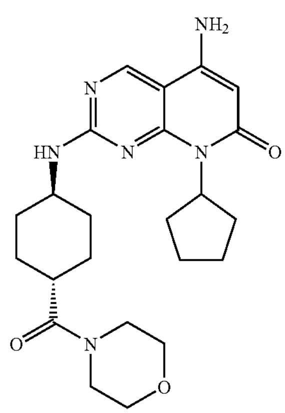 | 440.55 | 292.5-295.3 |
| I-14 | N-[4-(5-Amino-8-cyclohexyl-7-oxo-7,8-dihydro-pyrido[2,3-d]pyrimidin-2-ylamino)-cyclohexyl]-methanesulfonamide | 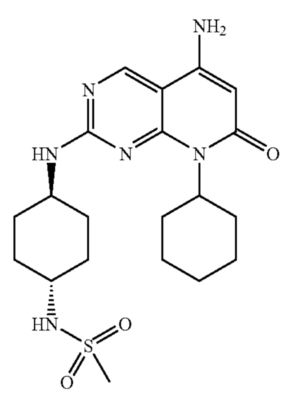 | 434.56 | >300- |

TABLE X-continued

| # | | Structure | MS | MP |
|---|---|---|---|---|
| I-15 | 5-Amino-8-cyclobutyl-2-[4-(4-hydroxy-piperidine-1-carbonyl)-cyclohexylamino]-6-methyl-8H-pyrido[2,3-d]pyrimidin-7-one | 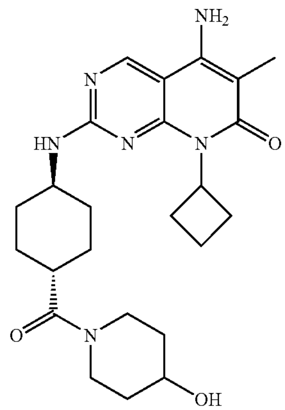 | 454.57 | 191.5-193.0 |
| I-16 | 5-Amino-6-(2-chloro-phenyl)-8-cyclobutyl-2-cyclohexylamino-8H-pyrido[2,3-d]pyrimidin-7-one | 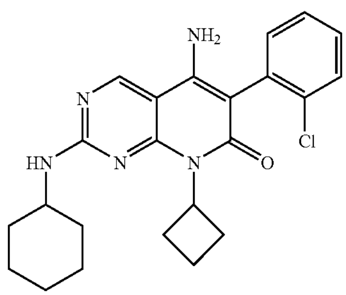 | 423.94 | 175.0-176.0 |
| I-17 | 5-Amino-2-cyclohexylamino-8-cyclopentyl-8H-pyrido[2,3-d]pyrimidin-7-one | 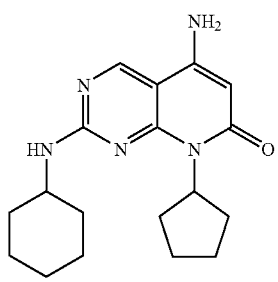 | 327.43 | 125-130 |
| I-18 | N-{4-[5-Amino-8-((1R,3R)-3-hydroxy-cyclopentyl)-7-oxo-7,8-dihydro-pyrido[2,3-d]pyrimidin-2-ylamino]-cyclohexyl}-acetamide | 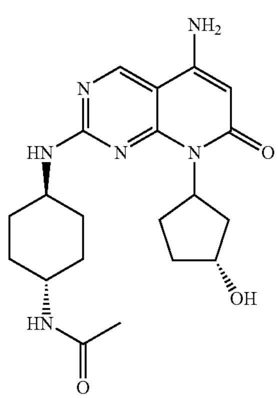 | 400.48 | 210.0-211.5 |

TABLE X-continued

| # | | Structure | MS | MP |
|---|---|---|---|---|
| I-19 | [4-(5-Amino-8-cyclohexyl-7-oxo-7,8-dihydro-pyrido[2,3-d]pyrimidin-2-ylamino)-cyclohexyl]-carbamic acid methyl ester | 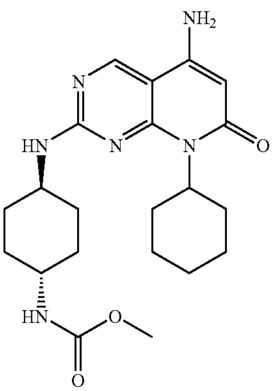 | 414.51 | 193.9-198 |
| I-20 | 5-Amino-8-cyclobutyl-2-[4-(1-hydroxy-1-methyl-ethyl)-cyclohexylamino]-6-methyl-8H-pyrido[2,3-d]pyrimidin-7-one | 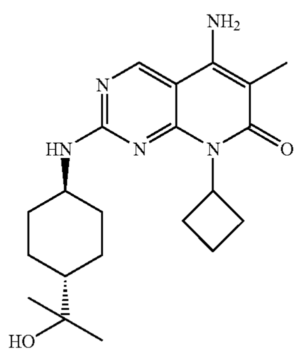 | 385.51 | 223.0-224.8 |
| I-21 | 5-Amino-2-cyclohexylamino-8-ethyl-8H-pyrido[2,3-d]pyrimidin-7-one | 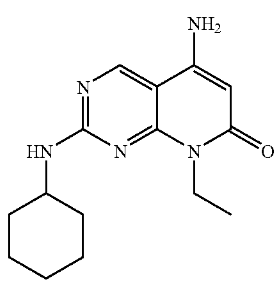 | 287.36 | 147.7-150.1 |
| I-22 | 5-Amino-8-cyclopropyl-2-(4-hydroxy-cyclohexylamino)-8H-pyrido[2,3-d]pyrimidin-7-one | 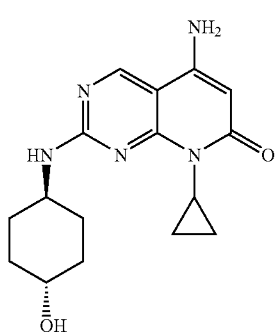 | 315.38 | 256.3-258.7 |

TABLE X-continued

| # | | Structure | MS | MP |
|---|---|---|---|---|
| I-23 | N-[4-(5-Amino-8-cyclopentyl-6-ethyl-7-oxo-7,8-dihydro-pyrido[2,3-d]pyrimidin-2-ylamino)-cyclohexyl]-acetamide | 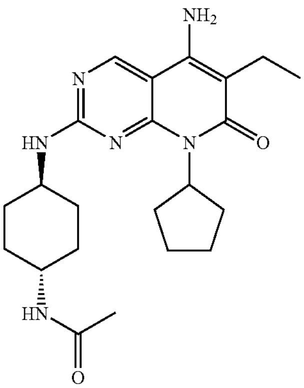 | 412.54 | >300 |
| I-24 | N-[4-(5-Amino-8-cyclobutyl-6-methyl-7-oxo-7,8-dihydro-pyrido[2,3-d]pyrimidin-2-ylamino)-cyclohexyl]-N-methyl-methanesulfonamide | 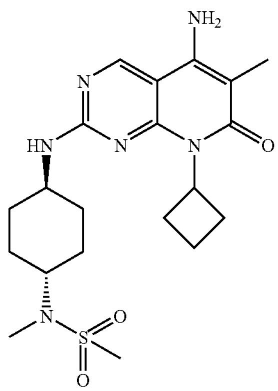 | 434.56 | 260.0-261.0 |
| I-25 | 5-Amino-8-cyclobutyl-2-[4-(4-hydroxy-piperidine-1-carbonyl)-cyclohexylamino]-6-isopropyl-8H-pyrido[2,3-d]pyrimidin-7-one | 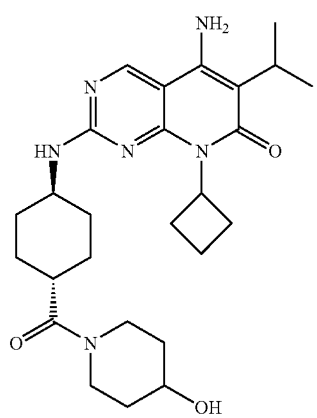 | 482.63 | 170.0-171.0 |
| I-26 | 5-Amino-2-cyclohexylamino-8-cyclopropyl-8H-pyrido[2,3-d]pyrimidin-7-one | 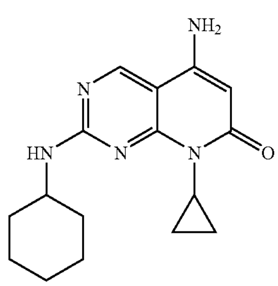 | 299.38 | 117.0-118.0 |

TABLE X-continued

| # | | Structure | MS | MP |
|---|---|---|---|---|
| I-27 | 5-Amino-8-cyclopropyl-2-(1-methanesulfonyl-piperidin-4-ylamino)-8H-pyrido[2,3-d]pyrimidin-7-one | 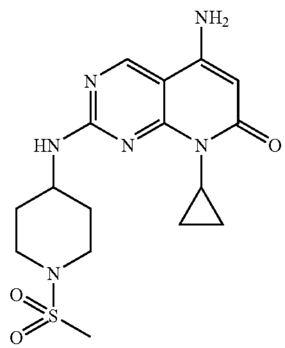 | 224.5-226.0 | |
| I-28 | N-[4-(5-Amino-8-cyclohexyl-7-oxo-7,8-dihydro-pyrido[2,3-d]pyrimidin-2-ylamino)-cyclohexyl]-acetamide | 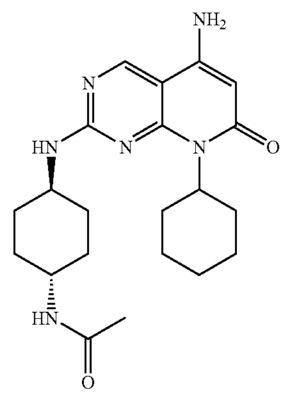 | 398.51 | N.A. |
| I-29 | 5-Amino-8-cyclohexyl-2-(1-methanesulfonyl-piperidin-4-ylamino)-8H-pyrido[2,3-d]pyrimidin-7-one | 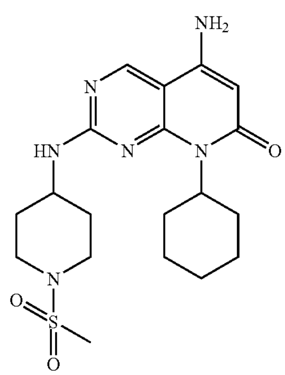 | 420.54 | 250.0-254.0 |
| I-30 | 2-(1-Acetyl-piperidin-4-ylamino)-5-amino-8-cyclopentyl-8H-pyrido[2,3-d]pyrimidin-7-one | 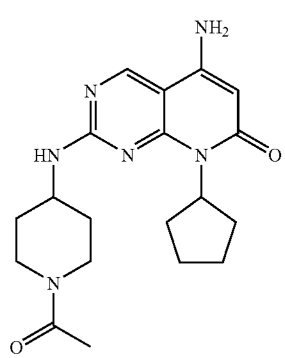 | 370.46 | 282.0-285.0 |

TABLE X-continued

| # | | Structure | MS | MP |
|---|---|---|---|---|
| I-31 | 5-Amino-8-cyclobutyl-2-cyclohexylamino-6-phenyl-8H-pyrido[2,3-d]pyrimidin-7-one | 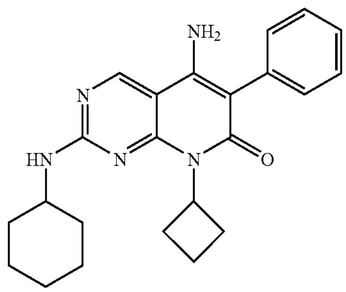 | 389.5 | 160.0-161.0 |
| I-32 | 5-Amino-8-cyclohexyl-2-cyclohexylamino-8H-pyrido[2,3-d]pyrimidin-7-one | 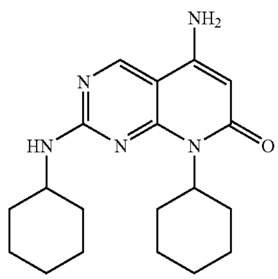 | 341.46 | 243.1-244.9 |
| I-33 | 5-Amino-8-cyclopentyl-2-(tetrahydro-pyran-4-ylamino)-8H-pyrido[2,3-d]pyrimidin-7-one | 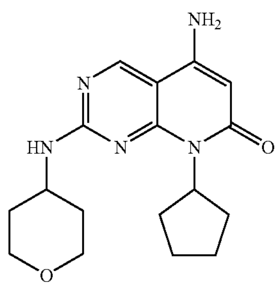 | 329.4 | 120.0-124.0 |
| I-34 | 5-Amino-8-cyclobutyl-6-methyl-2-((1R,2R)-2-methyl-cyclohexylamino)-8H-pyrido[2,3-d]pyrimidin-7-one | 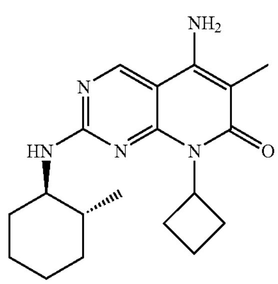 | 341.46 | 209.0-210.0 |
| I-35 | 5-Amino-6-bromo-8-cyclobutyl-2-cyclohexylamino-8H-pyrido[2,3-d]pyrimidin-7-on d]pyrimidin-7-one | 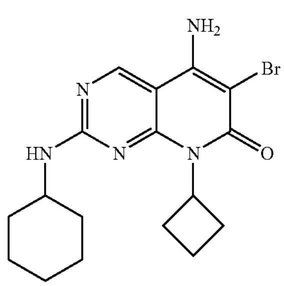 | 392.3 | 221.0-222.0 |

TABLE X-continued

| # | | Structure | MS | MP |
|---|---|---|---|---|
| I-36 | 5-Amino-2-cyclohexylamino-8-cyclopentyl-6-ethyl-8H-pyrido[2,3-d]pyrimidin-7-one | 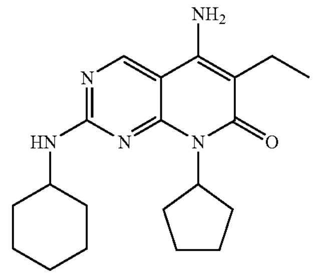 | 355.48 | 229.8-230.5 |
| I-37 | 2-(1-Acetyl-piperidin-4-ylamino)-5-amino-8-((1R,3R)-3-hydroxy-cyclopentyl)-8H-pyrido[2,3-d]pyrimidin-7-one | (racemic) | 386.45 | 192.0-194.0 |
| I-38 | 5-Amino-8-cyclobutyl-2-[4-(4-hydroxy-piperidine-1-carbonyl)-cyclohexylamino]-7-oxo-7,8-dihydro-pyrido[2,3-d]pyrimidine-6-carbonitrile | 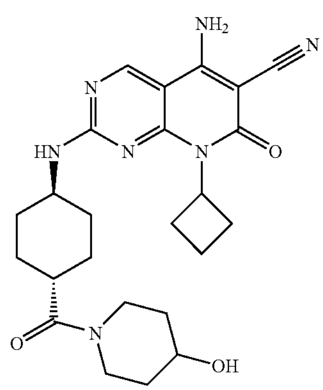 | 465.56 | >300.0 |
| I-39 | [4-(5-Amino-8-cyclopropyl-7-oxo-7,8-dihydro-pyrido[2,3-d]pyrimidin-2-ylamino)-cyclohexyl]-carbamic acid methyl ester | 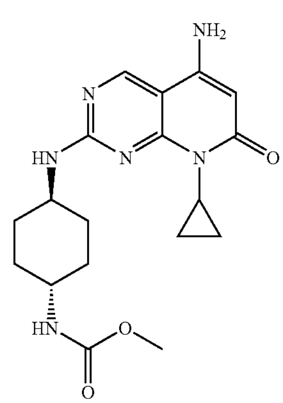 | 372.43 | 257.0-259.0 |

TABLE X-continued

| # | | Structure | MS | MP |
|---|---|---|---|---|
| I-40 | 5-Amino-8-cyclobutyl-2-(1-methanesulfonyl-piperidin-4-ylamino)-6-methyl-8H-pyrido[2,3-d]pyrimidin-7-one | 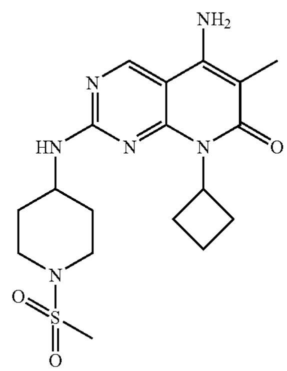 | 406.51 | 265.3-267.0 |
| I-41 | N-[4-(5-Amino-8-cyclopentyl-6-methyl-7-oxo-7,8-dihydro-pyrido[2,3-d]pyrimidin-2-ylamino)-cyclohexyl]-acetamide | 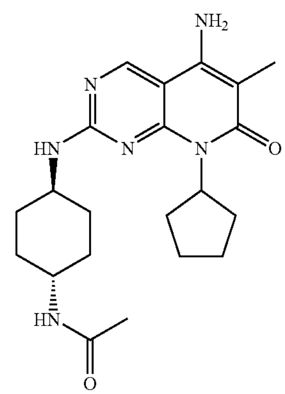 | 398.51 | 296.2-298.2 |
| I-42 | N-{4-[5-Amino-8-(3-hydroxy-propyl)-7-oxo-7,8-dihydro-pyrido[2,3-d]pyrimidin-2-ylamino]-cyclohexyl}-acetamide | 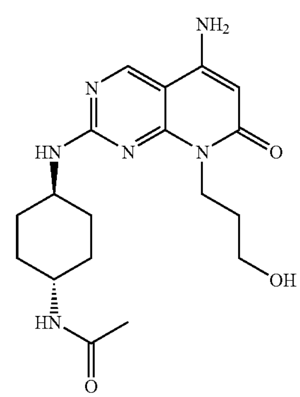 | 374.44 | >300- |
| I-43 | {4-[5-Amino-8-(3-hydroxy-propyl)-7-oxo-7,8-dihydro-pyrido[2,3-d]pyrimidin-2-ylamino]-cyclohexyl}-carbamic acid methyl ester | 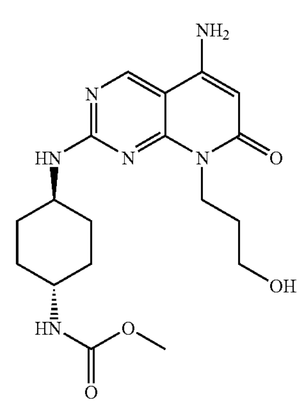 | 390.44 | 190.0-191.0 |

TABLE X-continued

| # | | Structure | MS | MP |
|---|---|---|---|---|
| I-44 | 5-Amino-2-cyclohexylamino-6-methyl-8-(R)-tetrahydro-furan-3-yl-8H-pyrido[2,3-d]pyrimidin-7-one | 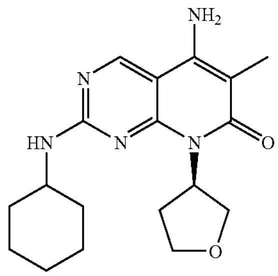 | 343.43 | 225-226 |
| I-45 | 5-Amino-8-cyclopentyl-2-phenylamino-8H-pyrido[2,3-d]pyrimidin-7-one | 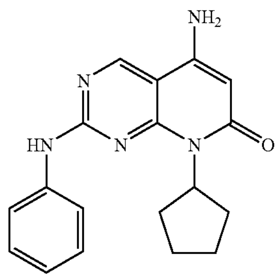 | 321.38 | 128.3-130.0 |
| I-46 | 5-Amino-8-cyclopropylmethyl-2-(tetrahydro-pyran-4-ylamino)-8H-pyrido [2,3-d]pyrimidin-7-one | 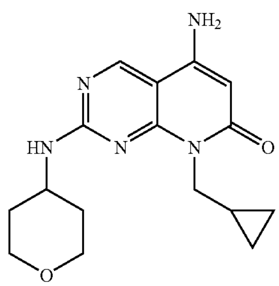 | 315.38 | 135.0-137.4 |
| I-47 | 5-Amino-2-[4-(4-hydroxy-piperidine-1-carbonyl)-cyclohexylamino]-6-methyl-8-(R)-tetrahydro-furan-3-yl-8H-pyrido[2,3-d]pyrimidin-7-one | 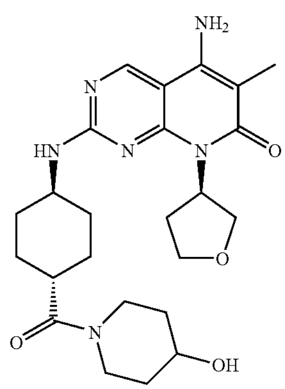 | 470.57 | 173.0-174.0 |
| I-48 | 5-Amino-2-(4-hydroxy-cyclohexylamino)-8-methyl-8H-pyrido[2,3-d]pyrimidin-7-one | 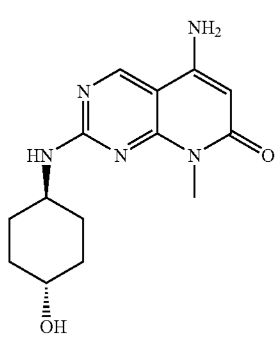 | 289.34 | |

TABLE X-continued

| # | | Structure | MS | MP |
|---|---|---|---|---|
| I-49 | 5-Amino-8-cyclobutyl-2-cyclohexylamino-6-isopropyl-8H-pyrido[2,3-d]pyrimidin-7-one | 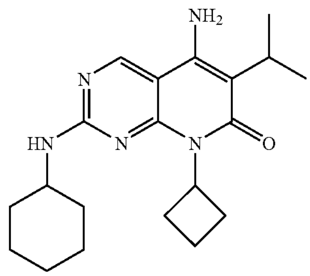 | 355.48 | 277.5-278.0 |
| I-50 | 5-Amino-8-ethyl-2-(tetrahydro-pyran-4-ylamino)-8H-pyrido[2,3-d]pyrimidin-7-one | 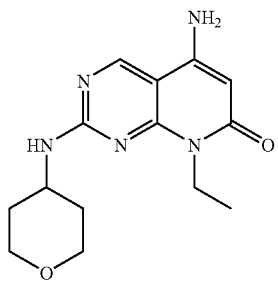 | 289.34 | 235.0-238.2 |
| I-51 | 5-Amino-8-cyclohexyl-2-(tetrahydro-pyran-4-ylamino)-8H-pyrido[2,3-d]pyrimidin-7-one | 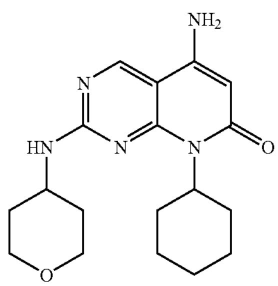 | 343.43 | 160.0-164.0 |
| I-52 | 5-Amino-8-cyclobutyl-2-cyclohexylamino-7-oxo-7,8-dihydro-pyrido[2,3-d]pyrimidine-6-carbonitrile | 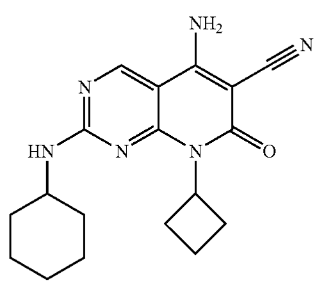 | 338.41 | >300- |
| I-53 | 5-Amino-2-(1-methanesulfonyl-piperidin-4-ylamino)-6-methyl-8-(R)-tetrahydro-furan-3-yl-8H-pyrido[2,3-d]pyrimidin-7-one | 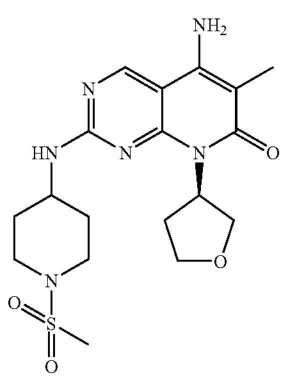 | 422.51 | >300 |

TABLE X-continued

| # | | Structure | MS | MP |
|---|---|---|---|---|
| I-54 | 5-Amino-8-cyclopropyl-2-(tetrahydro-pyran-4-ylamino)-8H-pyrido[2,3-d]pyrimidin-7-one | 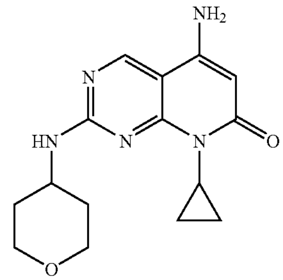 | 301.35 | 264.4-266.8 |
| I-55 | 5-Amino-2-cyclobutylamino-8-cyclopropylmethyl-8H-pyrido[2,3-d]pyrimidin-7-one | 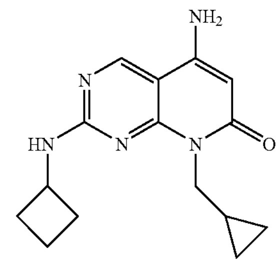 | 285.35 | 236.1-239.1 |
| I-56 | 4-(5-Amino-8-cyclobutyl-6-methyl-7-oxo-7,8-dihydro-pyrido[2,3-d]pyrimidin-2-ylamino)-piperidine-1-carboxylic acid ethyl ester | 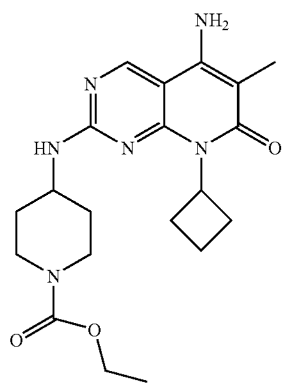 | 400.48 | 201.3-202.6 |
| I-57 | 5-Amino-8-cyclohexyl-2-(4,4-difluoro-cyclohexylamino)-8H-pyrido[2,3-d]pyrimidin-7-one | 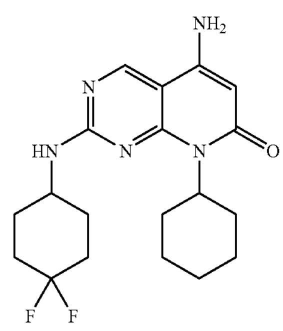 | 377.4 | 240.0-244.1 |
| I-58 | 5-Amino-8-cyclobutyl-6-methyl-2-((1R,2S)-2-methyl-cyclohexylamino)-8H-pyrido[2,3-d]pyrimidin-7-one | 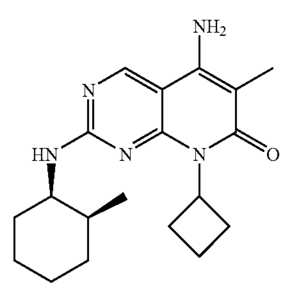 | 341.46 | 160.0-161.0 |

TABLE X-continued

| # | | Structure | MS | MP |
|---|---|---|---|---|
| I-59 | 2-(1-Acetyl-piperidin-4-ylamino)-5-amino-8-cyclopentyl-6-methyl-8H-pyrido[2,3-d]pyrimidin-7-one | 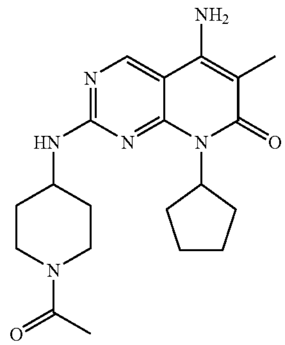 | 384.48 | 281.0-283.0 |
| I-60 | 5-Amino-8-cyclobutyl-6-methyl-2-((1S,2S)-2-methyl-cyclohexylamino)-8H-pyrido[2,3-d]pyrimidin-7-one | (racemic) | 341.46 | 209.0-210.0 |
| I-61 | 2-(1-Acetyl-piperidin-4-ylamino)-5-amino-8-cyclohexyl-8H-pyrido[2,3-d]pyrimidin-7-one | 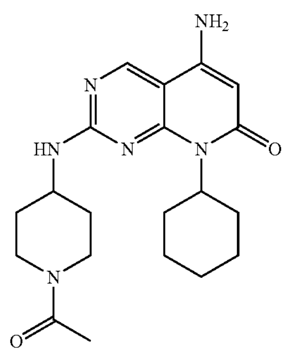 | 384.48 | |
| I-62 | 5-Amino-8-cyclobutyl-6-methyl-2-o-tolylamino-8H-pyrido[2,3-d]pyrimidin-7-one | 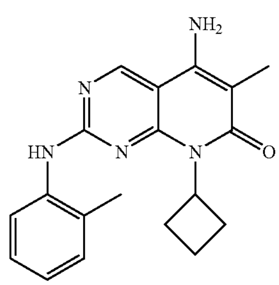 | 335.41 | 186.0-187.0 |
| I-63 | 5-Amino-2-cyclohexylamino-8-phenyl-8H-pyrido[2,3-d]pyrimidin-7-one | 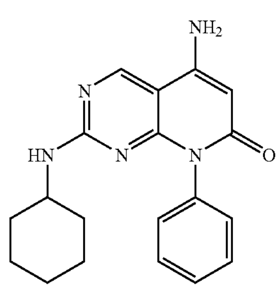 | 335.41 | |

TABLE X-continued

| # | | Structure | MS | MP |
|---|---|---|---|---|
| I-64 | 5-Amino-2-[4-(morpholine-4-carbonyl)-cyclohexylamino]-8-phenyl-8H-pyrido[2,3-d]pyrimidin-7-one | 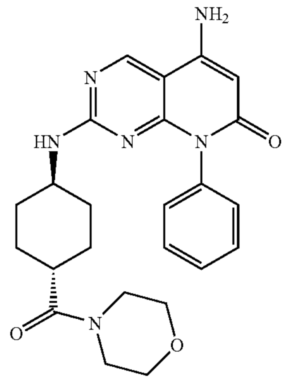 | 448.53 | |
| I-65 | 5-Amino-2-(4,4-difluoro-cyclohexylamino)-8-methyl-8H-pyrido[2,3-d]pyrimidin-7-one | 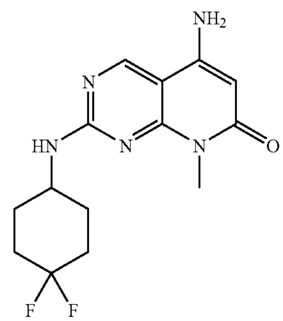 | 309.32 | |
| I-66 | 5-Amino-8-benzyl-2-cyclohexylamino-8H-pyrido[2,3-d]pyrimidin-7-one | 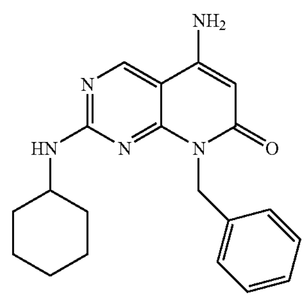 | 349.44 | 221.9-223.8 |
| I-67 | 5-Amino-2-(4-hydroxy-cyclohexylamino)-8-phenyl-8H-pyrido[2,3-d]pyrimidin-7-one | 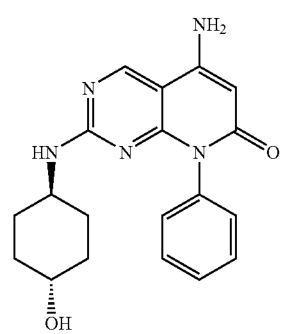 | 351.41 | |
| I-68 | 6-Acetyl-5-amino-8-cyclobutyl-2-cyclohexylamino-8H-pyrido[2,3-d]pyrimidin-7-one | 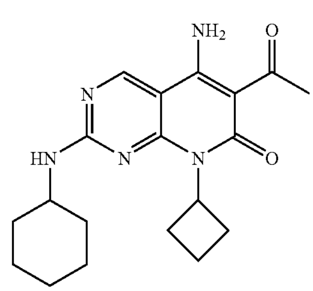 | 355.44 | 256.0-257.0 |

TABLE X-continued

| # | | Structure | MS | MP |
|---|---|---|---|---|
| I-69 | 5-Amino-8-benzyl-2-(tetrahydro-pyran-4-ylamino)-8H-d]pyrimidin-7-one | 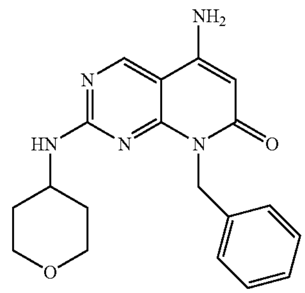 | 351.41 | 245.6-246.8 |
| I-70 | 5-Amino-8-cyclobutyl-2-(2,6-dimethyl-phenylamino)-6-methyl-8H-pyrido[2,3-d]pyrimidin-7-one | 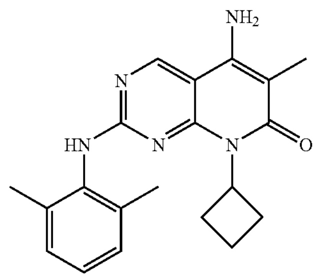 | 349.44 | 213.0-214.0 |

Utility

The compounds of this invention are JNK modulators and as such are expected to be effective in the treatment of a wide range of JNK mediated disorders. Exemplary JNK mediated disorders include, but are not limited to, autoimmune disorders, inflammatory disorders, metabolic disorders, neurological disease, and cancer. Accordingly, compounds of the invention can be used to treat one or more of such disorders. In some embodiments, compounds of the invention can be used to treat a JNK mediated disorder such as rheumatoid arthritis, asthma, type II diabetes, Alzheimer's disease, Parkinson's disease or stroke.

Administration and Pharmaceutical Compositions

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, sub-cutaneous and intravenous) administration or in a form suitable for administration by inhalation or insufflation. The preferred manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use.

Formulations containing about one (1) mg of active ingredient or, more broadly, about 0.01 to about one hundred (100) mg, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxy-methylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the invention may also be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chloro-fluorocarbon (CFC), for example, dichlorodifluoromethane, trichlorofluoromethane, or dichloro-tetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the sub-dermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

Additional objects, advantages, and novel features of this invention will become apparent to those skilled in the art upon examination of the following examples thereof, which are not intended to be limiting.

LIST OF ABBREVIATIONS

Ac₂O Acetic anhydride
AcOH Acetic acid
DBU 1,8-Diazabicyclo[5.4.0]undec-7-ene
DCE 1,2-Dichloroethane
DCM Dichloromethane/Methylene chloride
DIPEA Diisopropylethylamine
DMF N,N-dimethylformamide
DMSO Dimethyl sulfoxide
EDCI 1-(3-Dimethylaminopropyl)-3-ethylcarbodiimide hydrochloride
Et₂O Diethyl ether
EtOH Ethanol/Ethyl alcohol
EtOAc Ethyl acetate
HOBt 1-Hydroxybenzotriazole
LDA Lithium diisopropylamide
LiHMDS Lithium bis(trimethylsilyl)amide
m-CPBA 3-Chloroperoxybenzoic acid
MeOH Methanol/Methyl alcohol
MW Microwaves
NMP 1-Methyl-2-pyrrolidinone
PMB 4-Methoxy benzyl
RT Room temperature
TBME tert-Butyl methyl ether
TFA Trifluoroacetic acid
Tf₂O Trifluoromethanesulfonic anhydride
THF Tetrahydrofuran
TLC Thin layer chromatography

EXAMPLES

The following preparations and examples are given to enable those skilled in the art to more clearly understand and to practice the present invention. They should not be considered as limiting the scope of the invention, but merely as being illustrative and representative thereof.

Preparation 1

Synthesis of (4-amino-cyclohexyl)-morpholin-4-yl-methanone hydrochloride

The synthesis of (4-amino-cyclohexyl)-morpholin-4-yl-methanone hydrochloride was carried out according to the process shown in Scheme 1.

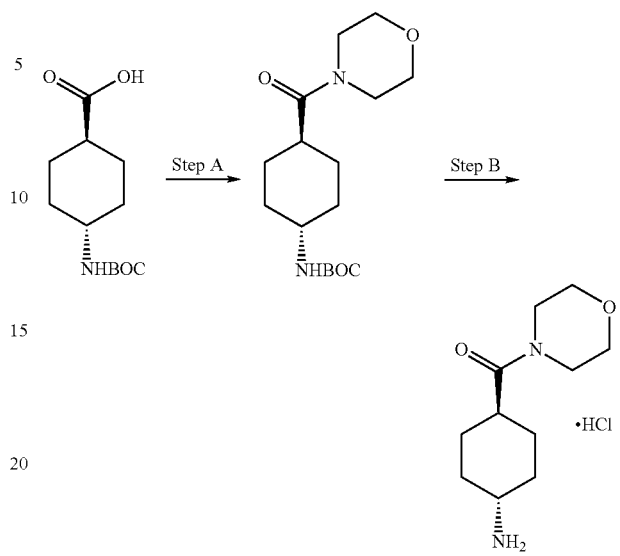

SCHEME 1

Step A: A mixture of 4-tert-butoxycarbonylamino-cyclohexanecarboxylic acid (10.0 g, 41 mmol), EDCI (23.64 g, 123 mmol) and HOBt (18.88 g, 123 mmol) in 1-methyl-2-pyrrolidinone (150 mL) was stirred at RT for 3 hours. Morpholine (10.75 mL, 123 mmol) was then added, and the resulting mixture was stirred at RT for 78 hours. The reaction was quenched by adding water and the resulting mixture was extracted with EtOAc. The organic layer was separated and washed twice with K₂CO₃ (sat'd aq) and an HCl (aq, 10%), again with once with a saturated K₂CO₃ (sat'd aq) and with brine. The organic layer was then dried over anhydrous sodium sulfate, filtered and evaporated under reduced pressure. The crude residue was triturated with Et₂O and filtered to give 5.9 g of [4-(morpholine-4-carbonyl)-cyclohexyl]-carbamic acid tert-butyl ester as a white powder.

Step B: HCl (2 M aq, 150 mL) was added to a suspension of [4-(morpholine-4-carbonyl)-cyclohexyl]-carbamic acid tert-butyl ester (5.8 g) in MeOH, and the resulting mixture was stirred at RT overnight. The reaction mixture was evaporated under reduced pressure, the oily residue was taken up in EtOAc, and the resulting mixture was sonicated. The solid formed was collected by filtration and dried under reduced pressure to afford 5.2 g of (4-amino-cyclo-hexyl)-morpholin-4-yl-methanone hydrochloride.

Preparation 2

Synthesis of 5-Amino-8-methyl-2-methylsulfanyl-8H-pyrido[2,3-d]pyrimidin-7-one

The synthesis of 5-amino-8-methyl-2-methylsulfanyl-8H-pyrido[2,3-d]pyrimidin-7-one was carried out according to the process shown in Scheme 2.

SCHEME 2

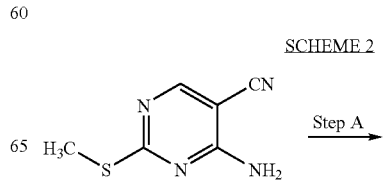

-continued

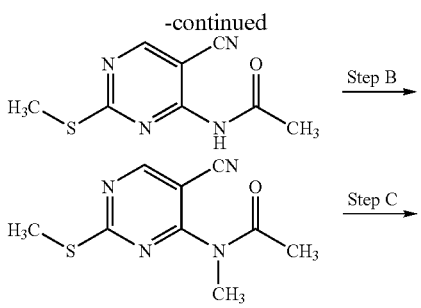

Preparation 3

Synthesis of 5-Amino-8-cyclopentyl-2-methylsulfanyl-8H-pyrido[2,3-d]-pyrimidin-7-one The synthesis of 5-amino-8-cyclopentyl-2-methylsulfanyl-8H-pyrido[2,3-d]pyrimidin-7-one was carried out according to the process shown in Scheme 3.

SCHEME 3

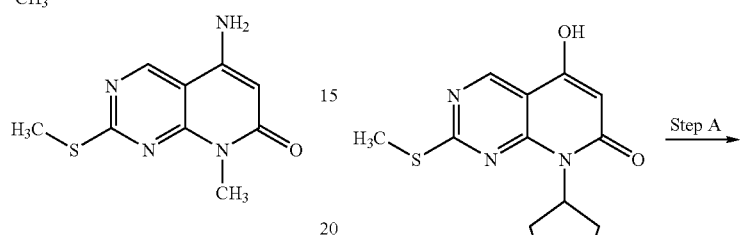

Step A: To a suspension of 4-amino-2-methylsulfanyl-pyrimidine-5-carbonitrile (5.45 g) in pyridine (66 mL) was added Ac$_2$O (31 mL) at RT. The reaction mixture was stirred at 80° C. for 23 h, then was cooled to RT and evaporated under reduced pressure. The residue was dissolved in DCM (150 mL) and washed with NaHCO$_3$ (sat'd aq) and brine. The organic layer was dried over MgSO$_4$, filtered, and concentrated under reduced pressure. The crude residue was purified by flash chromatography (from 0 to >50% EtOAc/Hexane in 20 min.) to give 3.25 g (48% yield) of N-(5-cyano-2-methylsulfanyl-pyrimidin-4-yl)-acetamide as a yellow solid. MS=167 [M−C$_2$H$_3$O+1]$^+$.

Step B: To a solution of N-(5-cyano-2-methylsulfanyl-pyrimidin-4-yl)-acetamide (562 mg, 2.70 mmol) and methyl iodide (1.7 mL, 27.0 mmol) in anhydrous DMSO (14 mL) was added NaH (60% wt. dispersion in mineral oil, 130 mg, 3.23 mmol) at 0° C. The reaction mixture was stirred at RT for 16 h and was then quenched by adding water (50 mL). The resulting mixture was extracted with EtOAc (2×100 mL). The combined organic layers were washed with brine (2×100 mL), dried over MgSO$_4$, filtered, and concentrated under reduced pressure. The crude residue was purified by flash chromatography (from 0 to >33% EtOAc/hexane in 5 min.) to afford 431 mg (72% yield) of N-(5-cyano-2-methylsulfanyl-pyrimidin-4-yl)-N-methyl-acetamide as an off-white solid. MS=223 [M+1]$^+$.

Step C: To a solution of N-(5-cyano-2-methylsulfanyl-pyrimidin-4-yl)-N-methyl-acetamide (400 mg, 1.80 mmol) in THF (18 mL) was added a solution of lithium bis(trimethylsilyl)amide (1.0 M in hexane, 7.2 mL, 7.20 mmol) at RT. The reaction mixture was stirred at RT for 1 h, then quenched with water (100 mL). The resulting mixture was extracted with EtOAc (100 mL); the organic layer dried over MgSO$_4$, filtered and concentrated under reduced pressure. The crude residue was purified by flash chromatography (from 10 to >100% EtOAc/hexane in 10 min.) to give 163 mg (41% yield) of 5-amino-8-methyl-2-methylsulfanyl-8H-pyrido[2,3-d]-pyrimidin-7-one as a yellow solid.

Using the above described procedure and the appropriate starting materials the following compounds were prepared:
5-Amino-8-ethyl-2-methylsulfanyl-8H-pyrido[2,3-d]pyrimidin-7-one; MS=237 [M+1]$^+$;
5-Amino-8-cyclopropylmethyl-2-methylsulfanyl-8H-pyrido[2,3-d]pyrimidin-7-one; and
5-Amino-8-benzyl-2-methylsulfanyl-8H-pyrido[2,3-d]pyrimidin-7-one.

Step A: Phosphorus oxybromide (11.3 mL) was added to a mixture of 8-cyclopentyl-5-hydroxy-2-methylsulfanyl-8H-pyrido[2,3-d]pyrimidin-7-one (2.56 g, 9.23 mmol) in dichloro-ethane (13 mL) at RT. The reaction mixture was heated to 100° C. in a microwave reactor for 1 h, then cooled to RT. The resulting mixture was partitioned between EtOAc (200 mL) and NaHCO$_3$ (sat'd aq, 200 mL), and the aqueous layer extracted with EtOAc (100 mL). The combined organic layers were washed with NaHCO$_3$ (sat'd aq, 3×100 mL) and water (2×100 mL), dried over MgSO$_4$, filtered and evaporated under reduced pressure to give 1.58 g (50% yield) of 5-bromo-8-cyclopentyl-2-methylsulfanyl-8H-pyrido[2,3-d]pyrimidin-7-one. MS=340, 342 [M+H]$^+$.

Step B: Sodium azide (543 mg, 8.35 mmol) was added to a mixture of 5-bromo-8-cyclopentyl-2-methylsulfanyl-8H-pyrido[2,3-d]pyrimidin-7-one (1.42 g, 4.17 mmol) in DMF (17 mL) at RT and the reaction mixture was heated to 90° C. in a microwave reactor for 30 min. The resulting mixture was then cooled to RT and quenched with water (70 mL). The solid that formed was collected by filtration, dried under reduced pressure, dissolved in THF and adsorbed onto silica gel. This material was purified by flash chromatography (from 10 to >25% EtOAc/hexanes in 20 min) to afford 0.720 g (57% yield) of 5-azido-8-cyclopentyl-2-methylsulfanyl-8H-pyrido[2,3-d]pyrimidin-7-one as a yellow solid. MS=303 [M+H]+.

Step C: Triphenylphosphine (1.68 g, 6.40 mmol) was added, at RT, to a solution of 5-azido-8-cyclopentyl-2-methylsulfanyl-8H-pyrido[2,3-d]pyrimidin-7-one (1.29 g, 4.27 mmol) in THF (43 mL) and the reaction mixture was stirred at 35° C. for 2 h. An HCl (1 M, 22 mL) was then added and the reaction mixture was heated at reflux for 2 h and then was stored at 4° C. overnight. The resulting mixture was neutralized to pH 8 with NaHCO₃ (sat'd aq), and was extracted with EtOAc (2×200 mL). The combined organic layers were dried over MgSO₄, filtered and evaporated under reduced pressure. The crude residue was purified by flash chromatography (from 2 to >5% MeOH/DCM in 20 min.) to give 0.89 g (75% yield) of 5-amino-8-cyclopentyl-2-methylsulfanyl-8H-pyrido[2,3-d]pyrimidin-7-one as a yellow solid. MS=277 [M+1]+.

5-Amino-8-cyclohexyl-2-methylsulfanyl-8H-pyrido[2,3-d]pyrimidin-7-one was prepared using the above described procedure and the appropriate starting materials.

Preparation 4

Synthesis of 8-Cyclopentyl-5-hydroxy-2-methylsulfanyl-8H-pyrido[2,3-d]pyrimidin-7-one

SCHEME 4

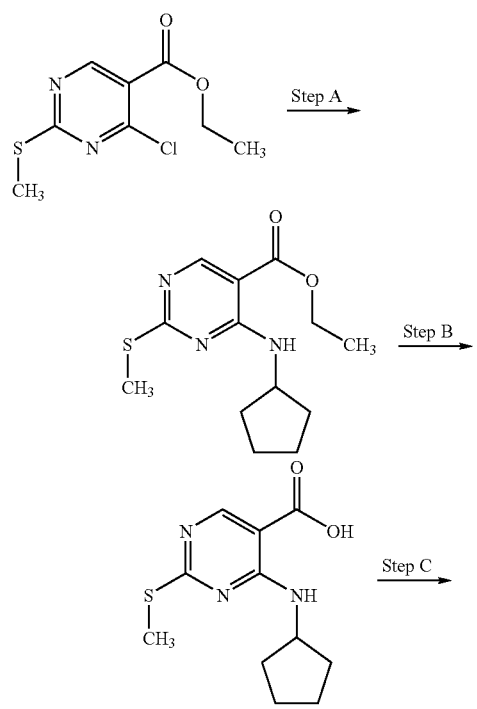

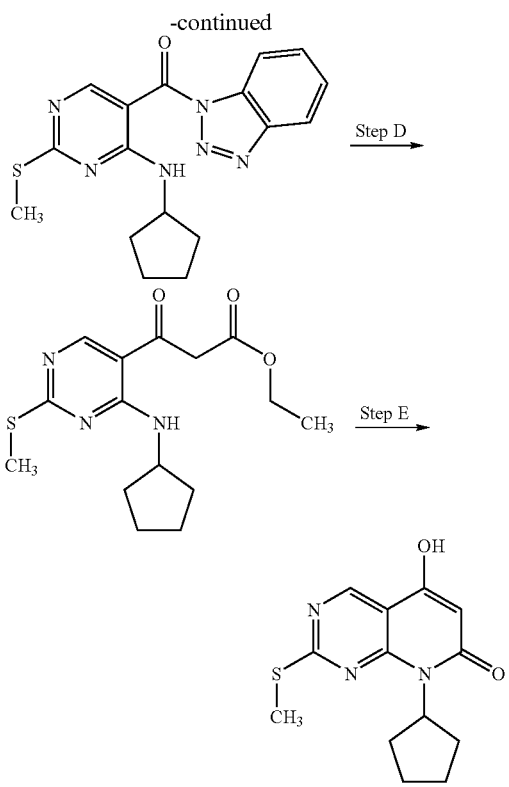

Step A: Cyclopentylamine (12.7 mL, 129.3 mmol) was added to solution of 4-chloro-2-methylsulfanyl-pyrimidine-5-carboxylic acid ethyl ester (10 g, 43.10 mmol) in DCM (250 mL) at RT and the resulting mixture was stirred for 3 days. The reaction mixture was washed 3 times with water; the aqueous extracts were combined and extracted twice with DCM. The combined organic extracts were dried over Na₂SO₄, filtered, and evaporated under reduced pressure to give 12.8 g of 4-cyclopentylamino-2-methylsulfanyl-pyrimidine-5-carboxylic acid ethyl ester as a crude oil without further purifications.

Step B: NaOH (1 M aq, 31 mL) was added to a suspension of 4-cyclopentylamino-2-methylsulfanyl-pyrimidine-5-carboxylic acid ethyl ester (11.7 g, 41.6 mmol) in EtOH (14 mL) and the resulting mixture was heated at reflux for 1.5 h. The reaction mixture was cooled to RT and HCl (1 M aq) was added until pH 4 was reached. The white solid, which crashed out of solution, was collected by filtration, washed with water and heptane and then dried under reduced pressure to afford 10.241 g (97% yield) of 4-cyclopentylamino-2-methylsulfanyl-pyrimidine-5-carboxylic acid.

Step C: EDCI (7.690 g, 40.26 mmol) and benzotriazole (4.796 g, 40.26 mmol) were added to a suspension of 4-cyclopentylamino-2-methylsulfanyl-pyrimidine-5-carboxylic acid (10.186 g, 40.26 mmol) in DCM (250 mL), at RT, and the reaction mixture was stirred for 1 h. The resulting mixture was washed 3 times with water; the combined aqueous extracts were extracted twice with DCM. The combined organic layers were dried over Na₂SO₄, filtered and evaporated under reduced pressure to give a crude oil. This material was triturated with hot tert-butyl methyl ether and the mixture was left to stand overnight. The white solid which formed was collected by filtration to give 7.698 g (54% yield) of benzotriazol-1-yl-(4-cyclopentylamino-2-methylsulfanyl-pyrimidin-5-yl)-methanone.

The following compounds were prepared using the above described procedure and the appropriate starting materials:

benzotriazol-1-yl-(4-cyclohexylamino-2-methylsulfanyl-pyrimidin-5-yl)-methanone;

benzotriazol-1-yl-(4-cyclopropylamino-2-methylsulfanyl-pyrimidin-5-yl)-methanone.

Step D: A solution of lithium diisopropylamide (1.8 M in toluene, 26.6 mL) was added, dropwise, at −78° C., to a solution of EtOAc (2.33 mL, 23.92 mmol) in THF (100 mL), and the resulting mixture was stirred at −78° C. for 1 h. A solution of benzotriazol-1-yl-(4-cyclopentylamino-2-methylsulfanyl-pyrimidin-5-yl)-methanone (7.698 g, 21.74 mmol) in THF (60 mL) was added via cannula to the reaction mixture, and the resulting mixture was stirred at −78° C. for 4 h and at RT for 15 h. The reaction mixture was then treated with HCl (1 M aq) and then with HCl (6 M aq) until pH 2. The resulting mixture was stirred at RT for 1 h, was then diluted with EtOAc. The organic layer was separated and washed 3 times with water; the aqueous layers were combined and extracted 3 times with EtOAc and 3 times with a mixture of isopropanol and chloroform (1:1). The combined organic extracts were dried over Na$_2$SO$_4$, filtered, and evaporated under reduced pressure. The crude residue was purified by flash chromatography (heptane/EtOAc, 100/0 to 80/20) to give 3.03 g (42% yield) of 3-(4-cyclopentylamino-2-methylsulfanyl-pyrimidin-5-yl)-3-oxo-propionic acid ethyl ester.

Step E: Diisopropylethylamine (12 mL) and DBU (1.62 mL) were added to 3-(4-cyclopentylamino-2-methylsulfanyl-pyrimidin-5-yl)-3-oxo-propionic acid ethyl ester (3.0 g, 9.29 mmol) and the resulting mixture was heated to 120° C. for 1 h. The reaction mixture was then cooled to RT and acidified with HCl (1 M aq) to pH 1. The resulting mixture was diluted with EtOAc and washed 3× with HCl (1 M aq). The combined aqueous layers were extracted with EtOAc and then 3× with a 1:1 mixture of isopropanol and chloroform. The combined organic extracts were dried over Na$_2$SO$_4$, filtered and evaporated under reduced pressure to afford 2.5 g (97% yield) of 8-cyclopentyl-5-hydroxy-2-methylsulfanyl-8H-pyrido[2,3-d]pyrimidin-7-one.

5-Hydroxy-2-methylsulfanyl-8-phenyl-8H-pyrido[2,3-d]pyrimidin-7-one was prepared using the above described procedure and the appropriate starting materials.

Preparation 5

Synthesis of 8-Cyclohexyl-5-hydroxy-2-methylsulfanyl-8H-pyrido[2,3-d]pyrimidin-7-one

SCHEME 5

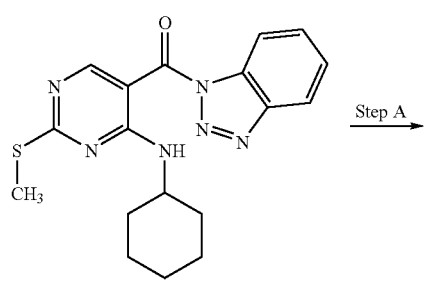

Step A →

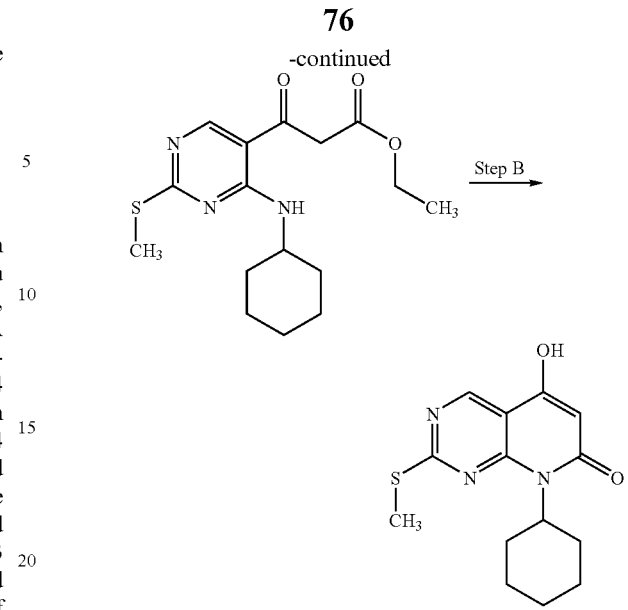

Step B →

Step A: Sodium hydride (60% dispersion in mineral oil, 6.07 g, 151.60 mmol) was added portionwise, under nitrogen atmosphere, at 0° C., to a mixture of benzotriazol-1-yl-(4-cyclohexylamino-2-methylsulfanyl-pyrimidin-5-yl)-methanone (25.4 g, 68.95 mmol) and tert-butyl ethyl malonate (14.36 mL, 75.83 mmol) in anhydrous DMF (400 mL) and the resulting mixture was stirred at RT for 15 h. The reaction mixture was poured into a mixture of NaHSO$_4$ (aq 10%, 1 L) and ice (200 mL) and then was carefully extracted with EtOAc (2×200 mL). The combined organic extracts were washed with water (2×100 mL), dried over Na$_2$SO$_4$, filtered, and evaporated under reduced pressure. The yellow oil obtained was dissolved in DCM (30 mL) and trifluoroacteic acid (60 mL) was added. The reaction mixture was heated at reflux for 1 h. The resulting mixture was cooled and the solvent was evaporated under reduced pressure. NaHCO$_3$ (sat'd aq) was added until pH 7 was reached and the resulting mixture was extracted with EtOAc (3×100 mL). The combined organic extracts were dried over Na$_2$SO$_4$, filtered and evaporated under reduced pressure. The crude residue was purified by flash chromatography (EtOAc/hexane 10/90 to 15/85) to afford 20.9 g (90% yield) of 3-(4-cyclohexylamino-2-methylsulfanyl-pyrimidin-5-yl)-3-oxo-propionic acid ethyl ester.

Step B: DBU (11.05 mL) was added dropwise, under argon atmosphere, to a mixture of 3-(4-cyclohexylamino-2-methylsulfanyl-pyrimidin-5-yl)-3-oxo-propionic acid ethyl ester (21.5 g) and DIPEA (85 mL), and the resulting mixture heated at 125° C. for 1 h, then stirred at RT overnight. The volatiles were evaporated under reduced pressure, and the residue was diluted with EtOAc and HCl (1 M aq). The solid residue was collected by filtration, the organic layer was separated, and the aqueous layer was extracted 3× with EtOAc. The combined organic extracts were dried over Na$_2$SO$_4$, filtered and evaporated under reduced pressure. The combined solids were washed 3× with NaHSO$_4$ (aq 10%), twice with water, hexane (8×100 mL), and a 2:1 mixture of hexane and EtOAc (4×100 mL) to give, after drying under reduced pressure, 19.9 g (99% yield) of 8-cyclohexyl-5-hydroxy-2-methylsulfanyl-8H-pyrido[2,3-d]pyrimidin-7-one without further purifications.

8-Cyclopropyl-5-hydroxy-2-methylsulfanyl-8H-pyrido[2,3-d]pyrimidin-7-one was prepared using the above described procedure and the appropriate starting materials.

Preparation 6

Synthesis of N-(4-Amino-cyclohexyl)-acetamide hydrochloride salt

The synthesis of N-(4-amino-cyclohexyl)-acetamide hydrochloride salt was carried out according to the process shown in Scheme 6.

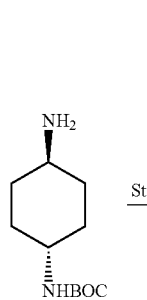

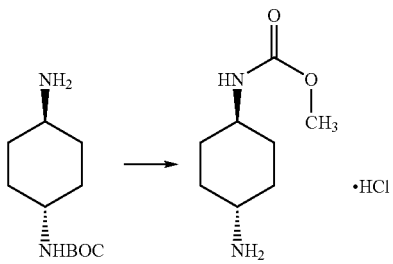

Step A: To a cooled suspension of (4-amino-cyclohexyl)-carbamic acid tert-butyl ester (15 g) in DCM (300 mL) was added Ac$_2$O (10.8 mL) followed by TEA (2.19 mL), and the resulting mixture was stirred at RT for 3 h. The reaction mixture was then partitioned between DCM and water, and isopropyl amine was added to facilitate the separation. The organic layer was washed with dilute aqueous NaHCO$_3$, dried over Na$_2$SO$_4$, filtered and evaporated under reduced pressure. The residue was triturated with Et$_2$O, the solid was collected by filtration and dried under reduced pressure to afford 14.3 g of (4-acetylamino-cyclohexyl)-carbamic acid tert-butyl ester.

Step B: HCl (2.0 M in MeOH, 200 mL) was added to a suspension of (4-acetylamino-cyclohexyl)-carbamic acid tert-butyl ester (14.3 g) in MeOH (100 mL) and the resulting mixture was stirred at RT for 18 h. A second aliquot of HCl (2.0 M in MeOH, 100 mL) was then added and the resulting mixture was stirred at RT overnight. The reaction mixture was then concentrated under reduced pressure and the residue was triturated with Et$_2$O. The very hygroscopic solid was collected by filtration after treatment with toluene, was then dried at 50° C. under reduced pressure to afford 12.46 g of N-(4-amino-cyclohexyl)-acetamide hydrochloride.

N-(4-Amino-cyclohexyl)-methanesulfonamide hydrochloride was prepared following the above procedure (in Step A methanesulfonyl chloride was used) and using the appropriate starting materials.

Preparation 7

Synthesis of (4-amino-cyclohexyl)-carbamic acid methyl ester hydrochloride salt Methyl chloroformate (0.468 mL, 6.06 mmol) was added dropwise, over a period of 20 min, under argon atmosphere, at 0° C., to a mixture of (4-amino-cyclohexyl)-carbamic acid tert-butyl ester (1.0 g, 4.67 mmol) and pyridine (0.479 mL, 6.06 mmol) in THF (6 mL) and the resulting mixture was stirred at RT for 24 h. The reaction mixture was then evaporated under reduced pressure and water (300 mL) was added to the solid residue. The resulting mixture was extracted 3 times with EtOAc (100 mL), the combined organics were washed 3 times with water (100 mL), twice with NaHSO$_4$ (aq 1%, 150 mL) and twice with water (150 mL), dried over Na$_2$SO$_4$, filtered and concentrated under reduced pressure. The remaining white solid was mixed with HCl (2.0 M in MeOH, 200 mL) and the resulting mixture was stirred at RT for 5 h. The reaction mixture was then evaporated under reduced pressure to give 1.1 g of (4-amino-cyclohexyl)-carbamic acid methyl ester hydrochloride salt.

Preparation 8

Synthesis of 5-Amino-8-cyclopropyl-2-methylsulfanyl-8H-pyrido[2,3-d]pyrimidin-7-one Palladium hydroxide on carbon (10% wt., 150 mg) was added to a solution of 5-azido-8-cyclopropyl-2-methylsulfanyl-8H-pyrido[2,3-d]pyrimidin-7-one (1.5 g) in glacial acetic acid (80 mL) and the resulting mixture was stirred under H$_2$ (balloon pressure) for 2 h. A mixture of DCM and MeOH (80/20, 100 mL) was added and the resulting mixture was filtered over a CELITE™ pad and the filter cake was washed with a mixture of DCM and MeOH (80/20, 500 mL). The filtrate was concentrated under reduced pressure to give 1.7 g 5-amino-8-cyclopropyl-2-methylsulfanyl-8H-pyrido[2,3-d]pyrimidin-7-one as a green solid without further purifications. MS=248.9 [M+H]$^+$.

Preparation 9

Synthesis of 5-Amino-8-cyclobutyl-2-methylsulfanyl-8H-pyrido[2,3-d]pyrimidin-7-one

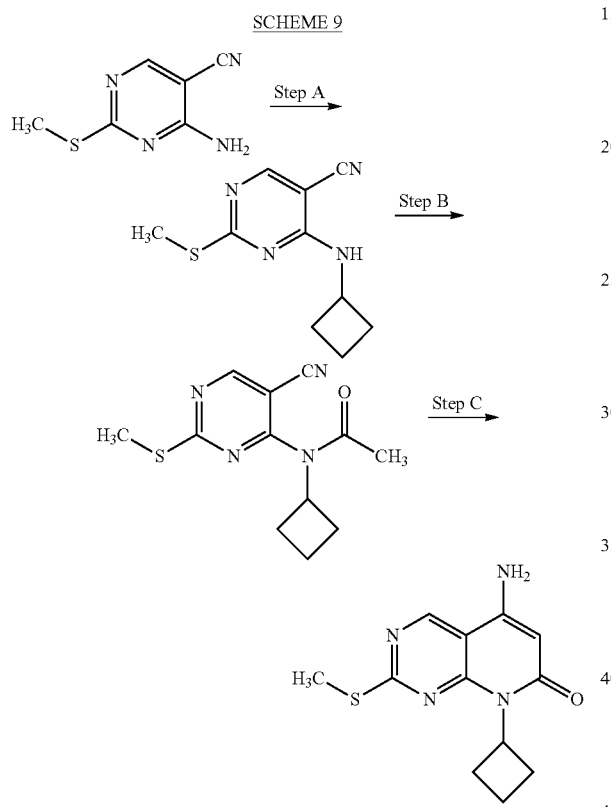

Step A: Sodium hydride (60% suspension in mineral oil, 480 mg, 12.0 mmol) was added to a solution of 4-amino-2-(methylthio)pyrimidine (1.66 g, 10.0 mmol) in DMSO (20 mL) at RT, and the resulting mixture was stirred for 30 min. Cyclobutylbromide (1.9 mL, 20.0 mmol) was then added and the reaction mixture was stirred at 50° C. for 64 h. The resulting mixture was then cooled to RT, quenched with water (200 mL) and extracted with EtOAc (2×400 mL). The combined organic extracts were washed with brine (200 mL), dried over MgSO$_4$, filtered and evaporated under reduced pressure. The crude residue was purified by flash chromatography (EtOAc/hexane, 0/100 to 30/70 in 10 min) to afford 354 mg (16% yield) of 4-cyclobutylamino-2-methylsulfanyl-pyrimidine-5-carbonitrile as a white solid. MS=221 [M+H]$^+$.

Step B: A solution of methyl magnesium bromide (3.0 M in Et$_2$O, 0.58 mL, 1.75 mmol) was added, at RT, to a solution of 4-cyclobutylamino-2-methylsulfanyl-pyrimidine-5-carbonitrile (350 mg, 1.59 mmol) in toluene (32 mL) and the resulting mixture was stirred for 30 min. Ac$_2$O (3.0 mL, 31.8 mmol) was then added and the reaction mixture was heated at reflux for 5 days. The reaction mixture was then cooled to RT, quenched with water (100 mL) and extracted with EtOAc (2×100 mL). The combined organic extracts were dried over MgSO$_4$, filtered and evaporated under reduced pressure. The crude residue was purified by flash chromatography (EtOAc/hexane, 0/100 to 30/70 in 10 min) to afford 207 mg (50% yield) of N-(5-cyano-2-methylsulfanyl-pyrimidin-4-yl)-N-cyclobutyl-acetamide as a yellow solid.

Step C: A solution of lithium bis(trimethylsilyl)amide (1.0 M in THF, 0.78 mL, 0.781 mmol) was added, at RT, to a solution of N-(5-cyano-2-methylsulfanyl-pyrimidin-4-yl)-N-cyclobutyl-acetamide (205 mg, 0.781 mmol) in THF (7.8 mL) and the resulting mixture was stirred for 1 h. The reaction mixture was then quenched with water (10 mL) and extracted with EtOAc (2×20 mL). The combined organic extracts were dried over MgSO$_4$, filtered and evaporated under reduced pressure. The crude residue was purified by flash chromatography (MeOH/DCM, 1/99 to 5/95 in 10 min) to afford 98 mg (48% yield) as a white solid. MS=263 [M+H]$^+$.

Preparation 10

Synthesis of 5-Amino-8-[3-(tert-butyl-dimethyl-silanyloxy)-propyl]-2-methylsulfanyl-8H-pyrido[2,3-d]pyrimidin-7-one

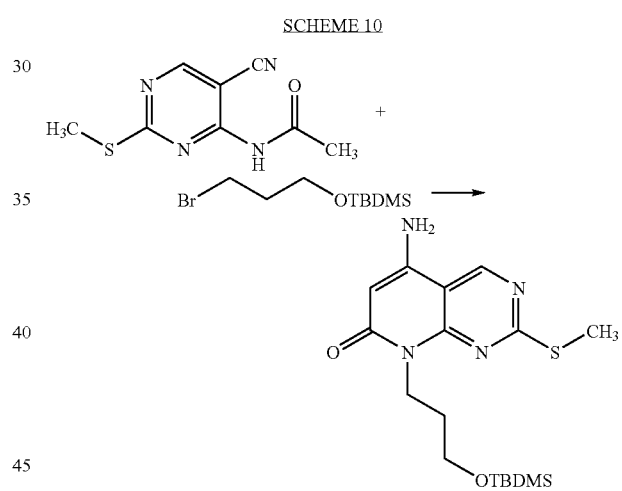

Sodium hydride (60% suspension in mineral oil, 468 mg) was added portionwise, at RT, under argon atmosphere, to a solution of N-(5-cyano-2-methylsulfanyl-pyrimidin-4-yl)-acetamide (2.03 g, 9.75 mmol) in anhydrous DMSO (20 mL) and the resulting mixture was stirred at RT for 40 min. (3-Bromopropoxy)-tert-butyldimethylsilane (3.39 mL, 14.63 mmol) was then added dropwise over a period of 2 min at RT and the reaction mixture was stirred for 2 h. The resulting mixture was then heated at 85° C. for 2 h; a second portion of NaH (60% suspension in mineral oil, 78 mg) was then added and was followed after 30 min by (3-bromopropoxy)-tert-butyldimethylsilane (0.45 mL). The resulting mixture was heated at 85° C. for 1 h, cooled and quenched with water. The resulting mixture was extracted with EtOAc (3×50 mL); the combined organic layers were washed with water, dried over MgSO$_4$, filtered and evaporated under reduced pressure. The crude residue was purified by flash chromatography to afford 800 mg (22% yield) of 5-amino-8-[3-(tert-butyl-dimethyl-silanyloxy)-propyl]-2-methylsulfanyl-8H-pyrido[2,3-d]pyrimidin-7-one and 600 mg of uncyclized N-[3-(tert-butyldimethyl-silanyloxy)-propyl]-N-(5-cyano-2-methylsulfanyl-pyrimidin-4-yl)-acetamide which was converted in the title compound by treatment with lithium bis(trimethylsilyl)amide as described in Preparation 2 Step C.

Preparation 11

Synthesis of 5-Amino-8-(trans-3-hydroxy-cyclopentyl)-2-methylsulfanyl-8H-pyrido[2,3-d]pyrimidin-7-one

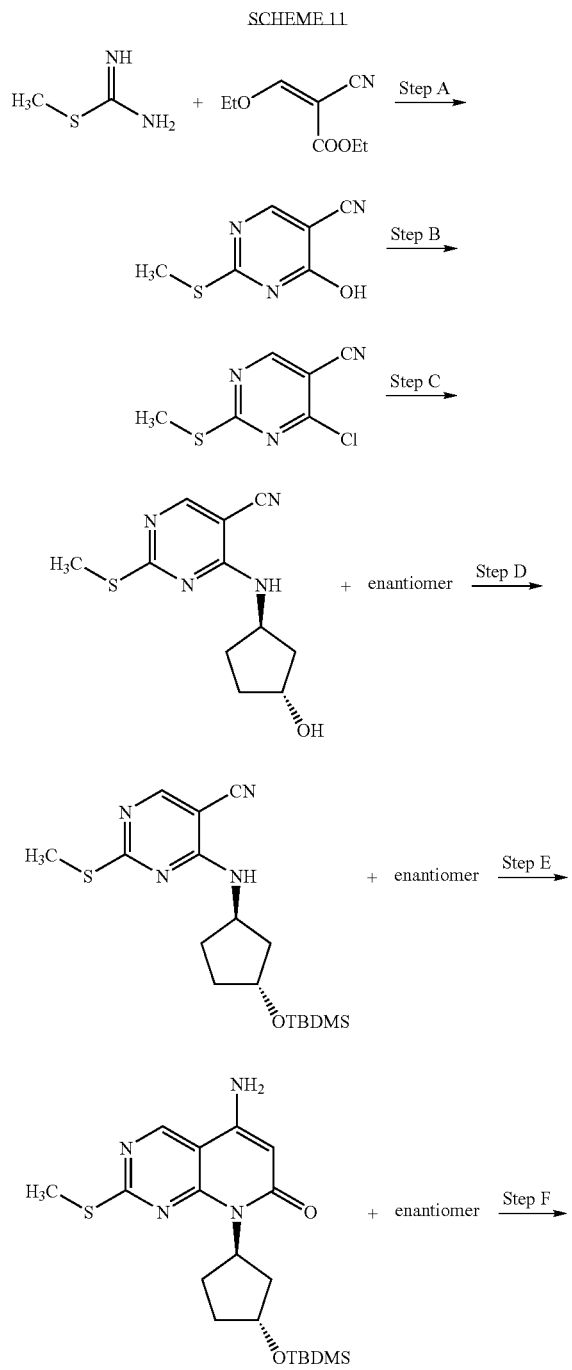

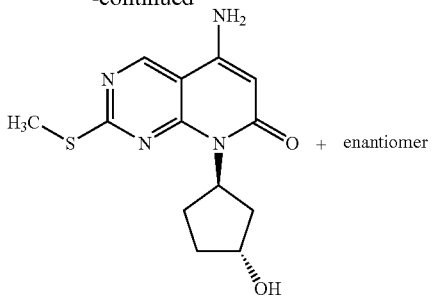

Step A: 2-Methyl-2-thiopseudourea sulfate (17 g) was added to a solution of KOH (9 g) in MeOH (180 mL) previously cooled to 0° C. and the resulting white mixture was stirred for 1 h at RT. The reaction mixture was filtered; the filtrate was maintained at 0° C. and (Z)-2-cyano-3-ethoxy-acrylic acid ethyl ester (33 g) was added as a crushed powder. The bright yellow suspension was stirred at RT for 2 h. The solid was collected by filtration and washed with cold MeOH (2×100 mL) and Et$_2$O (100 mL). The bright yellow solid was added to an aqueous solution of sodium hydroxide (0.5 M, 180 mL) and the resulting mixture was heated at 80° C. for 20 min. The solid was removed by filtration and the filtrate was acidified by addition of HCl (6 M aq). The resulting mixture was allowed to stand for 1 h and the precipitate which formed was collected by filtration to afford after drying in a vacuum oven 11 g of 4-hydroxy-2-methylsulfanyl-pyrimidine-5-carbonitrile as a white solid.

Step B: A mixture of 4-hydroxy-2-methylsulfanyl-pyrimidine-5-carbonitrile (2.76 g) and phosphorus oxychloride (15 mL) was heated at reflux, under argon atmosphere, for 3 h. The reaction mixture was cooled and then evaporated under reduced pressure. Hexane was added to the residue and the mixture was heated at reflux, the resulting mixture was decanted and the same procedure was repeated for 4 times. The combined supernatant layers were evaporated to afford 1.13 g of 4-chloro-2-methylsulfanyl-pyrimidine-5-carbonitrile as a white powder.

Step C: TEA (0.84 mL, 6.04 mmol) was added to a solution of trans-3-amino-cyclopentanol (1.83 g) in anhydrous THF (10 mL), under argon atmosphere. 4-Chloro-2-methylsulfanyl-pyrimidine-5-carbonitrile (1.13 g, 6.04 mmol) was then added in two portions and the resulting mixture was stirred, at RT, under argon atmosphere, for 2 h. The liquid layer was decanted and THF was added to the gummy residue. The extraction procedure was repeated and the combined extracts were evaporated under reduced pressure. The crude residue was absorbed onto silica gel and purified by flash chromatography (EtOAc/hexane) to give 1.0 g of trans-4-(3-hydroxy-cyclopentylamino)-2-methylsulfanyl-pyrimidine-5-carbonitrile.

Step D: To a mixture of trans-4-(3-hydroxy-cyclopentylamino)-2-methylsulfanyl-pyrimidine-5-carbonitrile (500 mg, 2.0 mmol) in anhydrous DMF (15 mL) was added, at RT, under argon atmosphere, imidazole (680 mg, 10.0 mmol) followed by tert-butyldimethylsilylchloride (750 mg, 5.0 mmol) and the resulting mixture was stirred at RT for 64 h. The reaction mixture was quenched with NH$_4$Cl (sat'd aq, 20 mL) and was extracted with EtOAc (3×20 mL). The combined organic layers were washed with water (2×10 mL), dried over Na$_2$SO$_4$, filtered and evaporated under reduced pressure. The crude residue was purified by flash chromatography (hexane/EtOAc, 95/5) to give 660 mg of 4-[trans-3-

(tert-butyl-dimethyl-silanyloxy)-cyclopentylamino]-2-methylsulfanyl-pyrimidine-5-carbonitrile as a white solid.

Step E: Sodium hydride (60% suspension in mineral oil, 303 mg, 7.59 mmol) was added in one portion, under argon atmosphere, to a mixture of 4-[trans-3-(tert-butyl-dimethyl-silanyloxy)-cyclopentylamino]-2-methylsulfanyl-pyrimidine-5-carbonitrile (658 mg, 1.81 mmol) in anhydrous DMF (10 mL) and the resulting mixture was stirred at RT for 30 min. Anhydrous Ac₂O (2.56 mL, 27.1 mmol) was added dropwise, over a period of 35 min, and the reaction mixture was stirred for additional 10 min. The resulting mixture was quenched with NH₄Cl (sat'd aq, 50 mL), and extracted with EtOAc (3×20 mL). The combined organic layers were washed with water (2×10 mL), dried over Na₂SO₄, filtered and evaporated under reduced pressure. The crude residue was dissolved in MeOH (15 mL), and hydrazine hydrate (0.877 mL, 18.08 mmol) was added dropwise. The resulting mixture was heated at 85° C. in a microwave reactor for 50 min. The solvent was evaporated under reduced pressure and water was added to the residue. The resulting mixture was extracted with EtOAc (3×20 mL). The combined organic layers were washed with water (3×10 mL), dried over Na₂SO₄, filtered and evaporated under reduced pressure. The crude residue was purified by flash chromatography (DCM/MeOH) to afford 800 mg of 5-amino-8-[trans-3-(tert-butyl-dimethyl-silanyloxy)-cyclopentyl]-2-methylsulfanyl-8H-pyrido[2,3-d]pyrimidin-7-one.

Step F: A solution of tetrabutylammonium fluoride (1 M in THF, 0.576 mL) was added dropwise, at RT, under argon atmosphere, to a mixture of 5-amino-8-[trans-3-(tert-butyl-dimethyl-silanyloxy)-cyclopentyl]-2-methylsulfanyl-8H-pyrido[2,3-d]pyrimidin-7-one (200 mg, 0.443 mmol) in anhydrous THF (5 mL) and the resulting mixture was stirred overnight. A second aliquot of solution of tetrabutylammonium fluoride (1 M in THF, 0.6 mL) was then added and the reaction mixture was stirred for 2 h. A third aliquot of solution of tetrabutylammonium fluoride (1 M in THF, 1.8 mL) was then added and the reaction mixture was stirred for 2 h. A fourth aliquot of solution of tetrabutylammonium fluoride (1 M in THF, 1.3 mL) was then added and the reaction mixture was stirred overnight. The reaction was quenched with water (20 mL) followed by NH₄Cl (sat'd aq). The resulting mixture was extracted with EtOAc (10×20 mL) and the combined organic extracts were dried over Na₂SO₄, filtered and evaporated under reduced pressure. The crude residue was purified by preparative TLC (DCM/MeOH, 90/10) to give 106 mg (82% yield) of 5-amino-8-(trans-3-hydroxy-cyclopentyl)-2-methylsulfanyl-8H-pyrido[2,3-d]pyrimidin-7-one.

Preparation 12

Synthesis of 5-Amino-8-cyclopentyl-6-methyl-2-methylsulfanyl-8H-pyrido[2,3-d]pyrimidin-7-one

SCHEME 12

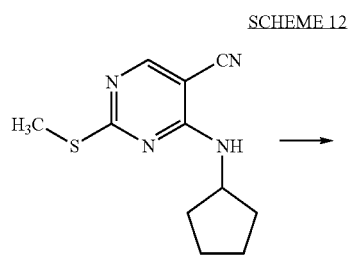

-continued

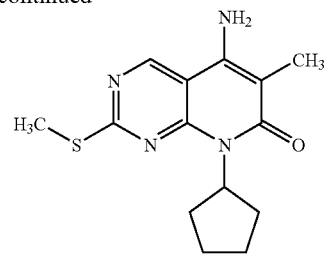

Sodium hydride (60% suspension in mineral oil, 82 mg, 2.05 mmol) was added in one portion, under argon atmosphere, at RT, to a mixture of 4-cyclopentylamino-2-methylsulfanyl-pyrimidine-5-carbonitrile (400 mg, 1.91 mmol) in anhydrous DMF (15 mL) and the resulting mixture was stirred for 30 min, at RT. Propionic anhydride (0.264 mL, 2.05 mmol) was added dropwise, over a period of 40 min, and the resulting mixture was stirred for additional 10 min. The reaction mixture was quenched by addition of a saturated aqueous solution of ammonium chloride (30 mL) and was extracted 3 times with EtOAc (20 mL). The combined organic extracts were washed twice with water (20 mL), dried over Na₂SO₄, filtered and evaporated under reduced pressure. The crude residue was purified by flash chromatography (DCM/MeOH, 95/5) to give 210 mg of 5-amino-8-cyclopentyl-6-methyl-2-methylsulfanyl-8H-pyrido[2,3-d]pyrimidin-7-one.

Preparation 13

Synthesis of trans-5-Amino-8-cyclopentyl-2-(4-hydroxy-cyclohexylamino)-8H-pyrido[2,3-d]pyrimidin-7-one

SCHEME 13

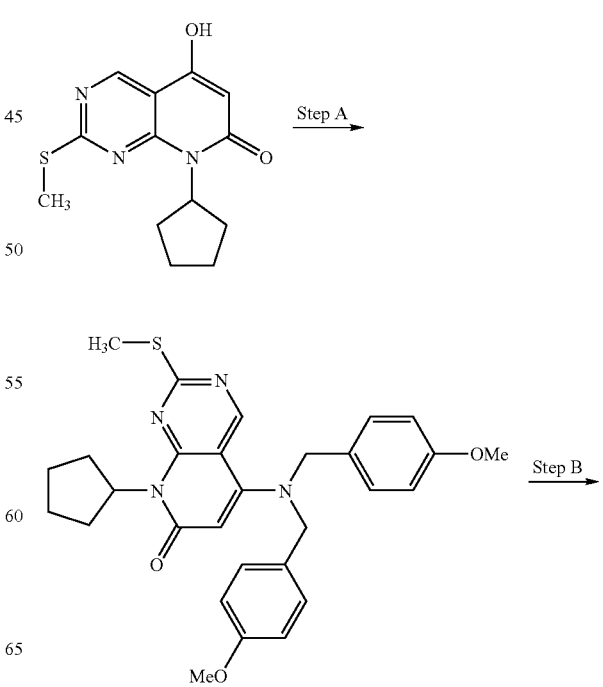

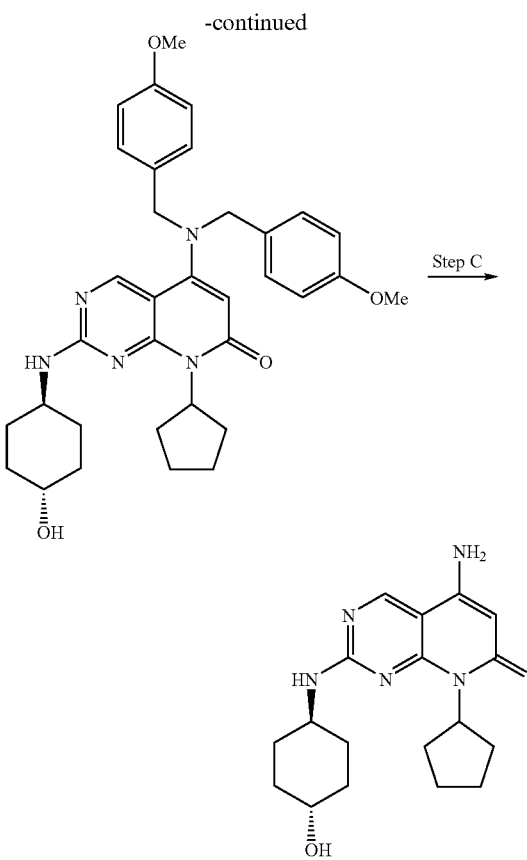

Step A: TEA (1.13 mL, 8.12 mmol) was added to a solution of 8-cyclopentyl-5-hydroxy-2-methylsulfanyl-8H-pyrido[2,3-d]pyrimidin-7-one (1.5 g, 5.41 mmol) in DCM (20 mL), under nitrogen atmosphere. The resulting mixture was cooled to −78° C. and trifluoromethanesulfonic anhydride (1.093 mL, 6.50 mmol) was added, the reaction mixture was then stirred at −78° C. for 1 h. A solution of bis-(4-methoxy-benzyl)-amine (4.14 g, 16.24 mmol) in dichloroethane (20 mL) was added at −78° C., the resulting mixture was stirred at RT for 1 h and was then heated at 100° C. in a microwave reactor for 4 h. The reaction mixture was diluted with DCM and washed 3 times with water. The aqueous layers were combined and extracted 3 times with DCM. The combined organic extracts were dried over $Na_2SO_4$, filtered and evaporated under reduced pressure to give a crude brown oil. This material was purified by flash chromatography (heptane/EtOAc, 100/0 to 80/20) to give 510 mg (18% yield) of 5-[bis-(4-methoxy-benzyl)-amino]-8-cyclopentyl-2-methylsulfanyl-8H-pyrido[2,3-d]pyrimidin-7-one and 1.01 g of trifluoromethanesulfonic acid 8-cyclopentyl-2-methylsulfanyl-7-oxo-7,8-dihydro-pyrido[2,3-d]pyrimidin-5-yl ester.

Step B: OXONE™ (0.759 g, 1.23 mmol) was added at RT to a solution of 5-[bis-(4-methoxy-benzyl)-amino]-8-cyclopentyl-2-methylsulfanyl-8H-pyrido[2,3-d]pyrimidin-7-one (510 mg, 0.988 mmol) in a mixture of acetone (6.6 mL) and water (1.6 mL) and the resulting mixture was stirred at RT for 1 h. The reaction mixture was then diluted with EtOAc and washed 3 times with water. The combined aqueous layers were extracted twice with EtOAc and once with a 1/1 mixture of chloroform and isopropanol. The combined organic extracts were dried over $Na_2SO_4$, filtered and evaporated under reduced pressure to give a 72/28 mixture of 5-[bis-(4-methoxy-benzyl)-amino]-8-cyclopentyl-2-methanesulfinyl-8H-pyrido[2,3-d]pyrimidin-7-one and 5-[bis-(4-methoxy-benzyl)-amino]-8-cyclopentyl-2-methanesulfonyl-8H-pyrido[2,3-d]pyrimidin-7-one. To a solution of this mixture (0.49 mmol) in anhydrous THF (4 mL) was added, at RT, TEA (0.206 mL, 1.482 mmol) followed by trans-aminocyclohexanol (113 mg, 0.988 mmol) and the resulting mixture was stirred at 60° C. for 18 h. The reaction mixture was then diluted with EtOAc and washed 3 times with water. The combined aqueous layers were extracted twice with EtOAc and once with a mixture of chloroform and isopropanol. The combined organic extracts were dried over $Na_2SO_4$, filtered and evaporated under reduced pressure. The crude residue was purified by flash chromatography to give 103 mg of 5-[bis-(4-methoxy-benzyl)-amino]-8-cyclopentyl-2-(4-hydroxy-cyclohexylamino)-8H-pyrido[2,3-d]pyrimidin-7-one.

Step C: Perchloric acid (0.1 mL) was slowly added at RT to a solution of 5-[bis-(4-methoxy-benzyl)-amino]-8-cyclopentyl-2-(4-hydroxy-cyclohexylamino)-8H-pyrido[2,3-d]pyrimidin-7-one (51 mg, 0.087 mmol) in DCM (0.9 mL) and the resulting mixture was stirred at RT for 20 min. The reaction mixture was then diluted with DCM and $NaHCO_3$ (sat'd aq) was slowly added. The organic layer was washed 4 times with $NaHCO_3$ (sat'd aq). The combined aqueous layers were extracted 3 times with DCM and once with a mixture of chloroform and isopropanol. The combined organic extracts were dried over $Na_2SO_4$, filtered and evaporated under reduced pressure. The crude residue was purified by preparative TLC (DCM/MeOH 90/10) to afford 31.9 mg of trans-5-amino-8-cyclopentyl-2-(4-hydroxy-cyclohexylamino)-8H-pyrido[2,3-d]pyrimidin-7-one as a yellow solid. MS=344 [M+H]$^+$; MP=246.5-248.0° C.

Using the above described procedure and the appropriate starting materials, the following compounds were prepared:

trans-5-Amino-2-[4-(morpholine-4-carbonyl)-cyclohexylamino]-8-phenyl-8H-pyrido[2,3-d]pyrimidin-7-one; MS=449.14 [M+H]$^+$;

trans-5-Amino-2-(4-hydroxy-cyclohexylamino)-8-phenyl-8H-pyrido[2,3-d]pyrimidin-7-one; MS=352.14 [M+H]$^+$;

trans-5-Amino-8-cyclopentyl-2-[4-(morpholine-4-carbonyl)-cyclohexylamino]-8H-pyrido[2,3-d]pyrimidin-7-one (yellow solid); MS=441 [M+H]$^+$; MP=292.5-295.3° C.; and 5-Amino-2-cyclohexylamino-8-phenyl-8H-pyrido[2,3-d]pyrimidin-7-one; MS=336.15 [M+H]$^+$.

Preparation 14

Synthesis of 5-Amino-2-(4,4-difluoro-cyclohexylamino)-8-methyl-8H-pyrido[2,3-d]pyrimidin-7-one

SCHEME 14

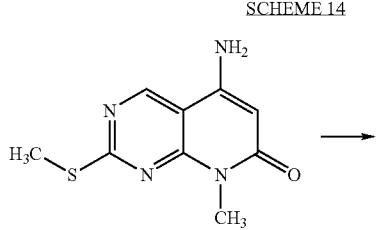

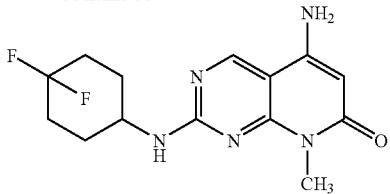

To a solution of 5-amino-8-methyl-2-methylsulfanyl-8H-pyrido[2,3-d]pyrimidin-7-one (163 mg, 0.733 mmol) in DCM (200 mL) was added 3-chloroperoxybenzoic acid (77% max., 164 mg, 0.733 mmol) at RT and the resulting mixture was stirred for 1 h. The reaction mixture was then evaporated under reduced pressure and the residue was dissolved in anhydrous dimethyl sulfoxide (7.3 mL). To a portion of this solution (1.8 mL) was added TEA (0.13 mL, 0.90 mmol), followed by 4,4-difluorocyclohexylamine hydrochloride (62 mg, 0.36 mmol) at RT. The reaction mixture was stirred at 80° C. for 4.5 h and was then quenched with water. The resulting mixture was extracted twice with EtOAc (20 mL). The combined organic layers were washed with brine, dried over MgSO$_4$, filtered and evaporated under reduced pressure. The crude residue was purified by flash chromatography (from 0 to >10% of MeOH/DCM in 10 min.) to give 27 mg (49% yield) of 5-amino-2-(4,4-difluoro-cyclohexylamino)-8-methyl-8H-pyrido[2,3-d]pyrimidin-7-one as a yellow solid. MS=310 [M+H]$^+$.

Using the above described procedure and the appropriate starting materials, the following compounds were prepared:

trans-5-Amino-2-(4-hydroxy-cyclohexylamino)-8-methyl-8H-pyrido[2,3-d]pyrimidin-7-one (yellow solid); MS=290 [M+H]$^+$;

5-Amino-2-cyclohexylamino-8-ethyl-8H-pyrido[2,3-d]pyrimidin-7-one (brown solid); MS=288 [M+H]$^+$; MP=147.7-150.1° C.;

5-Amino-8-cyclopentyl-2-(tetrahydro-pyran-4-ylamino)-8H-pyrido[2,3-d]pyrimidin-7-one (off-white solid); MS=330 [M+H]$^+$; MP=120.0-124.0° C.;

5-Amino-2-cyclohexylamino-8-cyclopentyl-8H-pyrido[2,3-d]pyrimidin-7-one (yellow solid); MS=328 [M+H]$^+$; MP=125.0-130.0° C.;

trans-5-Amino-8-cyclohexyl-2-(4-hydroxy-cyclohexylamino)-8H-pyrido[2,3-d]pyrimidin-7-one (light brown powder); MS=358 [M+H]$^+$; MP=292.0-294.0° C.;

trans-5-Amino-8-cyclohexyl-2-[4-(morpholine-4-carbonyl)-cyclohexylamino]-8H-pyrido[2,3-d]pyrimidin-7-one (yellow powder); MS=455 [M+H]$^+$; MP=185.0-203.0° C.;

5-Amino-8-cyclohexyl-2-cyclohexylamino-8H-pyrido[2,3-d]pyrimidin-7-one (off-white powder); MS=342 [M+H]$^+$; MP=243.1-244.9° C.;

trans-N-[4-(5-Amino-8-cyclohexyl-7-oxo-7,8-dihydro-pyrido[2,3-d]pyrimidin-2-ylamino)-cyclohexyl]-acetamide (light yellow solid); MS=399 [M+H]$^+$;

trans-5-Amino-8-cyclohexyl-2-(1-methanesulfonyl-piperidin-4-ylamino)-8H-pyrido[2,3-d]pyrimidin-7-one (light brown powder); MS=421 [M+H]$^+$; MP=250.0-254.0° C.;

trans-[4-(5-Amino-8-cyclohexyl-7-oxo-7,8-dihydro-pyrido[2,3-d]pyrimidin-2-ylamino)-cyclohexyl]-carbamic acid methyl ester (brown powder); MS=415 [M+H]$^+$; MP=193.9-198.0° C.;

5-Amino-8-cyclohexyl-2-(tetrahydro-pyran-4-ylamino)-8H-pyrido[2,3-d]pyrimidin-7-one (light yellow powder); MS=344 [M+H]$^+$; MP=160.0-164.0° C.;

2-(1-Acetyl-piperidin-4-ylamino)-5-amino-8-cyclohexyl-8H-pyrido[2,3-d]pyrimidin-7-one (brown waxy solid); MS=385 [M+H]$^+$;

5-Amino-8-cyclohexyl-2-(4,4-difluoro-cyclohexylamino)-8H-pyrido[2,3-d]pyrimidin-7-one (light yellow powder); MS=378 [M+H]$^+$; MP=240.0-244.1° C.;

cis-N-[4-(5-Amino-8-cyclopentyl-7-oxo-7,8-dihydro-pyrido[2,3-d]pyrimidin-2-ylamino)-cyclohexyl]-acetamide (off-white solid); MS=385 [M+H]$^+$; MP=172.6-176.6° C.;

5-Amino-8-cyclopropylmethyl-2-(tetrahydro-pyran-4-ylamino)-8H-pyrido[2,3-d]pyrimidin-7-one (off-white solid); MS=316 [M+H]$^+$; MP=135.0-137.4° C.;

5-Amino-8-benzyl-2-cyclohexylamino-8H-pyrido[2,3-d]pyrimidin-7-one (off-white solid); MS=350 [M+H]$^+$; MP=221.9-223.8° C.;

5-Amino-8-benzyl-2-(tetrahydro-pyran-4-ylamino)-8H-pyrido[2,3-d]pyrimidin-7-one (off-white solid); MS=352 [M+H]$^+$; MP=245.6-246.8° C.;

5-Amino-2-cyclohexylamino-8-cyclopropylmethyl-8H-pyrido[2,3-d]pyrimidin-7-one (off-white solid); MS=314 [M+H]$^+$; MP=133.0-135.0° C.;

5-Amino-2-cyclobutylamino-8-cyclopropylmethyl-8H-pyrido[2,3-d]pyrimidin-7-one (off-white solid); MS=286 [M+H]$^+$; MP=236.1-239.1° C.;

trans-5-Amino-8-cyclopropyl-2-(4-hydroxy-cyclohexylamino)-8H-pyrido[2,3-d]pyrimidin-7-one (light yellow powder); MS=315 [M]; MP=256.3-258.7° C.;

5-Amino-2-cyclohexylamino-8-cyclopropyl-8H-pyrido[2,3-d]pyrimidin-7-one (light brown solid); MS=299 [M]; MP=117.0-118.0° C.;

[4-(5-Amino-8-cyclopropyl-7-oxo-7,8-dihydro-pyrido[2,3-d]pyrimidin-2-ylamino)-cyclohexyl]-carbamic acid methyl ester (off-white powder); MS=372 [M]; MP=257.0-259.0° C.;

5-Amino-8-cyclopropyl-2-(tetrahydro-pyran-4-ylamino)-8H-pyrido[2,3-d]pyrimidin-7-one (off-white powder); MS=301 [M]; MP=264.4-266.8° C.;

5-Amino-8-cyclopropyl-2-(1-methanesulfonyl-piperidin-4-ylamino)-8H-pyrido[2,3-d]pyrimidin-7-one (light brown solid); MS=378 [M]; MP=224.5-226.0° C.;

5-Amino-8-cyclobutyl-2-cyclohexylamino-8H-pyrido[2,3-d]pyrimidin-7-one (off-white solid); MS=313 [M]; MP=120-121.5° C.;

[4-(5-Amino-8-cyclobutyl-7-oxo-7,8-dihydro-pyrido[2,3-d]pyrimidin-2-ylamino)-cyclohexyl]-carbamic acid methyl ester (off-white solid); MS=387 [M]; MP=154.3-156.0° C.;

(4-{5-Amino-8-[3-(tert-butyl-dimethyl-silanyloxy)-propyl]-7-oxo-7,8-dihydro-pyrido[2,3-d]pyrimidin-2-ylamino}-cyclohexyl)-carbamic acid methyl ester;

2-(1-Acetyl-piperidin-4-ylamino)-5-amino-8-(trans-3-hydroxy-cyclopentyl)-8H-pyrido[2,3-d]pyrimidin-7-one (yellow powder); MS=387 [M+H]$^+$; MP=192.0-194.0° C.;

N-{4-[5-Amino-8-(trans-3-hydroxy-cyclopentyl)-7-oxo-7,8-dihydro-pyrido[2,3-d]pyrimidin-2-ylamino]-cyclohexyl}-acetamide (yellow powder); MS=401 [M+H]$^+$; MP=210.0-211.5° C.;

5-Amino-2-cyclohexylamino-8-(trans-3-hydroxy-cyclopentyl)-8H-pyrido[2,3-d]pyrimidin-7-one (yellow powder); MS=344 [M+H]$^+$; MP=169.5-170.0° C.;

5-Amino-8-cyclopentyl-6-methyl-2-[4-(morpholine-4-carbonyl)-cyclohexylamino]-8H-pyrido[2,3-d]pyrimidin-7-one (light yellow powder); MS=455 [M+H]$^+$; MP=186.8-188.0° C.;

N-[4-(5-Amino-8-cyclopentyl-6-methyl-7-oxo-7,8-dihydro-pyrido[2,3-d]pyrimidin-2-ylamino)-cyclohexyl]-acetamide (yellow powder); MS=399 [M+H]⁺; MP=296.2-298.2° C.; and 2-(1-Acetyl-piperidin-4-ylamino)-5-amino-8-cyclopentyl-6-methyl-8H-pyrido[2,3-d]pyrimidin-7-one (light brown powder); MS=385 [M+H]⁺; MP=281.0-283.0° C.

Preparation 15

Synthesis of 5-Amino-2-cyclohexylamino-8-(3-hydroxy-propyl)-8H-pyrido[2,3-d]pyrimidin-7-one

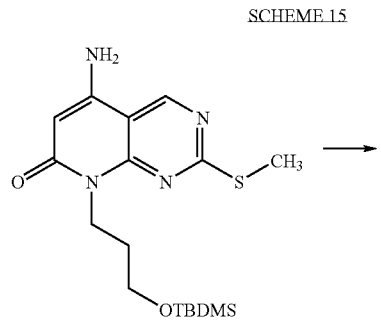

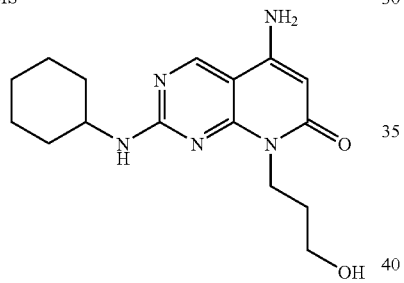

To a solution of 5-amino-8-[3-(tert-butyl-dimethyl-silanyloxy)-propyl]-2-methylsulfanyl-8H-pyrido[2,3-d]pyrimidin-7-one (150 mg, 0.395 mmol) in DCM (9 mL) was added 3-chloroperoxybenzoic acid (77% max., 106 mg, 0.474 mmol) at RT under argon atmosphere and the resulting mixture was stirred for 40 min. The reaction mixture was then evaporated under reduced pressure and the residue was dissolved in anhydrous dimethyl sulfoxide (ca. 9 mL). Cyclohexylamine (0.226 mL, 1.975 mmol) was then added at RT and the resulting mixture was stirred at 80° C. for 1.5 h. The reaction mixture was then quenched with water (70 mL) and an aqueous saturated solution of ammonium chloride (30 mL). The resulting mixture was extracted with EtOAc; the organic extracts were washed twice with water (50 mL), dried over MgSO₄, filtered and evaporated under reduced pressure. To the residue, dissolved in THF, was added a solution of tetrabutylammonium fluoride (1 M in THF, 0.59 mL) at RT and the resulting mixture was stirred overnight. The solid formed was collected by filtration, washed with hexane and purified by preparative TLC (DCM/MeOH, 90/10) to give 30 mg of 5-amino-2-cyclohexylamino-8-(3-hydroxy-propyl)-8H-pyrido[2,3-d]pyrimidin-7-one as a yellow powder. MS=318 [M+H]⁺; MP=131.0-132.5° C.

Preparation 16

Synthesis of {4-[5-Amino-8-(3-hydroxy-propyl)-7-oxo-7,8-dihydro-pyrido[2,3-d]pyrimidin-2-ylamino]-cyclohexyl}-carbamic acid methyl ester

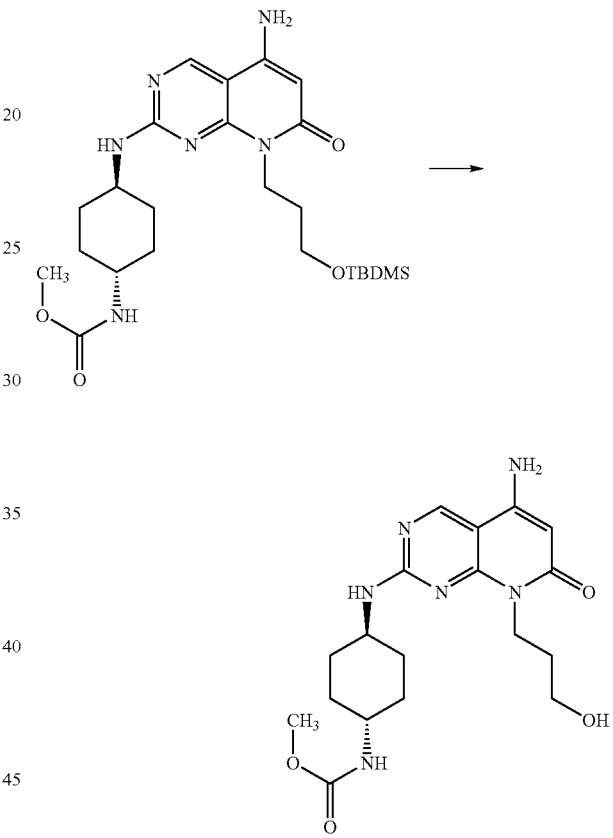

(4-{5-Amino-8-[3-(tert-butyl-dimethyl-silanyloxy)-propyl]-7-oxo-7,8-dihydro-pyrido[2,3-d]pyrimidin-2-ylamino}-cyclohexyl)-carbamic acid methyl ester (prepared as described in Example 2) (0.280 mmol) was dissolved in a mixture of glacial acetic acid, THF and water (3/1/1, 25 mL) and the resulting mixture was stirred at RT overnight. The reaction mixture was concentrated under reduced pressure and the crude residue was purified by preparative TLC (MeOH/DCM, 15/85) to give 11 mg of {4-[5-amino-8-(3-hydroxy-propyl)-7-oxo-7,8-dihydro-pyrido[2,3-d]pyrimidin-2-ylamino]-cyclohexyl}-carbamic acid methyl ester as a yellow powder. MS=391 [M+H]⁺; MP=190.0-191.0° C.

N-{4-[5-Amino-8-(3-hydroxy-propyl)-7-oxo-7,8-dihydro-pyrido[2,3-d]pyrimidin-2-ylamino]-cyclohexyl}-acetamide (yellow powder) was prepared using the above described procedure and the appropriate starting materials. MS=375 [M+H]+; MP>300° C.

Preparation 17

Synthesis of 5-amino-6-cyano-8-cyclobutyl-2-methylsulfanyl-8H-pyrido[2,3-d]pyrimidin-7-one

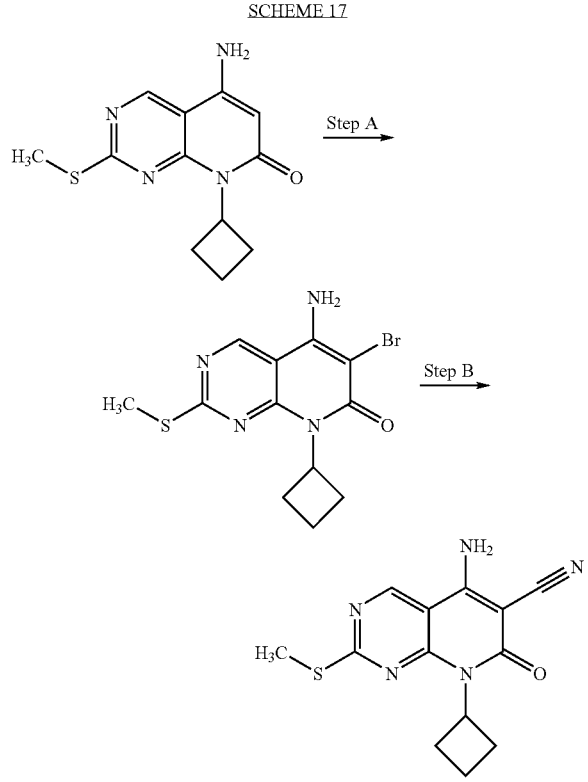

Step A: To a mixture of 5-amino-8-cyclobutyl-2-methylsulfanyl-8H-pyrido[2,3-d]pyrimidin-7-one (1.3 g, 4.46 mmol) in DCM (120 mL) at 0° C. was added N-bromosuccinimide (0.87 g, 4.9 mmol) in 5 portions over 5 min. After stirring for 30 min, the DCM was evaporated under reduced pressure and the residue treated with 100 mL water and 100 mL NaHCO3 (sat'd, aq). The crude product was extracted into EtOAc (2×100 mL). The combined organic layers were washed with NaHCO3 (4×60 mL) and water (2×50 mL) and evaporated under reduced pressure to give 1.3 g of 5-amino-6-bromo-8-cyclobutyl-2-methylsulfanyl-8H-pyrido[2,3-d]pyrimidin-7-one as a brown solid.

Step B: To a solution of 5-amino-6-bromo-8-cyclobutyl-2-methylsulfanyl-8H-pyrido[2,3-d]pyrimidin-7-one (50 mg, 0.15 mmol) in 0.5 mL NMP was added copper(I) cyanide (56 mg, 0.63 mmol). The resulting mixture was heated at 220° C. in a microwave reactor for 20 min. After cooling, the reaction mixture was treated with a mixture of NaHCO3 (sat'd, aq) and EtOAc. The mixture was filtered and the collected solid then mixed with NH4OH (15%, aq). The aqueous mixture was extracted with EtOAc and then combined organic layers and evaporated under reduced pressure. The crude residue was purified by preparative TLC (DCM/MeOH, 93/7) to give 29 mg of 5-amino-6-cyano-8-cyclobutyl-2-methylsulfanyl-8H-pyrido[2,3-d]pyrimidin-7-one as a solid.

Preparation 18

Synthesis of 5-amino-8-cyclobutyl-2-methylsulfanyl-6-phenyl-8H-pyrido[2,3-d]pyrimidin-7-one

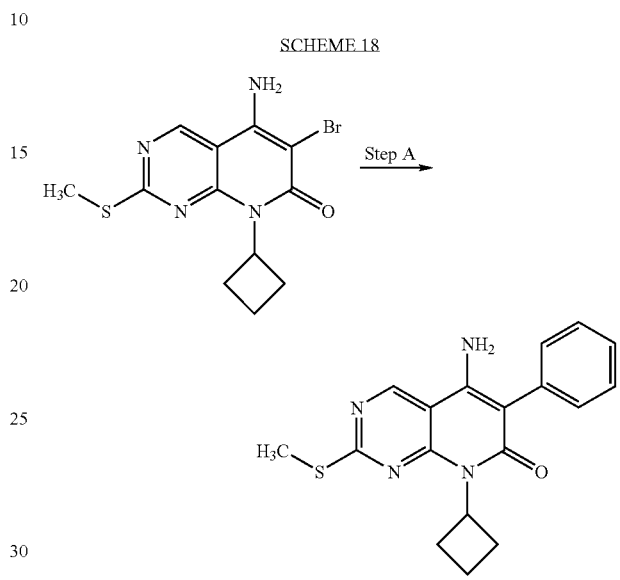

Step A: To a mixture of 5-amino-6-bromo-8-cyclobutyl-2-methylsulfanyl-8H-pyrido[2,3-d]pyrimidin-7-one (50 mg, 0.15 mmol), phenylboronic acid (28 mg, 0.22 mmol), tetrakis(triphenylphosphine)palladium(0) (17 mg, 0.015 mmol) in 0.6 mL toluene and 0.6 mL EtOH was added cesium carbonate (0.17 g, 0.52 mmol). The resulting mixture was heated at 100° C. in a microwave reactor for 30 min. The reaction mixture was cooled, NaHCO3 (sat'd aq) added and the mixture extracted with EtOAc (3×20 mL). The combined organic layers were washed with water (2×10 mL) and evaporated under reduced pressure. The crude residue was purified by preparative TLC (Hexanes:EtOAc, 2:1) to afford 40 mg of 5-amino-8-cyclobutyl-2-methylsulfanyl-6-phenyl-8H-pyrido[2,3-d]pyrimidin-7-one as a solid.

Biological Assays

Example 1

JNK Assay In Vitro

JNK activity was measured by phosphorylation of GST-ATF2 (19-96) with [γ-33P] ATP. The enzyme reaction was conducted at Km concentrations of ATP and the substrate at final volume of 40 μl in buffer containing 25 mM HEPES, pH 7.5, 2 mM dithiothreitol, 150 mM NaCl, 20 mM MgCl2, 0.001% Tween® 20, 0.1% BSA and 10% DMSO. Human JNK2α2 assay contains 1 nM enzyme, 1 μM ATF2, 8 μM ATP with 1 uCi [γ-33P] ATP. Human JNK1α1 assay contains 2 nM enzyme, 1 μM ATF2, 6 μM ATP with 1 μCi [γ-33P] ATP. Human JNK3 (Upstate Biotech #14-501M) assay contains 2 nM enzyme, 1 μM ATF2, 4 μM ATP with 1 μCi [γ-33P] ATP. The enzyme assay was carried out in the presence or absence of several compound concentrations. JNK and compound were pre-incubated for 10 min., followed by initiation of the enzymatic reaction by adding ATP and the substrate. The reaction mixture was incubated at 30° C. for 30 min. At the end of incubation, the reaction was terminated by transferring 25 μl of the reaction mixture to 150 μl of 10% glutathione Sepharose® slurry (Amersham #27-4574-01) containing 135 mM EDTA. The reaction product was captured on the affinity resin, and washed on a filtration plate (Millipore, MAB-VNOB50) with phosphate buffered saline for six times to remove free radionucleotide. The incorporation of $^{33}$P into ATF2 was quantified on a microplate scintillation counter (Packard Topcount). Compound inhibition potency on JNK was measured by $IC_{50}$ value generated from ten concentration inhibition curves fitted into the 3-parameter model: % inhibition=Maximum/(1+($IC_{50}$/[Inhibitor])$^{slope}$). Data were analyzed on Microsoft Excel for parameter estimation. Representative results are shown in Table Y below:

TABLE Y

Representative Compound $IC_{50}$'s for JNK1 and JNK2

| Compound | JNK1 (μM) | JNK2 (μM) |
|---|---|---|
| I-1 | 0.0111 | 0.0258 |
| I-3 | 0.0179 | 0.0403 |
| I-5 | 0.0205 | 0.0439 |
| I-7 | 0.0316 | 0.0397 |
| I-9 | 0.0344 | 0.0377 |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed:
1. A compound of formula I

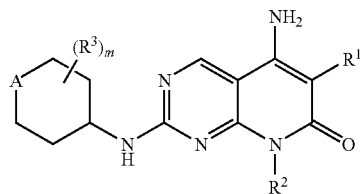

including enantiomers, diastereomers, racemic mixtures and pharmaceutically acceptable salts thereof, wherein:
$R^1$ is $R^{1a}$ or $R^{1b}$;
  $R^{1a}$ is H, halo, acyl, lower alkyl, lower haloalkyl, lower alkoxy, —CN, or —OH;
  $R^{1b}$ K is cycloalkyl, heterocycloalkyl, or phenyl, optionally substituted with one or more $R^{1b'}$;
    each $R^{1b'}$ is independently halo, —OH, lower alkoxy, amino, lower alkyl or lower haloalkyl;
$R^2$ is lower alkyl, lower heteroalkyl, lower alkoxy, cycloalkyl, phenyl, heterocycloalkyl, or heteroaryl, optionally substituted with one or more $R^{2a}$;
  each $R^{2a}$ is independently —OH, halo, lower alkyl, amino, lower alkoxy, or $R^{2b}$;
    $R^{2b}$ is cycloalkyl, heterocycloalkyl, or phenyl, optionally substituted with one or more $R^{2b'}$;
      each $R^{2b'}$ is independently halo, —OH, lower alkoxy, amino, lower alkyl or lower haloalkyl;
$R^3$ is halo, amino, lower alkyl, lower alkoxy, or lower haloalkyl;
A is O or A';
  A' is $C(R^5)(R^{5'})$ or $N(R^{5b})$;
    $R^5$ and $R^{5'}$ are independently $R^{5a}$ or $R^{5b}$;
      $R^{5a}$ is —H, halo, —OH, or A";
      $R^{5b}$ is lower alkyl, A", or lower heteroalkyl, optionally substituted with one or more $R^{6a}$;
        $R^{6a}$ is —OH, halo, lower alkyl, lower haloalkyl, lower alkoxy, or amino;
A" is —NHC(=O)$R^7$, —NHC(=O)O$R^7$, —N($R^9$)S(=O)$_2R^7$, —S(=O)$_2R^7$, —C(=O)$R^8$, or —C(=O)O$R^7$;
  $R^7$ is lower alkyl or cycloalkyl;
  $R^8$ is cycloalkyl, cycloalkyl lower alkyl, heterocycloalkyl, heterocycloalkyl lower alkyl, or lower alkyl, each of which may be optionally substituted with halo, —OH, lower alkoxy, amino, or lower alkyl;
  $R^9$ is H or lower alkyl; and
m is 0 to 4.

2. A compound of formula II

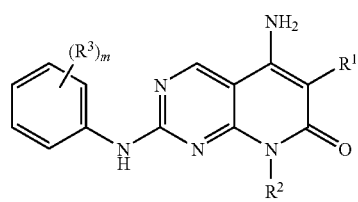

including enantiomers, diastereomers, racemic mixtures and pharmaceutically acceptable salts thereof, wherein:
$R^1$ is $R^{1a}$ or $R^{1b}$;
  $R^{1a}$ is H, halo, lower alkyl, lower haloalkyl, lower alkoxy, —CN, or —OH;
  $R^{1b}$ is cycloalkyl, heterocycloalkyl, or phenyl, optionally substituted with one or more $R^{1b'}$
    each $R^{1b'}$ is independently halo, —OH, lower alkoxy, amino, lower alkyl or lower haloalkyl;
$R^2$ is lower alkyl, lower heteroalkyl, alkoxy, cycloalkyl, phenyl, heterocycloalkyl, or heteroaryl, optionally substituted with one or more $R^{2a}$;
  each $R^{2a}$ is independently —OH, halo, lower alkyl, amino, lower alkoxy, or $R^{2b}$;
    $R^{2b}$ is cycloalkyl, heterocycloalkyl, or phenyl, optionally substituted with one or more $R^{2b'}$;
      each $R^{2b'}$ is independently halo, —OH, lower alkoxy, amino, lower alkyl or lower haloalkyl;
$R^3$ is H, halo, amino, lower alkyl, lower alkoxy, or lower haloalkyl; and
m is 0-5.

3. A compound of formula III

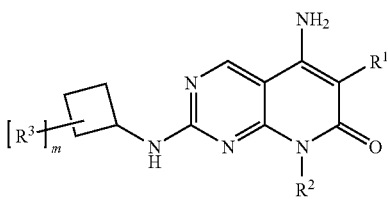

including enantiomers, diastereomers, racemic mixtures and pharmaceutically acceptable salts thereof, wherein:
$R^1$ is $R^{1a}$ or $R^{1b}$;
  $R^{1a}$ is H, halo, lower alkyl, lower haloalkyl, lower alkoxy, —CN, or —OH;
  $R^{1b}$ is cycloalkyl, heterocycloalkyl, or phenyl, optionally substituted with one or more $R^{1b'}$;
    each $R^{1b'}$ is independently halo, —OH, lower alkoxy, amino, lower alkyl or lower haloalkyl;
$R^2$ is lower alkyl, lower heteroalkyl, lower alkoxy, cycloalkyl, phenyl, heterocycloalkyl, or heteroaryl, optionally substituted with one or more $R^{2a}$;
  each $R^{2a}$ is independently —OH, halo, lower alkyl, amino, lower alkoxy, or $R^{2b}$;
    $R^{2b}$ is cycloalkyl, heterocycloalkyl, or phenyl, optionally substituted with one or more $R^{2b'}$;
      each $R^{2b'}$ is independently halo, —OH, lower alkoxy, amino, lower alkyl or lower haloalkyl;
$R^3$ is halo, amino, lower alkyl, lower alkoxy, or lower haloalkyl; and
m is 0 to 3.

4. A compound selected from the group consisting of:
5-Amino-2-cyclohexylamino-8-((1R,3R)-3-hydroxy-cyclopentyl)-8H-pyrido[2,3-d]pyrimidin-7-one;
[4-(5-Amino-8-cyclobutyl-7-oxo-7,8-dihydro-pyrido[2,3-d]pyrimidin-2-ylamino)-cyclohexyl]-carbamic acid methyl ester;
5-Amino-8-cyclobutyl-2-cyclohexylamino-8H-pyrido[2,3-d]pyrimidin-7-one;
5-Amino-8-cyclobutyl-2-cyclohexylamino-6-fluoro-8H-pyrido[2,3-d]pyrimidin-7-one;
5-Amino-8-cyclopentyl-2-(4-hydroxy-cyclohexylamino)-8H-pyrido[2,3-d]pyrimidin-7-one;
5-Amino-8-cyclohexyl-2-(4-hydroxy-cyclohexylamino)-8H-pyrido[2,3-d]pyrimidin-7-one;
5-Amino-8-cyclohexyl-2-[4-(morpholine-4-carbonyl)-cyclohexylamino]-8H-pyrido[2,3-d]pyrimidin-7-one;
5-Amino-2-cyclohexylamino-8-(3-hydroxy-propyl)-8H-pyrido[2,3-d]pyrimidin-7-one;
5-Amino-8-cyclobutyl-6-methyl-2-[4-(pyrrolidine-1-carbonyl)-cyclohexylamino]-8H-pyrido[2,3-D]pyrimidin-7-one;
5-Amino-8-cyclopentyl-6-methyl-2-[4-(morpholine-4-carbonyl)-cyclohexylamino]-8H-pyrido[2,3-d]pyrimidin-7-one;
N-[4-(5-Amino-8-cyclopentyl-7-oxo-7,8-dihydro-pyrido[2,3-d]pyrimidin-2-ylamino)-cyclohexyl]-acetamide;
5-Amino-2-cyclohexylamino-8-cyclopropylmethyl-8H-pyrido[2,3-d]pyrimidin-7-one;
5-Amino-8-cyclopentyl-2-[4-(morpholine-4-carbonyl)-cyclohexylamino]-8H-pyrido[2,3-D]pyrimidin-7-one;
N-[4-(5-Amino-8-cyclohexyl-7-oxo-7,8-dihydro-pyrido[2,3-d]pyrimidin-2-ylamino)-cyclohexyl]-methanesulfonamide;
5-Amino-8-cyclobutyl-2-[4-(4-hydroxy-piperidine-1-carbonyl)-cyclohexylamino]-6-methyl-8H-pyrido[2,3-d]pyrimidin-7-one;
5-Amino-6-(2-chloro-phenyl)-8-cyclobutyl-2-cyclohexylamino-8H-pyrido[2,3-d]pyrimidin-7-one;
5-Amino-2-cyclohexylamino-8-cyclopentyl-8H-pyrido[2,3-d]pyrimidin-7-one;
N-{4-[5-Amino-8-((1R,3R)-3-hydroxy-cyclopentyl)-7-oxo-7,8-dihydro-pyrido[2,3-d]pyrimidin-2-ylamino]-cyclohexyl}-acetamide;
[4-(5-Amino-8-cyclohexyl-7-oxo-7,8-dihydro-pyrido[2,3-d]pyrimidin-2-ylamino)-cyclohexyl]-carbamic acid methyl ester;
5-Amino-8-cyclobutyl-2-[4-(1-hydroxy-1-methyl-ethyl)-cyclohexylamino]-6-methyl-8H-pyrido[2,3-d]pyrimidin-7-one;
5-Amino-2-cyclohexylamino-8-ethyl-8H-pyrido[2,3-d]pyrimidin-7-one;
5-Amino-8-cyclopropyl-2-(4-hydroxy-cyclohexylamino)-8H-pyrido[2,3-d]pyrimidin-7-one;
N-[4-(5-Amino-8-cyclopentyl-6-ethyl-7-oxo-7,8-dihydro-pyrido[2,3-d]pyrimidin-2-ylamino)-cyclohexyl]-acetamide;
N-[4-(5-Amino-8-cyclobutyl-6-methyl-7-oxo-7,8-dihydro-pyrido[2,3-d]pyrimidin-2-ylamino)-cyclohexyl]-N-methyl-methanesulfonamide;
5-Amino-8-cyclobutyl-2-[4-(4-hydroxy-piperidine-1-carbonyl)-cyclohexylamino]-6-isopropyl-8H-pyrido[2,3-d]pyrimidin-7-one;
5-Amino-2-cyclohexylamino-8-cyclopropyl-8H-pyrido[2,3-d]pyrimidin-7-one;
5-Amino-8-cyclopropyl-2-(1-methanesulfonyl-piperidin-4-ylamino)-8H-pyrido[2,3-d]pyrimidin-7-one;
N-[4-(5-Amino-8-cyclohexyl-7-oxo-7,8-dihydro-pyrido[2,3-d]pyrimidin-2-ylamino)-cyclohexyl]-acetamide;
5-Amino-8-cyclohexyl-2-(1-methanesulfonyl-piperidin-4-ylamino)-8H-pyrido[2,3-d]pyrimidin-7-one;
2-(1-Acetyl-piperidin-4-ylamino)-5-amino-8-cyclopentyl-8H-pyrido[2,3-d]pyrimidin-7-one;
5-Amino-8-cyclobutyl-2-cyclohexylamino-6-phenyl-8H-pyrido[2,3-d]pyrimidin-7-one;
5-Amino-8-cyclohexyl-2-cyclohexylamino-8H-pyrido[2,3-d]pyrimidin-7-one;
5-Amino-8-cyclopentyl-2-(tetrahydro-pyran-4-ylamino)-8H-pyrido[2,3-d]pyrimidin-7-one;
5-Amino-8-cyclobutyl-6-methyl-2-((1R,2R)-2-methyl-cyclohexylamino)-8H-pyrido[2,3-d]pyrimidin-7-one;
5-Amino-6-bromo-8-cyclobutyl-2-cyclohexylamino-8H-pyrido[2,3-d]pyrimidin-7-on d]pyrimidin-7-one;
5-Amino-2-cyclohexylamino-8-cyclopentyl-6-ethyl-8H-pyrido[2,3-d]pyrimidin-7-one;
2-(1-Acetyl-piperidin-4-ylamino)-5-amino-8-((1R,3R)-3-hydroxy-cyclopentyl)-8H-pyrido[2,3-d]pyrimidin-7-one;
5-Amino-8-cyclobutyl-2-[4-(4-hydroxy-piperidine-1-carbonyl)-cyclohexylamino]-7-oxo-7,8-dihydro-pyrido[2,3-d]pyrimidine-6-carbonitrile;
[4-(5-Amino-8-cyclopropyl-7-oxo-7,8-dihydro-pyrido[2,3-d]pyrimidin-2-ylamino)-cyclohexyl]-carbamic acid methyl ester;
5-Amino-8-cyclobutyl-2-(1-methanesulfonyl-piperidin-4-ylamino)-6-methyl-8H-pyrido[2,3-d]pyrimidin-7-one;
N-[4-(5-Amino-8-cyclopentyl-6-methyl-7-oxo-7,8-dihydro-pyrido[2,3-d]pyrimidin-2-ylamino)-cyclohexyl]-acetamide;

N-{4-[5-Amino-8-(3-hydroxy-propyl)-7-oxo-7,8-dihydro-pyrido[2,3-d]pyrimidin-2-ylamino]-cyclohexyl}-acetamide;
{4-[5-Amino-8-(3-hydroxy-propyl)-7-oxo-7,8-dihydro-pyrido[2,3-d]pyrimidin-2-ylamino]-cyclohexyl}-carbamic acid methyl ester;
5-Amino-2-cyclohexylamino-6-methyl-8-(R)-tetrahydro-furan-3-yl-8H-pyrido[2,3-d]pyrimidin-7-one;
5-Amino-8-cyclopentyl-2-phenylamino-8H-pyrido[2,3-d]pyrimidin-7-one;
5-Amino-8-cyclopropylmethyl-2-(tetrahydro-pyran-4-ylamino)-8H-pyrido[2,3-d]pyrimidin-7-one;
5-Amino-2-[4-(4-hydroxy-piperidine-1-carbonyl)-cyclohexylamino]-6-methyl-8-(R)-tetrahydro-furan-3-yl-8H-pyrido[2,3-d]pyrimidin-7-one;
5-Amino-2-(4-hydroxy-cyclohexylamino)-8-methyl-8H-pyrido[2,3-d]pyrimidin-7-one;
5-Amino-8-cyclobutyl-2-cyclohexylamino-6-isopropyl-8H-pyrido[2,3-d]pyrimidin-7-one;
5-Amino-8-ethyl-2-(tetrahydro-pyran-4-ylamino)-8H-pyrido[2,3-d]pyrimidin-7-one;
5-Amino-8-cyclohexyl-2-(tetrahydro-pyran-4-ylamino)-8H-pyrido[2,3-d]pyrimidin-7-one;
5-Amino-8-cyclobutyl-2-cyclohexylamino-7-oxo-7,8-dihydro-pyrido[2,3-d]pyrimidine-6-carbonitrile;
5-Amino-2-(1-methanesulfonyl-piperidin-4-ylamino)-6-methyl-8-(R)-tetrahydro-furan-3-yl-8H-pyrido[2,3-d]pyrimidin-7-one;
5-Amino-8-cyclopropyl-2-(tetrahydro-pyran-4-ylamino)-8H-pyrido[2,3-d]pyrimidin-7-one;
5-Amino-2-cyclobutylamino-8-cyclopropylmethyl-8H-pyrido[2,3-d]pyrimidin-7-one;
4-(5-Amino-8-cyclobutyl-6-methyl-7-oxo-7,8-dihydro-pyrido[2,3-d]pyrimidin-2-ylamino)-piperidine-1-carboxylic acid ethyl ester;
5-Amino-8-cyclohexyl-2-(4,4-difluoro-cyclohexylamino)-8H-pyrido[2,3-d]pyrimidin-7-one;
5-Amino-8-cyclobutyl-6-methyl-2-((1R,2S)-2-methyl-cyclohexylamino)-8H-pyrido[2,3-d]pyrimidin-7-one;
2-(1-Acetyl-piperidin-4-ylamino)-5-amino-8-cyclopentyl-6-methyl-8H-pyrido[2,3-d]pyrimidin-7-one;
5-Amino-8-cyclobutyl-6-methyl-2-((1S,2S)-2-methyl-cyclohexylamino)-8H-pyrido[2,3-d]pyrimidin-7-one;
2-(1-Acetyl-piperidin-4-ylamino)-5-amino-8-cyclohexyl-8H-pyrido[2,3-d]pyrimidin-7-one;
5-Amino-8-cyclobutyl-6-methyl-2-o-tolylamino-8H-pyrido[2,3-d]pyrimidin-7-one;
5-Amino-2-cyclohexylamino-8-phenyl-8H-pyrido[2,3-d]pyrimidin-7-one;
5-Amino-2-[4-(morpholine-4-carbonyl)-cyclohexylamino]-8-phenyl-8H-pyrido[2,3-d]pyrimidin-7-one;
5-Amino-2-(4,4-difluoro-cyclohexylamino)-8-methyl-8H-pyrido[2,3-d]pyrimidin-7-one;
5-Amino-8-benzyl-2-cyclohexylamino-8H-pyrido[2,3-d]pyrimidin-7-one;
5-Amino-2-(4-hydroxy-cyclohexylamino)-8-phenyl-8H-pyrido[2,3-d]pyrimidin-7-one;
6-Acetyl-5-amino-8-cyclobutyl-2-cyclohexylamino-8H-pyrido[2,3-d]pyrimidin-7-one;
5-Amino-8-benzyl-2-(tetrahydro-pyran-4-ylamino)-8H-pyrido[2,3-d]pyrimidin-7-one; and
5-Amino-8-cyclobutyl-2-(2,6-dimethyl-phenylamino)-6-methyl-8H-pyrido[2,3-d]pyrimidin-7-one.

5. A pharmaceutical composition comprising the compound of claim 4, admixed with at least one pharmaceutically acceptable carrier, excipient or diluent.

6. A method of treating a JNK-mediated disorder in a subject having a JNK-mediated disorder, said method comprising administering to a subject in need thereof a therapeutically effective amount of the compound of claim 1.

7. The method of claim 6, wherein the JNK-mediated disorder is arthritis.

8. The method of claim 7, wherein the arthritis is rheumatoid arthritis.

* * * * *

UNITED STATES PATENT AND TRADEMARK OFFICE
CERTIFICATE OF CORRECTION

PATENT NO. : 8,268,840 B2
APPLICATION NO. : 12/387181
DATED : September 18, 2012
INVENTOR(S) : Brookfield et al.

It is certified that error appears in the above-identified patent and that said Letters Patent is hereby corrected as shown below:

Claim 1, column 93, line 57, delete "$R^{1b}K$ is" and insert -- $R^{1b}$ is --

Claim 4, column 96, line 50, delete "pyridol[2,3-d]pyrimidin-7-on d]pyrimidin-7-one;"
and insert -- pyridol[2,3-d]pyrimidin-7-one]pyrimidin-7-one; --

Signed and Sealed this
Fifth Day of February, 2013

Teresa Stanek Rea
*Acting Director of the United States Patent and Trademark Office*